(12) United States Patent
Phillips

(10) Patent No.: US 10,624,620 B2
(45) Date of Patent: Apr. 21, 2020

(54) SYSTEMS AND METHODS FOR SEALING A PUNCTURE OF A VESSEL

(71) Applicant: Phillips Medical, LLC, Jefferson City, MO (US)

(72) Inventor: Victor Matthew Phillips, Jefferson City, MO (US)

(73) Assignee: Phillips Medical, LLC, Jefferson City, MO (US)

( * ) Notice: Subject to any disclaimer, the term of this patent is extended or adjusted under 35 U.S.C. 154(b) by 273 days.

(21) Appl. No.: 15/909,146

(22) Filed: Mar. 1, 2018

(65) Prior Publication Data
US 2018/0325505 A1   Nov. 15, 2018

Related U.S. Application Data

(63) Continuation-in-part of application No. 15/799,619, filed on Oct. 31, 2017.
(Continued)

(51) Int. Cl.
*A61B 17/04* (2006.01)
*A61B 17/00* (2006.01)
(Continued)

(52) U.S. Cl.
CPC ...... *A61B 17/0057* (2013.01); *A61B 17/0401* (2013.01); *A61B 17/0482* (2013.01);
(Continued)

(58) Field of Classification Search
CPC ............ A61B 17/0057; A61B 17/0401; A61B 17/0482; A61B 17/483; A61B 17/122;
(Continued)

(56) References Cited

U.S. PATENT DOCUMENTS

| 5,342,393 A | 8/1994 | Stack |
| 6,136,010 A | 10/2000 | Modesitt et al. |

(Continued)

FOREIGN PATENT DOCUMENTS

| EP | 1938761 A1 | 7/2008 |
| EP | 2166953 A2 | 3/2010 |

(Continued)

OTHER PUBLICATIONS

International Search Report and Written Opinion, dated Jun. 21, 2018, for related International Application No. PCT/US2018/024781 (8 pgs.).

(Continued)

*Primary Examiner* — Ryan J. Severson
*Assistant Examiner* — Socrates L Boutsikaris
(74) *Attorney, Agent, or Firm* — Armstrong Teasdale LLP

(57) ABSTRACT

A closure system configured to facilitate hemostasis at a puncture of a vessel includes a delivery sheath that extends longitudinally from a delivery sheath proximal end to a delivery sheath distal end. The delivery sheath defines a delivery sheath lumen extending therethrough and configured to receive a first guidewire therethrough. The system also includes an introducer needle configured to selectively couple to the delivery sheath for movement relative to the delivery sheath. The introducer needle is configured to form a secondary access site in the vessel at an offset from the puncture after the delivery sheath distal end is advanced through the puncture. The system further includes a stylet configured to be received through the delivery sheath lumen adjacent to the first guidewire. The stylet includes a stylet magnet configured to magnetically couple to a guidewire magnet of a second guidewire advanced through the secondary access site.

20 Claims, 33 Drawing Sheets

Related U.S. Application Data

(60) Provisional application No. 62/505,524, filed on May 12, 2017.

(51) Int. Cl.
   *A61B 17/122* (2006.01)
   *A61B 17/22* (2006.01)
   *A61B 90/00* (2016.01)

(52) U.S. Cl.
   CPC ......... *A61B 17/0483* (2013.01); *A61B 17/122* (2013.01); *A61B 2017/00004* (2013.01); *A61B 2017/00358* (2013.01); *A61B 2017/00477* (2013.01); *A61B 2017/00619* (2013.01); *A61B 2017/00623* (2013.01); *A61B 2017/00659* (2013.01); *A61B 2017/00663* (2013.01); *A61B 2017/00668* (2013.01); *A61B 2017/00672* (2013.01); *A61B 2017/00738* (2013.01); *A61B 2017/00876* (2013.01); *A61B 2017/0409* (2013.01); *A61B 2017/0417* (2013.01); *A61B 2017/22038* (2013.01); *A61B 2090/3966* (2016.02)

(58) Field of Classification Search
   CPC ........... A61B 2017/00004; A61B 2017/00358; A61B 2017/00477; A61B 2017/00619; A61B 2017/00623; A61B 2017/00659; A61B 2017/00663; A61B 2017/00668; A61B 2017/00672; A61B 2017/00738; A61B 2017/00876; A61B 2017/0409; A61B 2017/0417; A61B 2017/22038; A61B 2017/00637; A61B 2017/00646; A61B 2017/00676; A61B 2090/3966
   See application file for complete search history.

(56) References Cited

U.S. PATENT DOCUMENTS

| | | |
|---|---|---|
| 6,183,496 B1 | 2/2001 | Urbanski |
| 6,461,366 B1 | 10/2002 | Seguin |
| 6,582,452 B2 | 6/2003 | Coleman et al. |
| 6,616,686 B2 | 9/2003 | Coleman et al. |
| 6,669,714 B2 | 12/2003 | Coleman et al. |
| 6,770,083 B2 | 8/2004 | Seguin |
| 6,926,731 B2 | 8/2005 | Coleman et al. |
| 7,001,400 B1 | 2/2006 | Modesitt et al. |
| 7,008,435 B2 | 3/2006 | Cummins |
| 7,048,754 B2 | 5/2006 | Martin et al. |
| 7,111,768 B2 | 9/2006 | Cummins et al. |
| 7,163,551 B2 | 1/2007 | Anthony et al. |
| 7,288,097 B2 | 10/2007 | Seguin |
| 7,682,369 B2 | 3/2010 | Seguin |
| 7,753,935 B2 | 7/2010 | Brett et al. |
| 7,837,696 B2 | 11/2010 | Modesitt et al. |
| 7,850,701 B2 | 12/2010 | Modesitt et al. |
| 7,850,709 B2 | 12/2010 | Cummins et al. |
| 7,981,139 B2 | 7/2011 | Martin et al. |
| 8,048,108 B2 | 11/2011 | Sibbitt, Jr. et al. |
| 8,057,491 B2 | 11/2011 | Modesitt et al. |
| 8,192,459 B2 | 6/2012 | Cummins et al. |
| 8,323,298 B2 | 12/2012 | Modesitt et al. |
| 8,333,787 B2 | 12/2012 | Pipenhagen et al. |
| 8,366,742 B2 | 2/2013 | Coleman et al. |
| 8,398,676 B2 | 3/2013 | Roorda et al. |
| 8,469,995 B2 | 6/2013 | Cummins et al. |
| 8,529,598 B2 | 9/2013 | Jenson et al. |
| 8,556,954 B2 | 10/2013 | Ben Muvhar et al. |
| 8,590,760 B2 | 11/2013 | Cummins et al. |
| 8,657,852 B2 | 2/2014 | Roorda et al. |
| 8,758,397 B2 | 6/2014 | Sibbitt, Jr. et al. |
| 8,784,447 B2 | 7/2014 | Coleman et al. |
| 8,845,682 B2 | 9/2014 | Penner et al. |
| 8,906,050 B2 | 12/2014 | Brett et al. |
| 8,920,442 B2 | 12/2014 | Sibbitt, Jr. et al. |
| 8,932,324 B2 | 1/2015 | Sibbitt, Jr. et al. |
| 9,060,751 B2 | 6/2015 | Martin et al. |
| 9,060,769 B2 | 6/2015 | Coleman et al. |
| 9,089,311 B2 | 7/2015 | Fortson et al. |
| 9,131,932 B2 | 9/2015 | Tegels |
| 9,173,644 B2 | 11/2015 | Voss |
| 9,192,362 B2 | 11/2015 | Paul, Jr. et al. |
| 9,241,696 B2 | 1/2016 | Mehl |
| 9,295,469 B2 | 3/2016 | Cummins et al. |
| 9,314,230 B2 | 4/2016 | Roorda et al. |
| 9,402,625 B2 | 8/2016 | Coleman et al. |
| 9,414,820 B2 | 8/2016 | Voss et al. |
| 9,414,824 B2 | 8/2016 | Fortson et al. |
| 9,456,811 B2 | 10/2016 | Sibbitt, Jr. et al. |
| 9,486,191 B2 | 11/2016 | Gianotti et al. |
| 9,572,558 B2 | 2/2017 | Grant et al. |
| 9,610,070 B2 | 4/2017 | Martin |
| 9,662,099 B2 | 5/2017 | Grant et al. |
| 9,675,336 B2 | 6/2017 | Weisel et al. |
| 9,737,286 B2 | 8/2017 | Grant et al. |
| 2002/0002373 A1 | 1/2002 | Boehlke et al. |
| 2006/0190036 A1 | 8/2006 | Wendel et al. |
| 2007/0021778 A1 | 1/2007 | Carly |
| 2007/0060895 A1 | 3/2007 | Sibbitt et al. |
| 2008/0091264 A1 | 4/2008 | Machold et al. |
| 2008/0269801 A1 | 10/2008 | Coleman et al. |
| 2009/0171446 A1 | 7/2009 | Ainsworth et al. |
| 2009/0230168 A1 | 9/2009 | Coleman et al. |
| 2010/0152748 A1 | 6/2010 | Penner et al. |
| 2010/0152772 A1 | 6/2010 | Brett et al. |
| 2010/0168767 A1 | 7/2010 | Yassinzadeh et al. |
| 2010/0179567 A1 | 7/2010 | Voss et al. |
| 2010/0179589 A1 | 7/2010 | Roorda et al. |
| 2010/0185234 A1 | 7/2010 | Fortson et al. |
| 2011/0137338 A1 | 6/2011 | Phillips |
| 2011/0213410 A1 | 9/2011 | Ginn et al. |
| 2011/0218568 A1 | 9/2011 | Voss |
| 2011/0224713 A1 | 9/2011 | Fortson |
| 2011/0224728 A1 | 9/2011 | Martin et al. |
| 2011/0276075 A1* | 11/2011 | Fung ............... A61B 18/1492 606/185 |
| 2012/0165854 A1* | 6/2012 | Pipenhagen ....... A61B 17/0057 606/191 |
| 2012/0245597 A1 | 9/2012 | Tegels |
| 2012/0253387 A1 | 10/2012 | Teichman et al. |
| 2012/0296275 A1 | 11/2012 | Martin et al. |
| 2014/0345109 A1 | 11/2014 | Grant et al. |
| 2015/0066055 A1 | 3/2015 | Sibbitt, Jr. et al. |
| 2015/0088240 A1 | 3/2015 | Lam et al. |
| 2015/0094759 A1 | 4/2015 | Wolinsky et al. |
| 2015/0119928 A1 | 4/2015 | Penner et al. |
| 2015/0119929 A1 | 4/2015 | Penner et al. |
| 2015/0265261 A1 | 9/2015 | Alokaili |
| 2015/0282791 A1 | 10/2015 | Phillips et al. |
| 2016/0000417 A1 | 1/2016 | Voss |
| 2016/0051239 A1 | 2/2016 | Martin et al. |
| 2016/0051258 A1 | 2/2016 | Cummins et al. |
| 2016/0120415 A1 | 5/2016 | Webler |
| 2016/0151057 A1 | 6/2016 | Voss |
| 2016/0151613 A1 | 6/2016 | Penner et al. |
| 2016/0166241 A1 | 6/2016 | McGoldrick et al. |
| 2016/0174953 A1 | 6/2016 | Grant et al. |
| 2016/0213357 A1 | 7/2016 | Mehl |
| 2017/0020517 A1 | 1/2017 | Coleman et al. |
| 2017/0049426 A1 | 2/2017 | Gianotti et al. |
| 2017/0086806 A1 | 3/2017 | Sibbitt, Jr. et al. |
| 2017/0181736 A1 | 6/2017 | McGoldrick et al. |
| 2017/0209131 A1 | 7/2017 | Penner et al. |
| 2017/0281142 A1 | 10/2017 | Martin et al. |

FOREIGN PATENT DOCUMENTS

| | | |
|---|---|---|
| EP | 1879505 B1 | 10/2012 |
| EP | 2519161 A2 | 11/2012 |
| EP | 2658453 A2 | 11/2013 |
| EP | 2709712 A2 | 3/2014 |
| EP | 2260770 B1 | 7/2014 |

(56) References Cited

FOREIGN PATENT DOCUMENTS

| | | | |
|---|---|---|---|
| EP | 2819586 | A2 | 1/2015 |
| EP | 2996573 | A1 | 3/2016 |
| EP | 3232938 | A1 | 10/2017 |
| EP | 3232939 | A1 | 10/2017 |
| WO | 0033744 | A1 | 6/2000 |
| WO | 2006117766 | A2 | 11/2006 |
| WO | 2008152617 | A2 | 12/2008 |
| WO | 2011080588 | A2 | 7/2011 |
| WO | 2012090069 | A2 | 7/2012 |
| WO | 2012156819 | A2 | 11/2012 |
| WO | 2013128292 | A2 | 9/2013 |
| WO | 2014141209 | A1 | 9/2014 |
| WO | 2016096930 | A1 | 6/2016 |
| WO | 2016096932 | A1 | 6/2016 |
| WO | 2017102941 | A1 | 6/2017 |

OTHER PUBLICATIONS

International Search Report and Written Opinion, dated Apr. 9, 2019, for related International patent application No. PCT/US2019/013001.

* cited by examiner

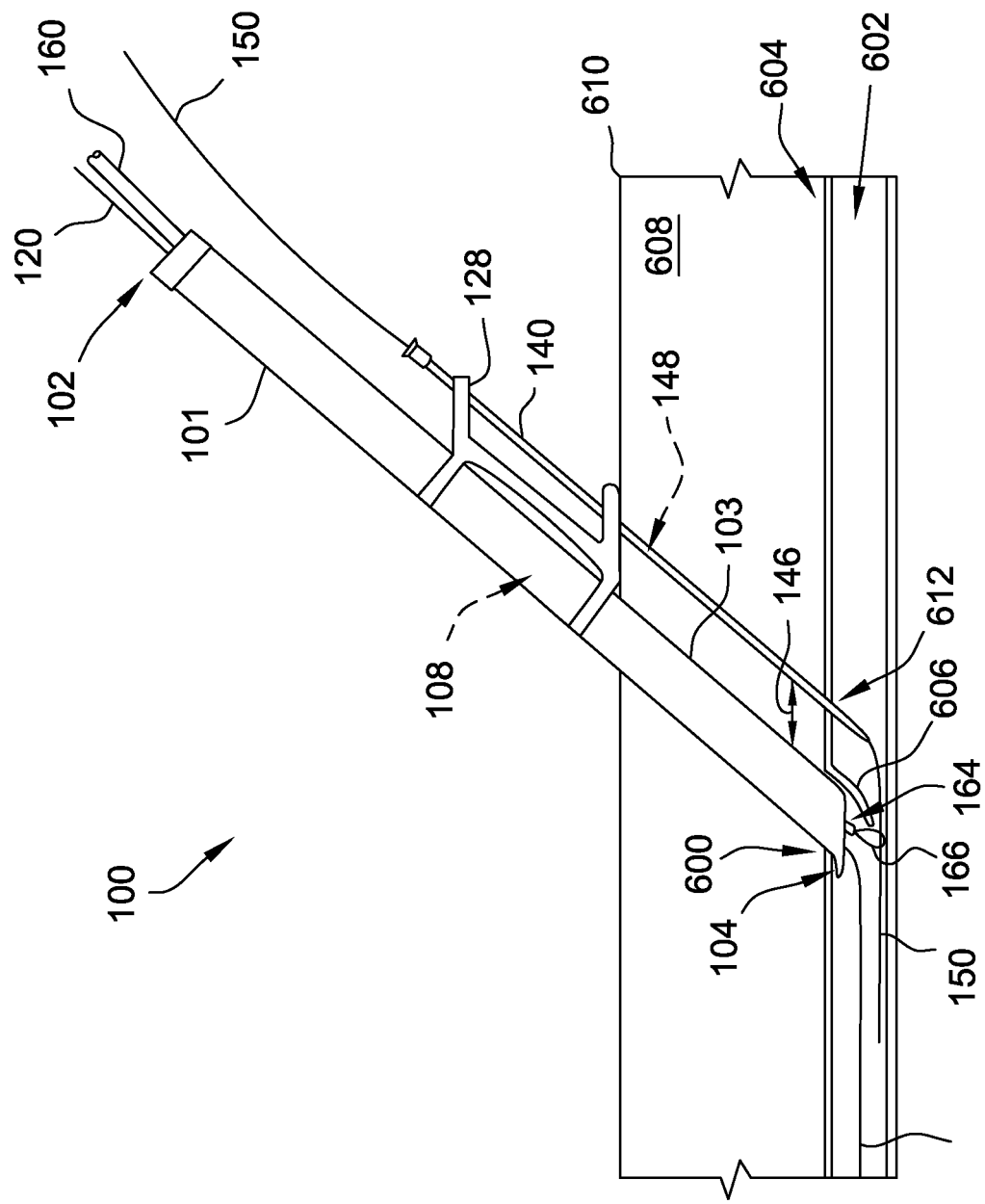

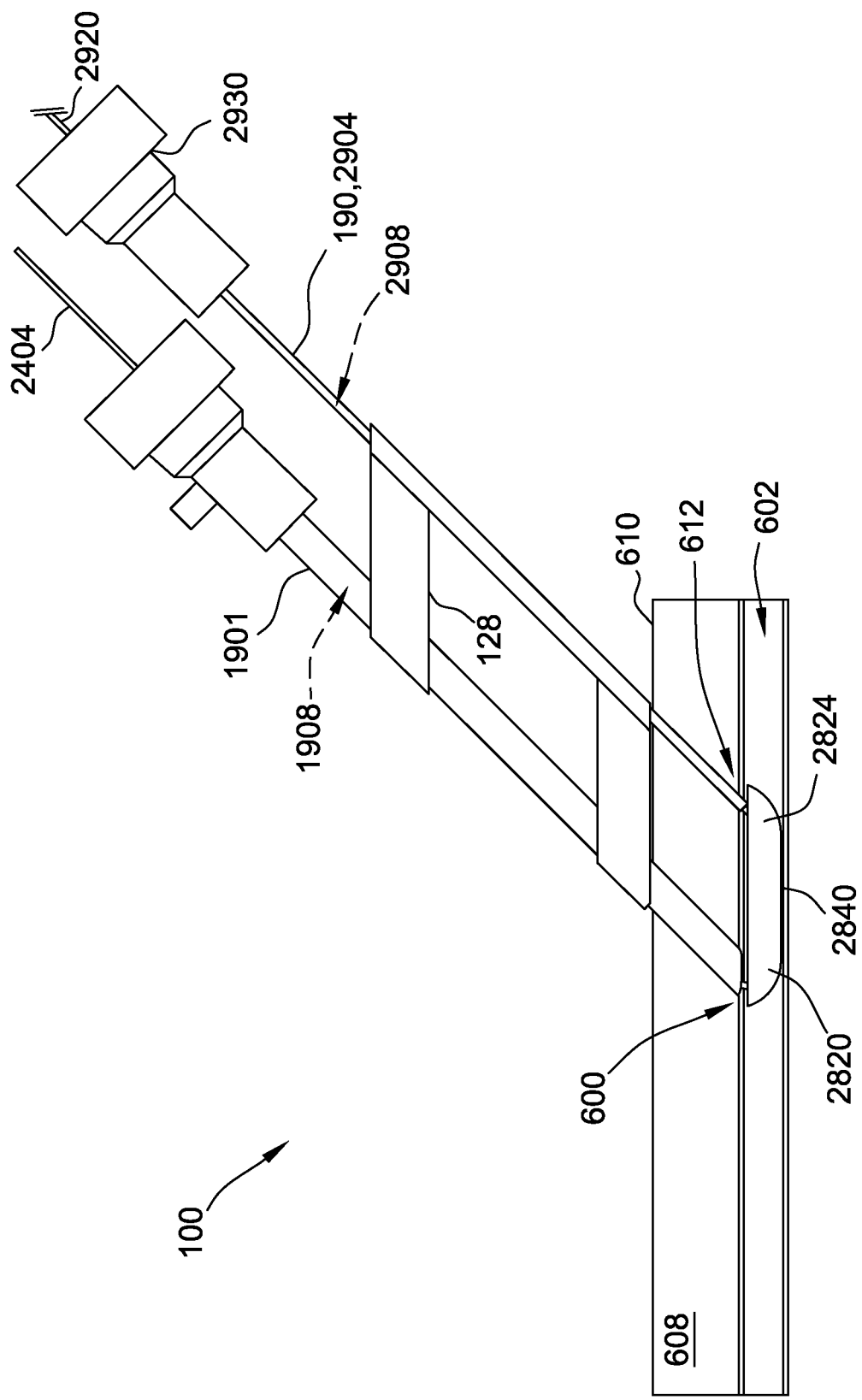

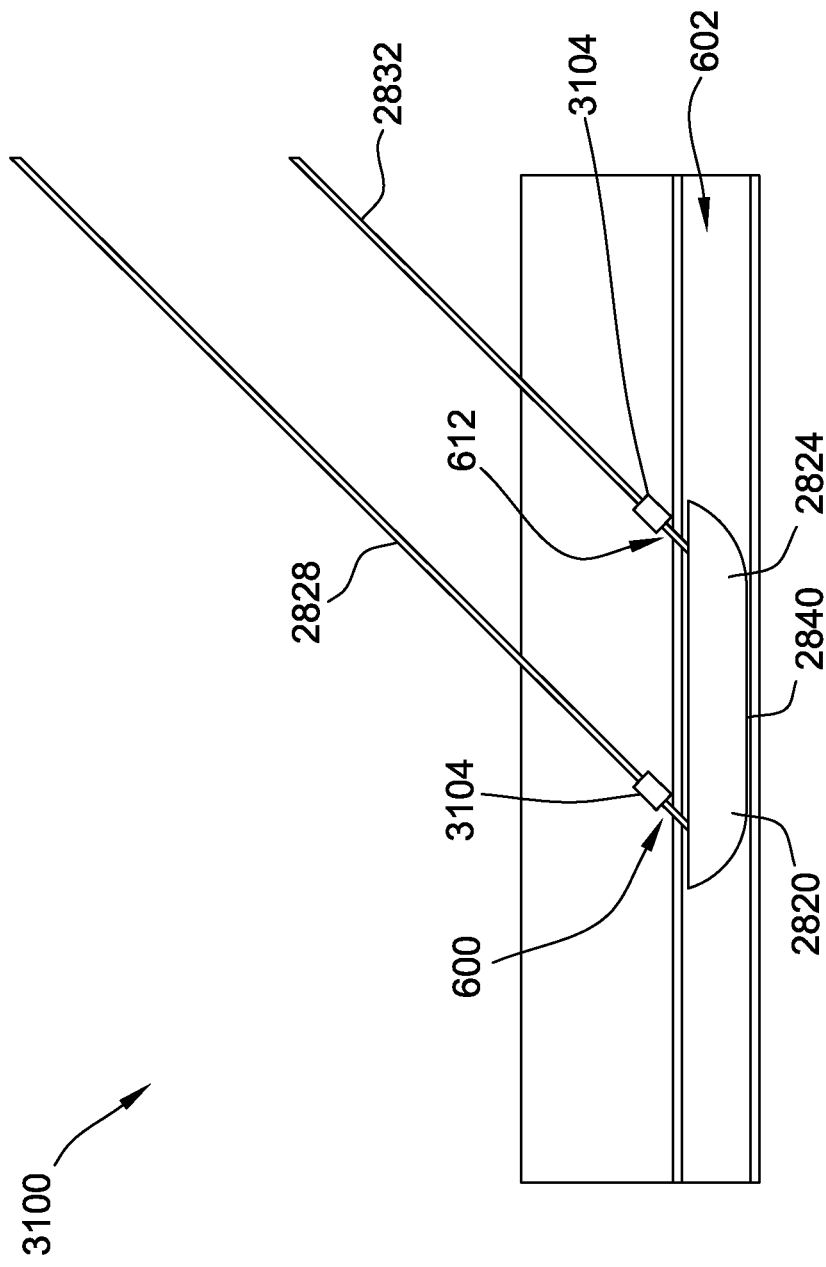

SYSTEMS AND METHODS FOR SEALING A PUNCTURE OF A VESSEL

CROSS REFERENCE TO RELATED APPLICATIONS

This application is a Continuation-in-Part (CIP) of U.S. patent application Ser. No. 15/799,619, filed Oct. 31, 2017, which claims the benefit of, and priority to, U.S. Provisional Pat. App. Ser. No. 62/505,524 filed May 12, 2017, the contents of both which are hereby incorporated by reference in their entirety.

BACKGROUND

The subject matter described herein relates generally to medical devices and, more particularly, to methods and systems for sealing a puncture of a vessel.

Catheter introducers are known to provide access to an artery for at least some medical procedures including, without limitation, cardiac catheterizations and peripheral endovascular procedures. After conducting such medical procedures, the catheter introducer is removed from the access site, leaving an arterial opening. At least some body fluids including, without limitation, blood are discharged from the arterial opening. Excess blood loss may endanger and/or traumatize the patient. One known method of controlling blood loss is through direct manual pressure over the arterial opening. However, in at least some cases, such as but not limited to medical procedures that require large-bore access through the artery wall, manual pressure alone is not sufficient to achieve hemostasis. For example, at least some such procedures are performed using catheter introducers of 14 Fr to 24 Fr diameter.

Another known method of controlling blood loss at a puncture site is the insertion of an implant, such as an anchor, balloon, disk, or the like, inside the lumen of the artery. The implant is then pulled back within the lumen and against the inner wall of the artery at the puncture site. The implant has a diameter at least slightly greater than the puncture opening, enabling the implant to be positioned to block blood loss through the puncture. However, in at least some cases, such as but not limited to medical procedures that require large-bore access through the artery wall, the required diameter of the implant approaches a diameter of the artery itself, increasing a risk that the implant may encounter an obstacle inside the artery that inhibits proper positioning, such as plaque, a smaller side branch of the artery, or the walls of the artery itself. For example, at least some such procedures result in puncture openings up to 8 millimeters in diameter, and the common femoral artery has an average diameter of 7 to 8 millimeters.

Moreover, in at least some cases, such as but not limited to medical procedures that require large-bore access through the artery wall, the insertion of the catheter introducer creates an inferior flap in the artery wall. A normal, healthy artery is compliant, that is, the inferior flap will recoil and elevate once the large bore procedural sheath is removed. However, at least some patients undergoing large bore cardiovascular procedures have unhealthy arteries. For example, calcium and atherosclerotic plaque are present in the wall of the common femoral artery, causing the artery to lose compliance and the ability to recoil. Thus, in at least some cases, the inferior flap does not elevate back towards the artery wall on its own once the large bore procedural sheath is removed, but rather remains deflected against the posterior wall of the artery. If the inferior flap is not elevated back towards alignment with the puncture opening during the deployment of the implant, there is a risk that the inferior flap will prevent a sufficient seal of the puncture site or obstruct the femoral artery. In at least some cases, the length of the inferior flap created is equal to the diameter of the large bore procedural sheath, for example 5 to 8 millimeters.

Another known method of controlling blood loss at a large bore puncture site is suturing the lumen of the artery. However, suturing the puncture site closed typically requires an incision to expose the artery and/or otherwise is a tedious procedure, and plaque may cause complications in driving the sutures through the vessel wall around the puncture site. Although some known devices have been developed to assist an operator in suturing a vessel puncture site, such known devices do not eliminate the tedious nature of manual suturing and also add a number of non-intuitive steps to the suturing process. Moreover, in at least some cases, the sutures have to be deployed at the beginning of the procedure, prior to the insertion of the large bore procedural sheath and the creation of the inferior flap in the wall of the artery, because after the inferior flap is created, known suturing devices do not successfully capture the inferior flap.

BRIEF SUMMARY

In one aspect, a closure system configured to facilitate hemostasis at a puncture of a vessel is provided. The system includes a delivery sheath that extends longitudinally from a delivery sheath proximal end to a delivery sheath distal end. The delivery sheath defines a delivery sheath lumen extending therethrough and configured to receive a first guidewire therethrough. The system also includes an introducer needle configured to selectively couple to the delivery sheath for movement relative to the delivery sheath. The introducer needle is configured to form a secondary access site in the vessel at an offset from the puncture after the delivery sheath distal end is advanced through the puncture. The system further includes a stylet configured to be received through the delivery sheath lumen adjacent to the first guidewire. The stylet includes a stylet magnet configured to magnetically couple to a guidewire magnet of a second guidewire advanced through the secondary access site.

In another aspect, a method of facilitating hemostasis at a puncture of a vessel is provided. The method includes advancing a distal end of a delivery sheath through the puncture into a lumen of the vessel. The delivery sheath extends longitudinally from a delivery sheath proximal end to the delivery sheath distal end, and the delivery sheath defines a delivery sheath lumen extending therethrough. The delivery sheath lumen receives a first guidewire therethrough. The method also includes advancing a distal end of a second guidewire through a secondary access site in the vessel at an offset from the puncture. The second guidewire includes a guidewire magnet. The method further includes extracting a stylet proximally from the delivery sheath lumen. A stylet magnet of the stylet magnetically couples to the guidewire magnet within the lumen of the vessel, such that the distal end of the second guidewire extends proximally from the delivery sheath proximal end after the stylet is extracted. Additionally, the method includes advancing an implant through the secondary access site into the lumen of the vessel adjacent to the puncture. The implant includes a first anchor suture constrained to move proximally with the second guidewire at least partially through the delivery sheath lumen. Moreover, the method includes advancing a first locking mechanism distally along the first anchor suture, such that the first locking mechanism couples against an exterior of the wall of vessel adjacent the puncture.

The features, functions, and advantages described herein may be achieved independently in various embodiments of the present disclosure or may be combined in yet other embodiments, further details of which may be seen with reference to the following description and drawings.

BRIEF DESCRIPTION OF THE DRAWINGS

FIG. 6 illustrates a stage of the method of FIG. 5B and of FIG. 5C;

FIG. 31 illustrates another stage of the method of FIG. 5F; and

FIG. 32 illustrates another stage of the method of FIG. 5F.

DETAILED DESCRIPTION

The methods and apparatus described herein relate to medical devices and, more particularly, to a closure system for use in facilitating hemostasis at a puncture of a vessel, such as but not limited to a puncture formed by a large-bore medical procedure. The system includes a delivery sheath configured for insertion over a first guidewire into the vessel puncture, such as through the tract formed by the primary medical procedure. A second guidewire is advanced into the vessel at a secondary access site in the vessel offset from the puncture. The second guidewire may be used in any of several ways to facilitate hemostasis at the puncture.

As used herein, an element or step recited in the singular and preceded with the word "a" or "an" should be understood as not excluding plural said elements or steps, unless such exclusion is explicitly stated. Further, references to an "embodiment" or an "implementation" are not intended to be interpreted as excluding the existence of additional embodiments or implementations that also incorporate the recited features. Moreover, unless explicitly stated to the contrary, embodiments or implementations "comprising," "including," or "having" an element or a plurality of elements having a particular property may include additional such elements not having that property.

Figure 1:
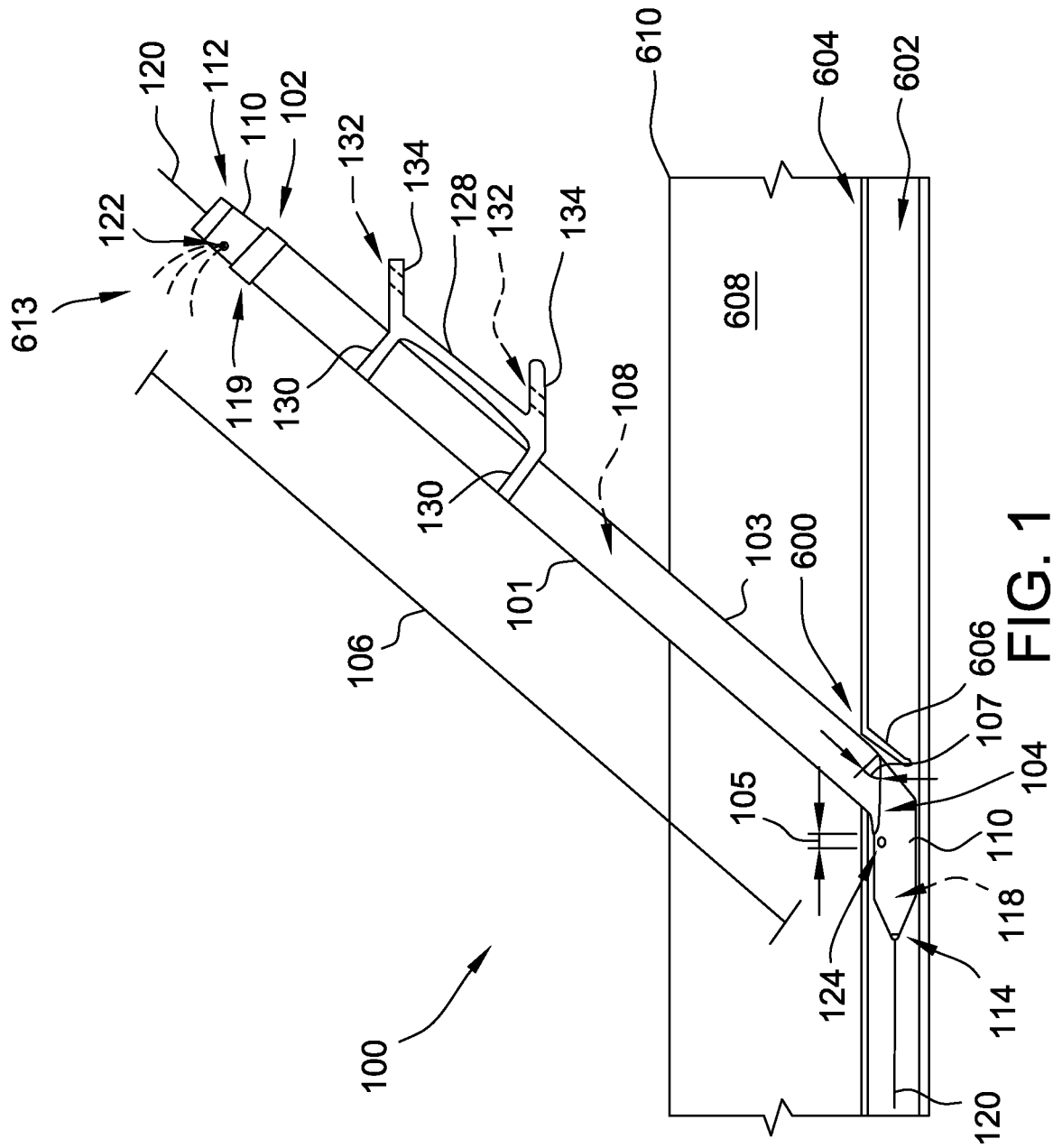
FIG. 1 is a schematic view of an exemplary closure system for facilitating hemostasis at a puncture of a vessel wall.

FIG. 1 is a schematic view of an exemplary closure system 100 for facilitating hemostasis at a puncture 600 of a wall of a vessel 604, such as but not limited to a femoral artery. Closure system 100 includes a primary delivery sheath or outer tube 101 that extends longitudinally from a proximal end 102 to a distal end 104 and defines a length 106 therebetween. In the exemplary embodiment, delivery sheath length 106 is between about 7 centimeters and about 10 centimeters. In alternative embodiments, delivery sheath length 106 is any suitable length that enables closure system 100 to function as described herein. In the exemplary embodiment, delivery sheath 101 has a diameter in a range of 14 Fr to 24 Fr, such as for use in facilitating hemostasis at a large bore puncture. In alternative embodiments, delivery sheath 101 has any suitable diameter that enables delivery sheath 101 to function as described herein. In the exemplary embodiment, delivery sheath 101 has a bevel angle 107 at distal end 104 that facilitates reducing interference of the sheath distal end with an inferior flap 606 of the vessel wall at the puncture site. In alternative embodiments, distal end 104 has any suitable shape that enables delivery sheath 101 to function as described herein. Delivery sheath 101 defines a lumen 108 extending therethrough from proximal end 102 to distal end 104.

Closure system 100 also includes a dilator or inner tube 110 that extends longitudinally from a proximal end 112 to a distal end 114. Dilator 110 is receivable at least partially through delivery sheath lumen 108, such that dilator distal end 114 extends distally from delivery sheath distal end 104. In the exemplary embodiment, dilator 110 is further sized such that dilator proximal end 112 extends proximally from delivery sheath proximal end 102 when dilator distal end 114 extends distally from delivery sheath distal end 104. In alternative embodiments, dilator proximal end 112 is positioned relative to delivery sheath proximal end 102 in any suitable fashion that enables closure system 100 to function as described herein.

In the exemplary embodiment, dilator 110 defines a first lumen 118 extending therethrough from proximal end 112 to distal end 114, and configured to receive a first guidewire 120 therethrough. Moreover, in the exemplary embodiment, dilator 110 defines a second lumen 119 extending therein between a proximal side opening 122 and a distal side opening 124. Dilator 110 and delivery sheath 101 cooperate such that distal side opening 124 is positioned adjacent and distal to delivery sheath distal end 104 by a distance 105 when dilator distal end 114 extends distally from delivery sheath distal end 104.

In the exemplary embodiment, dilator first lumen 118 and dilator second lumen 119 are separate, dual lumens not in flow communication with each other. In alternative embodiments, dilator first lumen 118 and dilator second lumen 119 are in flow communication and/or are simultaneously defined by a single lumen 118, 119.

In FIG. 1, closure system 100 is illustrated in use at puncture 600 in vessel 604. For example, first guidewire 120 is extended through skin 610 and subcutaneous tissue 608 into a lumen 602 of vessel 604 to facilitate a primary medical procedure that creates puncture 600, and after the primary medical procedure, dilator 110 and delivery sheath 101 are advanced along first guidewire 120 to engage puncture 600. For example, delivery sheath 101, and dilator 110 extending distally therefrom, are advanced until blood 613 from vessel 604 is channeled through distal side opening 124 and dilator lumen 119 and out of proximal side opening 122, such that an operator observes the reflux of blood 613 and confirms the positioning of distal end 104 of delivery sheath 101 within vessel 404 at puncture 600.

In some embodiments, inferior flap 606 of vessel 604 is created adjacent to puncture 600 during the primary medical procedure, and extends within vessel lumen 602 after the primary medical procedure. For example, calcium and/or atherosclerotic plaque in a wall of vessel 604 cause vessel 604 to have reduced compliance, and thus inferior flap 606 does not elevate on its own after a procedural sheath associated with the primary medical procedure is removed. In alternative embodiments, inferior flap 606 does not extend within vessel lumen 602.

In the exemplary embodiment, an outer diameter of delivery sheath 101 is selected to match an outer diameter of a sheath (not shown) used for the primary medical procedure. In alternative embodiments, delivery sheath 101 has any suitable outer diameter that enables closure system 100 to function as described herein. In the exemplary embodiment, delivery sheath 101 is inserted through skin 610 and subcutaneous tissue 608 at an oblique angle with respect to skin 610. More specifically, delivery sheath 101 is inserted at approximately the same orientation as a sheath used for the primary medical procedure, such that a trailing side 103 of delivery sheath 101, opposite a direction of extension of first guidewire 120, is aligned with a side of puncture 600 from which inferior flap 606 depends. Thus, trailing side 103 defines an acute angle, such as about a 30 to 45 degree angle, with respect to skin 610. In alternative embodiments, delivery sheath 101 is inserted at any suitable orientation that enables closure system 100 to function as described herein.

Further in the exemplary embodiment, bevel angle 107 of delivery sheath distal end 104 is approximately equal to the angle of insertion, facilitating insertion of dilator distal end 114 extending from delivery sheath distal end 104 into vessel lumen 602 in a direction opposite trailing side 103. In alternative embodiments, delivery sheath 101 proximate to distal end 104 is oriented in any suitable fashion, and dilator distal end 114 extends from delivery sheath distal end 104 in any suitable direction relative to trailing side 103, that enables closure system 100 to function as described herein.

Figure 2:
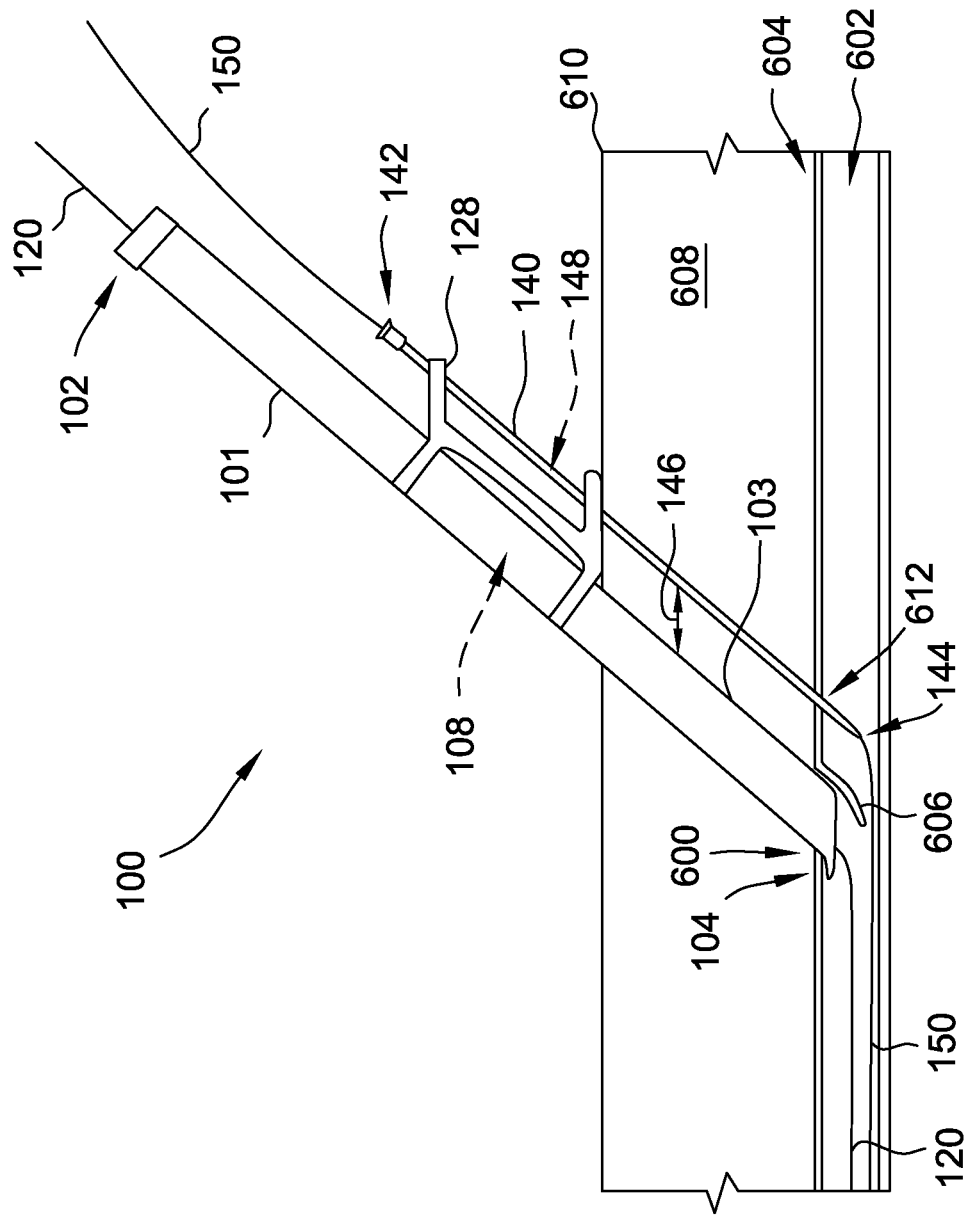
FIG. 2 is a schematic view of the closure system shown in FIG. 1 having a dilator removed and including an exemplary introducer needle.

FIG. 2 is a schematic view of closure system 100 having dilator 110 removed and including an exemplary introducer needle 140 coupled to delivery sheath 101. More specifically, introducer needle 140 is coupled to delivery sheath 101 at an offset 146 relative to delivery sheath 101. In certain embodiments, offset 146 is in a range from about 1.0 centimeters to about 3.0 centimeters. In some embodiments, offset 146 is in a range from about 1.0 centimeters to about 1.5 centimeters. In alternative embodiments, offset 146 is any suitable distance that enables closure system 100 to function as described herein.

With reference to FIGS. 1 and 2, after removal of dilator 110 over first guidewire 120, delivery sheath 101 is configured to remain in position having first guidewire 120 received through delivery sheath lumen 108. In the exemplary embodiment, introducer needle 140 is oriented generally parallel to, and at offset 146 relative to, trailing side 103 of delivery sheath 101. In alternative embodiments, introducer needle 140 is oriented in any suitable fashion relative to delivery sheath 101 that enables closure system 100 to function as described herein. Introducer needle 140 extends longitudinally from a proximal end 142 to a distal end 144. In addition, introducer needle 140 defines a lumen 148 extending therethrough from proximal end 142 to distal end 144 and configured to receive a second guidewire 150 therethrough.

In the exemplary embodiment, closure system 100 includes a bracket 128 configured to selectively couple introducer needle 140 to delivery sheath 101 at offset 146. More specifically, in the exemplary embodiment, bracket 128 includes at least one clip 130 sized to couple to delivery sheath 101, a pair of arms 134 coupled to the at least one clip 130 and extending away from delivery sheath trailing side 103, and a pair of aligned openings 132 defined in respective arms 134 and configured to receive introducer needle 140 therethrough such that introducer needle 140 is parallel to, and spaced at offset 146 from, trailing side 103 of delivery sheath 101. In some such embodiments, at least one clip 130 is slidably coupled to delivery sheath 101, such that introducer needle 140 is longitudinally and, optionally, rotationally positionable relative to delivery sheath 101 via sliding adjustment of bracket 128. In alternative embodiments, bracket 128 has any suitable structure that enables closure system 100 to function as described herein.

In alternative embodiments, introducer needle 140 is selectively coupled to delivery sheath 101 in any suitable fashion that enables closure system 100 to function as described herein. It should be understood that in other alternative embodiments, introducer needle 140 is not directly coupled to delivery sheath 101, and is oriented relative to delivery sheath 101 at offset 146 in any suitable fashion that enables closure system 100 to function as described herein.

Figure 5A:
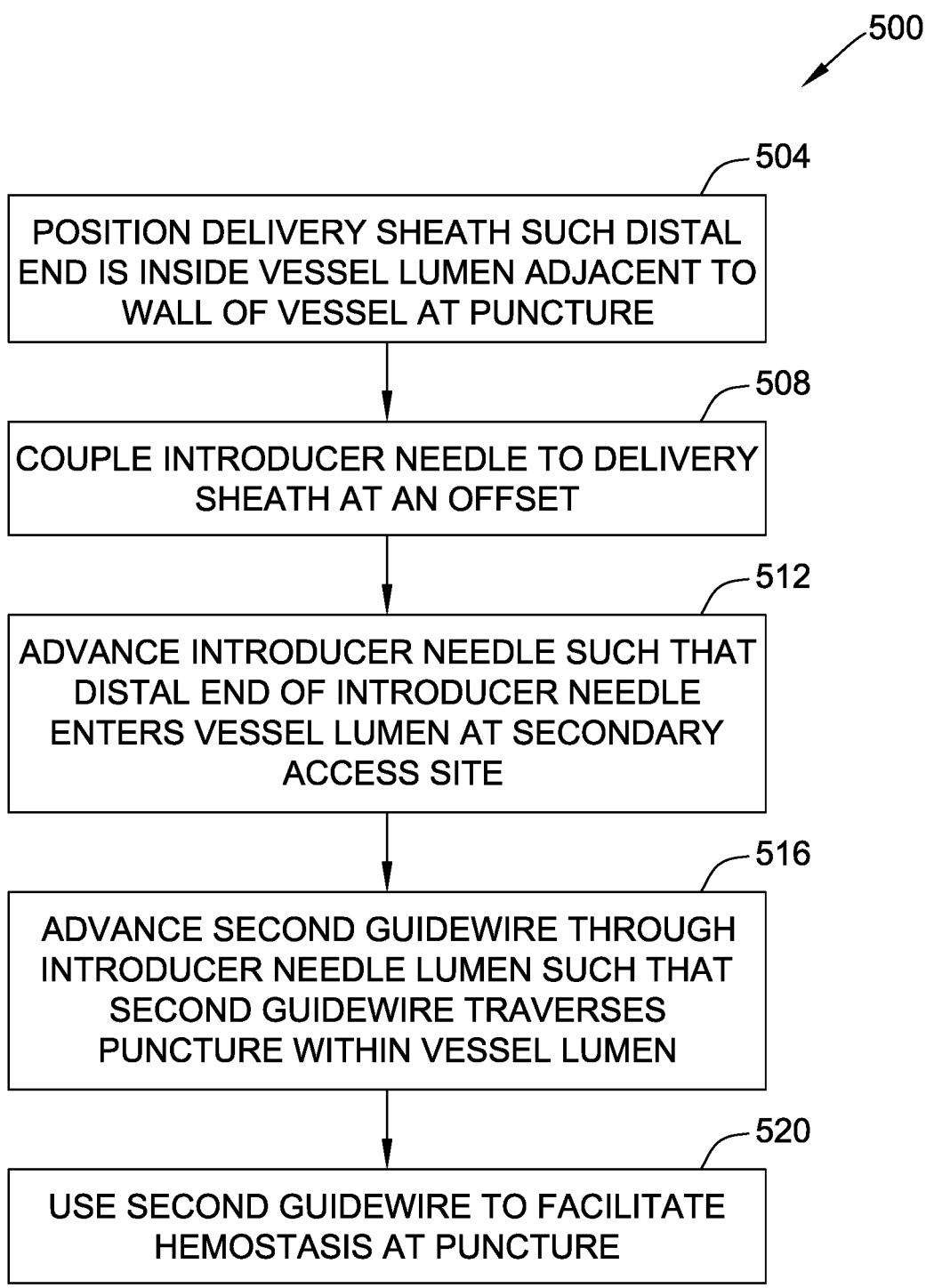
FIG. 5A is a flow diagram of an exemplary method of facilitating hemostasis at a puncture of a vessel using the closure system shown in FIG. 1.

FIG. 5A is a flow diagram of an exemplary method 500 of facilitating hemostasis at puncture 600 using closure system 100. In operation, an operator positions 504 delivery sheath 101 such that distal end 104 is inside vessel lumen 602 adjacent to a wall of vessel 604 at puncture 600, such as by observing blood reflux from dilator proximal side opening 122, as described above. In the exemplary embodiment, bracket 128 is positioned distally along delivery sheath 101 such that distal arm 134 contacts skin 610, as shown in FIG. 2. Introducer needle 140 is coupled 508 to delivery sheath 101 at offset 146, such as by inserting introducer needle 140 through openings 132. Introducer needle 140 is advanced 512 through skin 610 and subcutaneous tissue 608 such that distal end 144 of introducer needle 140 enters vessel lumen 602 at a secondary access site 612. For example, introducer needle 140 is advanced 512 until blood is seen refluxing from proximal end 142, indicating that distal end 144 is positioned within vessel lumen 602. Because introducer needle 140 is coupled to trailing side 103 of delivery sheath 101 at offset 146, secondary access site 612 is correspondingly spaced at offset 146 relative to the side of puncture 600 from which inferior flap 606 depends. It should be understood that in embodiments where introducer needle 140 is coupled other than parallel to delivery sheath 101, offset 146 varies between bracket 128 and secondary access site 612. Second guidewire 150 is advanced 516 through introducer needle lumen 148, such that second guidewire 150 traverses puncture 600 within vessel lumen 602. More specifically, second guidewire 150 extends within vessel lumen 602 from one side of puncture 600 to the other, and as such extends underneath inferior flap 606. Moreover, in the exemplary embodiment, secondary access site 612 is positioned on the side of puncture 600 from which inferior flap 606 depends, further facilitating second guidewire 150 extending within vessel lumen 602 directly underneath inferior flap 606. Second guidewire 150 is then used 520 to facilitate hemostasis at puncture 600.

Figure 4:
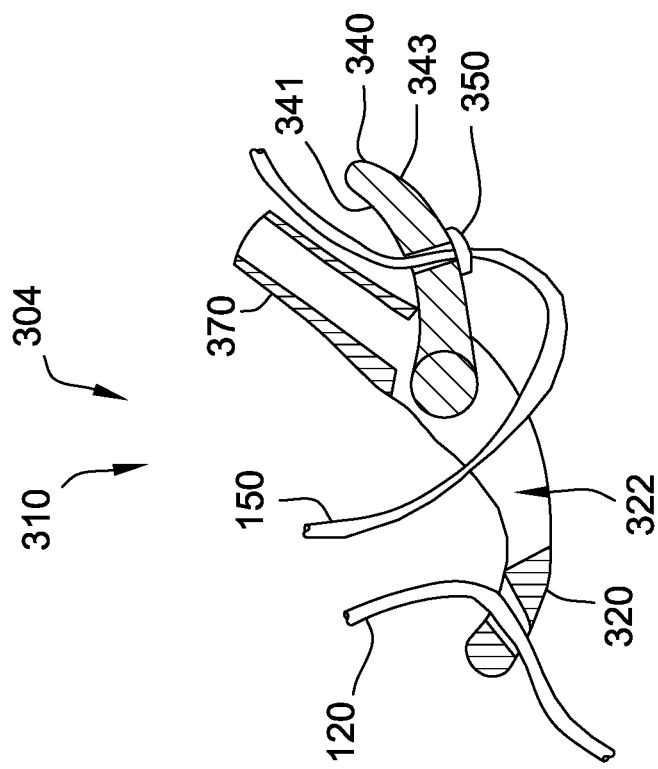
FIG. 4 is a sectional view of the anchor shown in FIG. 3, showing the anchor in a deployed configuration.
Figure 3:
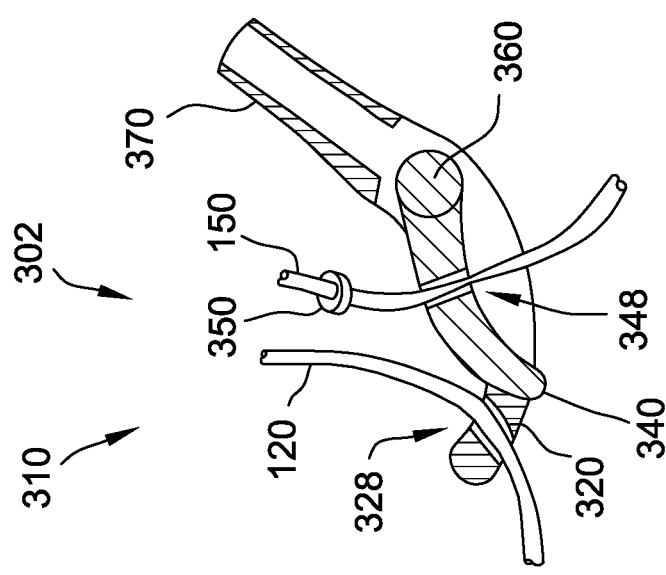
FIG. 3 is a sectional view of an exemplary anchor that may be used with the closure system shown in FIG. 1, showing the anchor in a delivery configuration.

FIG. 3 is a sectional view of an anchor 310 that may be used with closure system 100, showing anchor 310 in a delivery configuration 302. FIG. 4 is another sectional view of anchor 310, showing anchor 310 in a deployed configuration 304. With reference to FIGS. 2-4, in the exemplary embodiment, anchor 310 is configured to be delivered through delivery sheath lumen 108 into vessel lumen 602 in delivery configuration 302, and transitioned to deployed configuration 304 within vessel lumen 602 adjacent to the vessel wall using second guidewire 150 inserted through secondary access site 612. More specifically, anchor 310 in delivery configuration 302 is sized for insertion through puncture 600 into vessel lumen 602, while anchor 310 in deployed configuration 304 is sized to facilitate retention of at least a portion of anchor 310 within vessel lumen 602, i.e., sized sufficiently large to resist movement of at least a portion of anchor 310 back through the puncture opening.

In the exemplary embodiment, anchor 310 includes a first leg 320 coupled to a second leg 340. More specifically, second leg 340 is movable with respect to first leg 320 between delivery configuration 302, in which first leg 320 and second leg 340 extend substantially adjacent to each other, and deployed configuration 304, in which first leg 320 and second leg 340 extend in substantially different directions. For example, second leg 340 is rotatable in a first direction (counter-clockwise with respect to the view of FIGS. 3 and 4) with respect to first leg 320 to transition from delivery configuration 302 to deployed configuration 304. Alternatively, anchor 310 is transitionable between delivery configuration 302 and deployed configuration 304 in any suitable fashion that enables anchor 310 to function as described herein.

In the exemplary embodiment, first leg 320 and second leg 340 are each substantially rigid members, and are pivtoably coupled at a hinge 360. In alternative embodiments, first leg 320 and second leg 340 are coupled together in any suitable fashion that enables anchor 310 to function as described herein. In the exemplary embodiment, anchor 310 is formed from a suitable bioabsorbable material. In alternative embodiments, anchor 310 is formed from any suitable material that enables anchor 310 to function as described herein.

In the exemplary embodiment, first leg 320 includes a slot 322 extending therethrough and configured to at least partially receive second leg 340 in delivery configuration 302. More specifically, slot 322 enables passage of second guidewire 150 through first leg 320 without obstruction, and/or facilitates positioning of first leg 320 and second leg 340 substantially adjacent to each other in delivery configuration 302. In alternative embodiments, slot 322 extends only partially through first leg 320. In other alternative embodiments, first leg 320 does not include slot 322.

In the exemplary embodiment, each of first leg 320 and second leg 340 has a curved or hooked shape to facilitate secure coupling against an interior of a vessel wall and/or capture of an inferior flap of the vessel wall, as will be described herein. In alternative embodiments, each of first leg 320 and second leg 340 has any suitable shape that enables anchor 310 to function as described herein.

In some embodiments, first leg 320 and second leg 340 are covered by a suitable flexible mesh (not shown) that facilitates hemostasis at puncture 600 when anchor 310 is in deployed configuration 304. In alternative embodiments, anchor 310 does not include a mesh material.

In the exemplary embodiment, first leg 320 includes an opening 328 defined in first leg 320 and extending therethrough. Opening 328 is sized to receive first guidewire 120 therethrough to facilitate positioning of anchor 310 at puncture 600. Similarly, second leg 340 includes an opening 348 defined in second leg 340 and extending therethrough. Opening 348 is configured to receive second guidewire 150 therethrough. Second leg 340 includes a first side 341 configured to face an interior of a wall of vessel 604 when anchor 310 is in deployed configuration 304, and a second side 343 opposite first side 341.

Second guidewire 150 is used to transition second leg 340 from delivery configuration 302 to deployed configuration 304. For example, after second guidewire 150 is extended through introducer needle lumen 148 and routed through opening 348, as will be described herein, opposing ends 152 and 154 (shown in FIG. 7) of second guidewire 150 are simultaneously drawn proximally, while first leg 320 is held in position, to transition second leg 340 from delivery configuration 302 to deployed configuration 304. For another example, a catch 350 is secured to second guidewire 150 proximal to opening 348. Catch 350 is sized to prevent passage of catch 350 through opening 348, and first end 152 of second guidewire 150 is drawn proximally such that catch 350 is drawn against second side 343 of second leg 340, urging second leg 340 from delivery configuration 302 to deployed configuration 304. For example, catch 350 is formed from a knot tied in second guidewire 150. For another example, catch 350 is a bead slid over second guidewire 150 to a selected location and adhesively secured. Alternatively, second leg 340 cooperates with second guidewire 150 in any suitable fashion that enables anchor 310 to function as described herein.

In the exemplary embodiment, anchor 310 further includes a stem 370 coupled to first leg 320. In some embodiments, stem 370 facilitates positioning and control of anchor 310 via a suitable tool deployed within delivery sheath 101. Additionally or alternatively, stem 370 is configured to extend through puncture 600 after anchor 310 is deployed, and to couple to a cover (not shown) positioned outside and adjacent to vessel 604 to further facilitate hemostasis at puncture 600. In alternative embodiments, anchor 310 does not include stem 370.

Figure 5B:
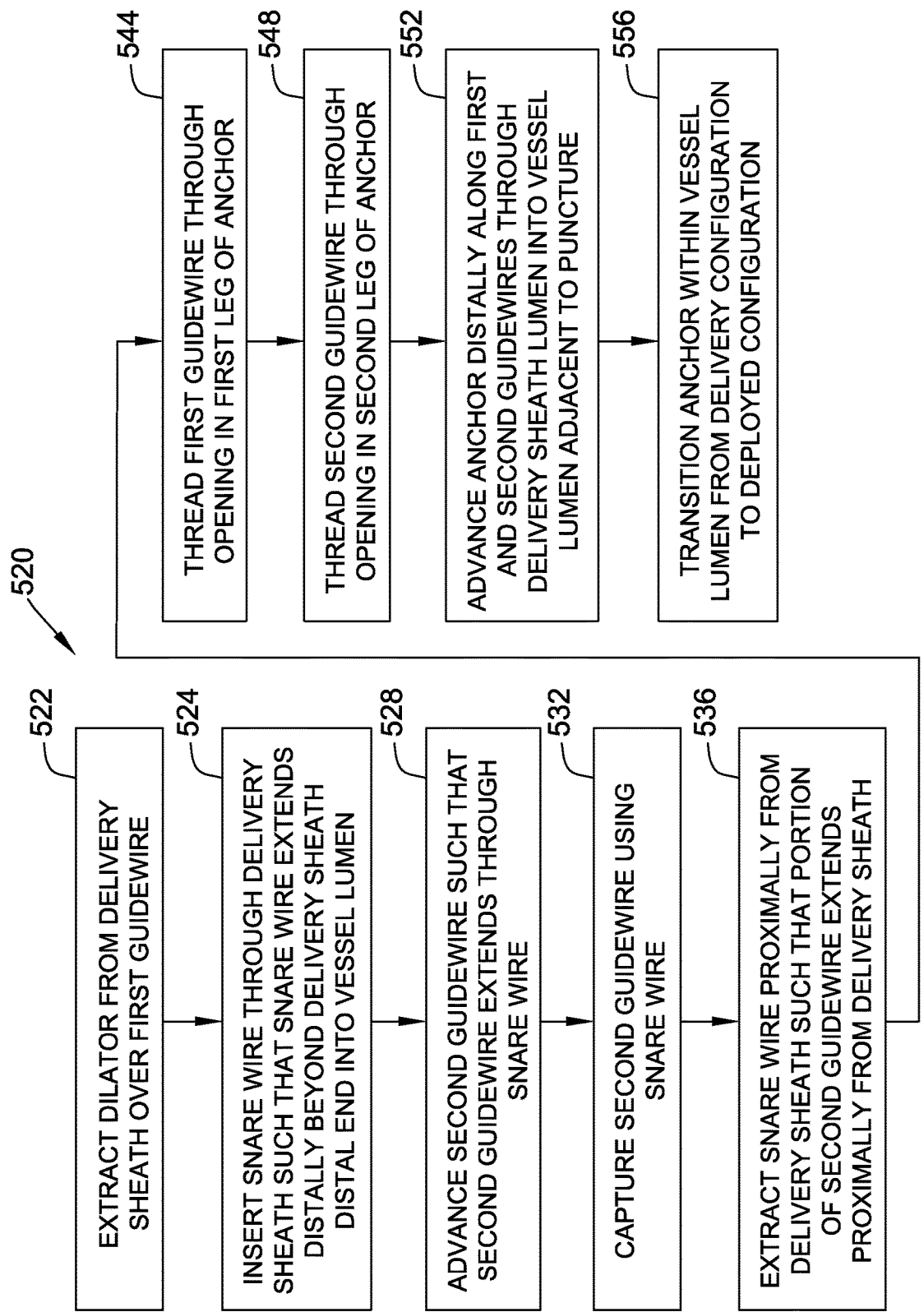
FIG. 5B is a flow diagram of a first exemplary embodiment of a step of the method shown in FIG. 5A.
Figure 7:
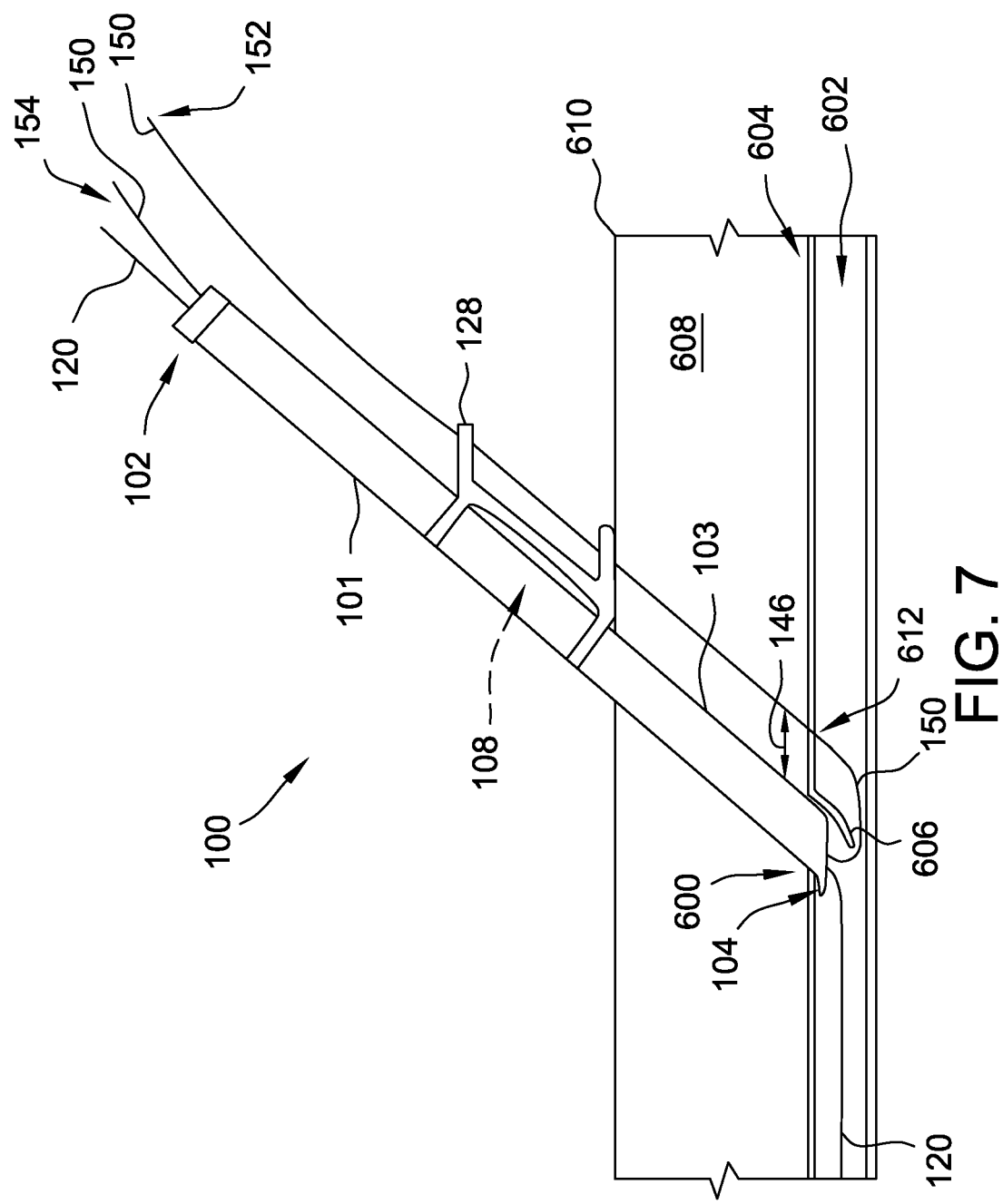
FIG. 7 illustrates another stage of the method of FIG. 5B.

FIG. 5B is a flow diagram of a first embodiment of step 520 of method 500, using second guidewire 150 to facilitate sealing of puncture 600. FIGS. 6-9 illustrate various stages of the first embodiment of step 520. With reference to FIGS. 5A, 5B, and 6, after delivery sheath distal end 104 is positioned 504 inside vessel lumen 602, as described above, dilator 110 is extracted 522 from delivery sheath 101 over first guidewire 120. A catheter 160, including a snare wire 166, such as a wire loop, extending from a distal end 164 thereof, is inserted 524 through delivery sheath lumen 108, such that snare wire 166 extends distally beyond delivery sheath distal end 104 into vessel lumen 602. Second guidewire 150 is advanced 528 through introducer needle lumen 148 and vessel lumen 602 such that second guidewire extends through snare wire 166. The operator uses snare wire 166 to capture 532 second guidewire 150, and the operator extracts 536 snare wire 166 proximally from delivery sheath 101, such that a portion of second guidewire 150 extends proximally from delivery sheath proximal end 102 adjacent to first guidewire 120, as shown in FIG. 7. More specifically, second guidewire 150 extends from a first end 152, distally through skin 610, subcutaneous tissue 608, and a wall of vessel 604 into vessel lumen 602, around inferior flap 606, and proximally through delivery sheath distal end 104, delivery sheath lumen 108, and out of delivery sheath proximal end 102 to a second end 154, as shown in FIG. 7. In some embodiments, introducer needle 140 is extracted proximally over second guidewire 150 and uncoupled from delivery sheath 101.

Figure 8:
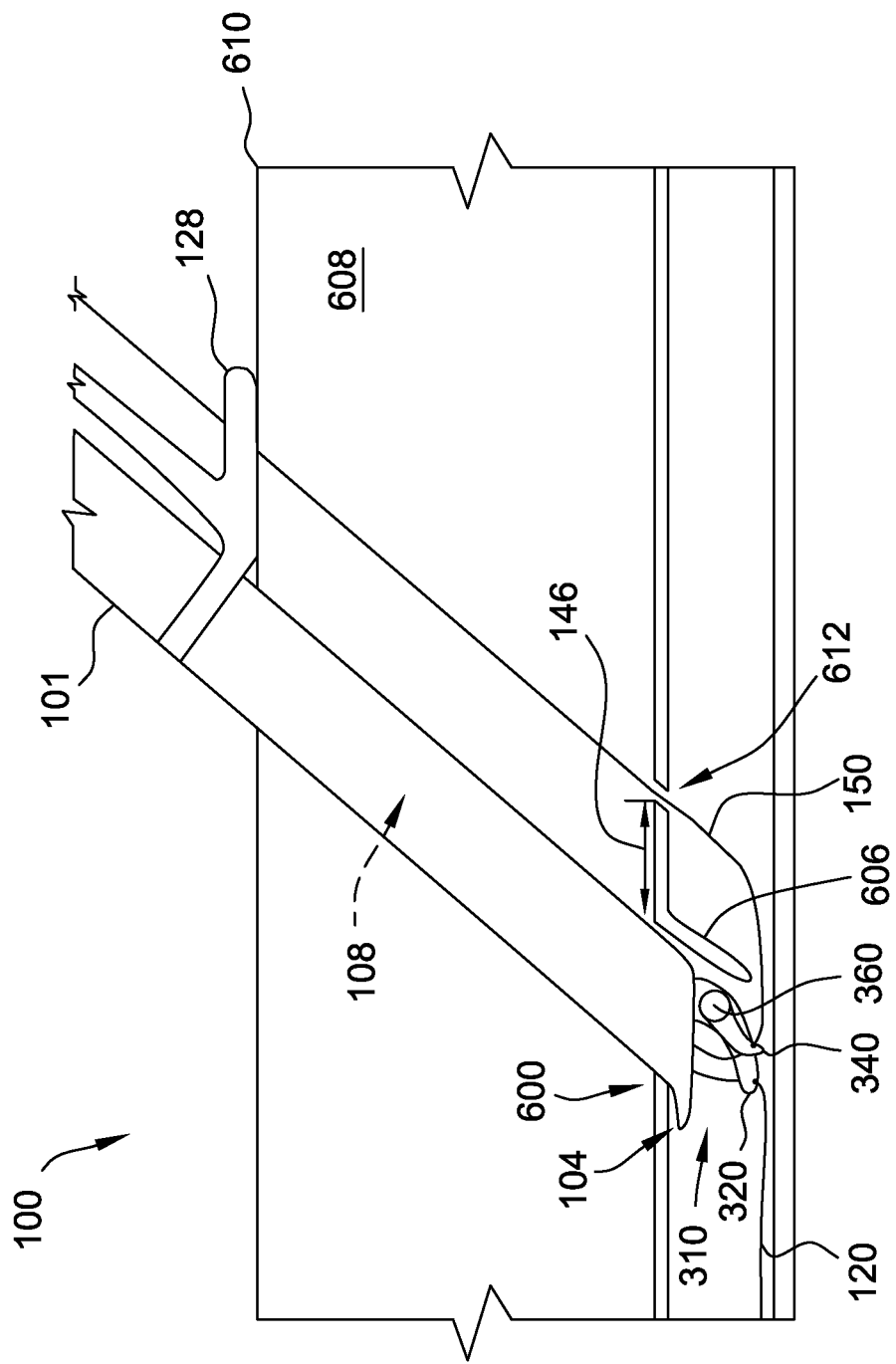
FIG. 8 illustrates another stage of the method of FIG. 5B.

With reference to FIGS. 3, 4, 5A, 5B, and 7-9, after first guidewire 120 and second guidewire 150 are positioned adjacent each other through puncture 600, anchor 310 is advanced 552 distally along first guidewire 120 and second guidewire 150 through delivery sheath lumen 108 into vessel lumen 602 adjacent to puncture 600, as shown in FIG. 8. For example, first guidewire 120 is threaded 544 through opening 328 defined in first leg 320, second guidewire 150 is threaded 548 through opening 348 defined in second leg 340, and anchor 310 in delivery configuration 302 is advanced 552 distally, such as using a pusher (not shown) within delivery sheath lumen 108, via sliding of openings 328 and 348 along respective guidewires 120 and 150.

Figure 9:
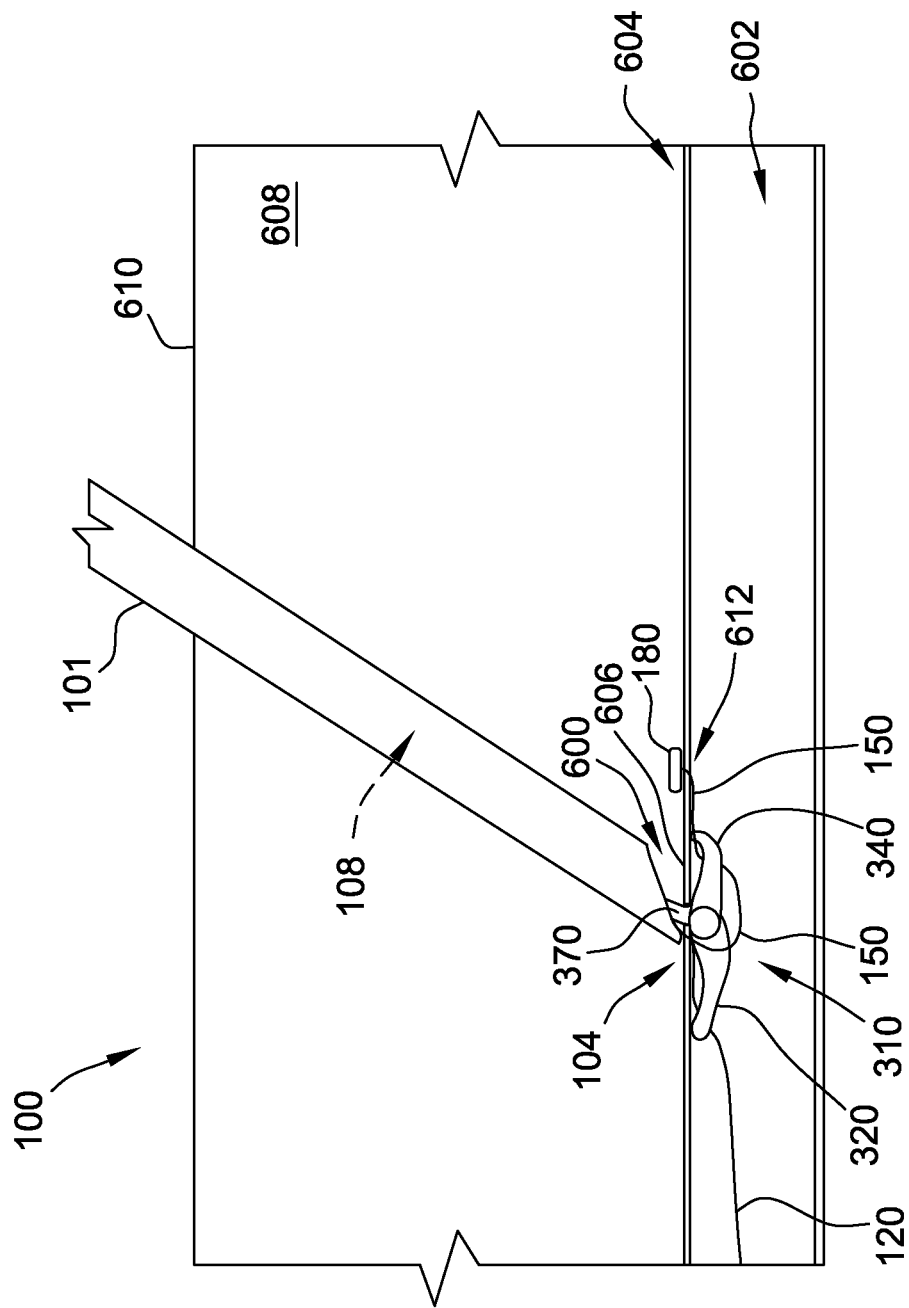
FIG. 9 illustrates another stage of the method of FIG. 5B.

Next, anchor 310 is transitioned 556 within vessel lumen 602 from delivery configuration 302 to deployed configuration 304. For example, while first leg 320 is held in place within vessel lumen 602 with respect to first guidewire 120, such as by using a pusher inserted through delivery sheath lumen 108 and coupled to first leg 320, opposing ends 152 and 154 (shown in FIG. 7) of second guidewire 150 are simultaneously drawn proximally, while first leg 320 is held in position, to move second leg 340 from delivery configuration 302 to deployed configuration 304. Alternatively, first end 152 of second guidewire 150 is drawn proximally such that catch 350 engages second side 343 of second leg 340, urging second leg 340 from delivery configuration 302 to deployed configuration 304. Alternatively, anchor 310 is transitioned 556 within vessel lumen 602 from delivery configuration 302 to deployed configuration 304 in any suitable fashion that enables anchor 310 to function as described herein. In some embodiments, second guidewire 150 traversing vessel lumen 602 between puncture 600 and secondary access site 612 guides second leg 340 of anchor 310 into elevating inferior flap 606 into a position proximate to puncture 600, as shown in FIG. 9.

After anchor 310 is deployed at puncture 600, in some embodiments, stem 370 extends through a wall of vessel 604 at puncture 600, and a suitable cover (not shown) may be advanced distally through delivery sheath lumen 108 and coupled to anchor 310 on the proximal side of the vessel wall to facilitate retaining anchor 310 at sealed puncture 600. First guidewire 120 and second guidewire 150 are withdrawn. Alternatively, anchor 310 is retained at sealed puncture 600 in any suitable fashion, such as by clipping second guidewire 150 at a first location outside vessel 604 adjacent to puncture 600 and at a second location outside vessel 604 adjacent to secondary access site 612, and tying off the clipped ends to secure the remaining portion of second guidewire 150 with respect to vessel 604, thereby securing anchor 310. In alternative embodiments, anchor 310 is retained at sealed puncture 600 in any suitable fashion that enables anchor 310 to function as described herein. In some embodiments, hinge 360 includes a locking mechanism (not shown) suitable to maintain first leg 320 of anchor 310 in deployed configuration 304 relative to second leg 340 after anchor 310 is transitioned.

In some embodiments, hemostasis at secondary access site 612 is controlled with manual pressure on skin 610. Alternatively, a secondary anchor 180 is coupled to second guidewire 150 between secondary access site 612 and first end 152 (shown in FIG. 7) of second guidewire 150, such as by a suture, and secondary anchor 180 is drawn against vessel 604 at secondary access site 612 as second end 154 of second guidewire 150 is drawn proximally through delivery sheath 101, for example prior to clipping second guidewire 150 at two locations as described above. Secondary anchor 180 is sized to facilitate hemostasis at the relatively smaller secondary access site 612. In alternative embodiments, hemostasis at secondary access site 612 is facilitated in any suitable fashion that enables closure system 100 to function as described herein.

Figure 5C:
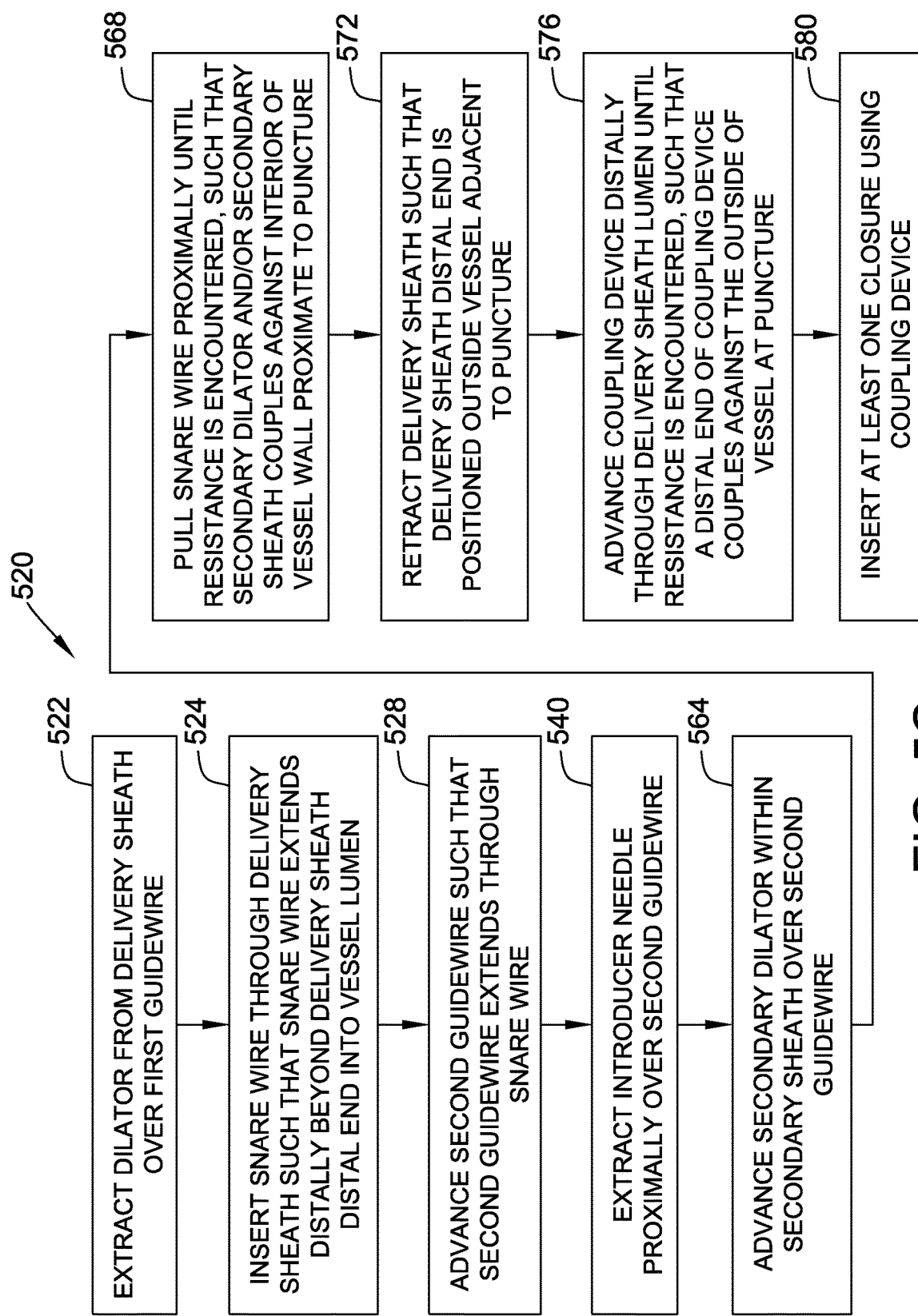
FIG. 5C is a flow diagram of a second exemplary embodiment of the step of the method shown in FIG. 5A.
Figure 10:
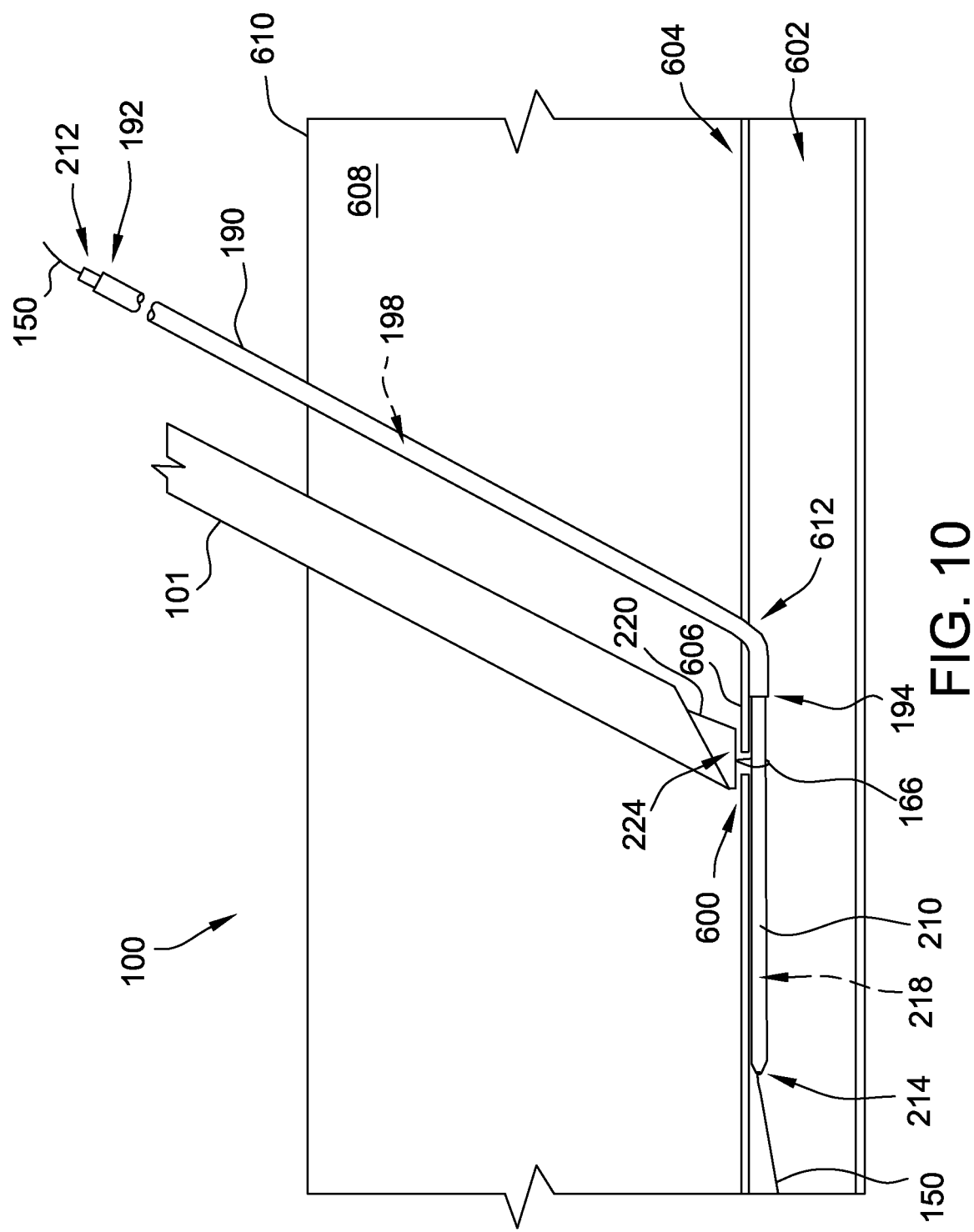
FIG. 10 illustrates another stage of the method of FIG. 5C.
Figure 11:
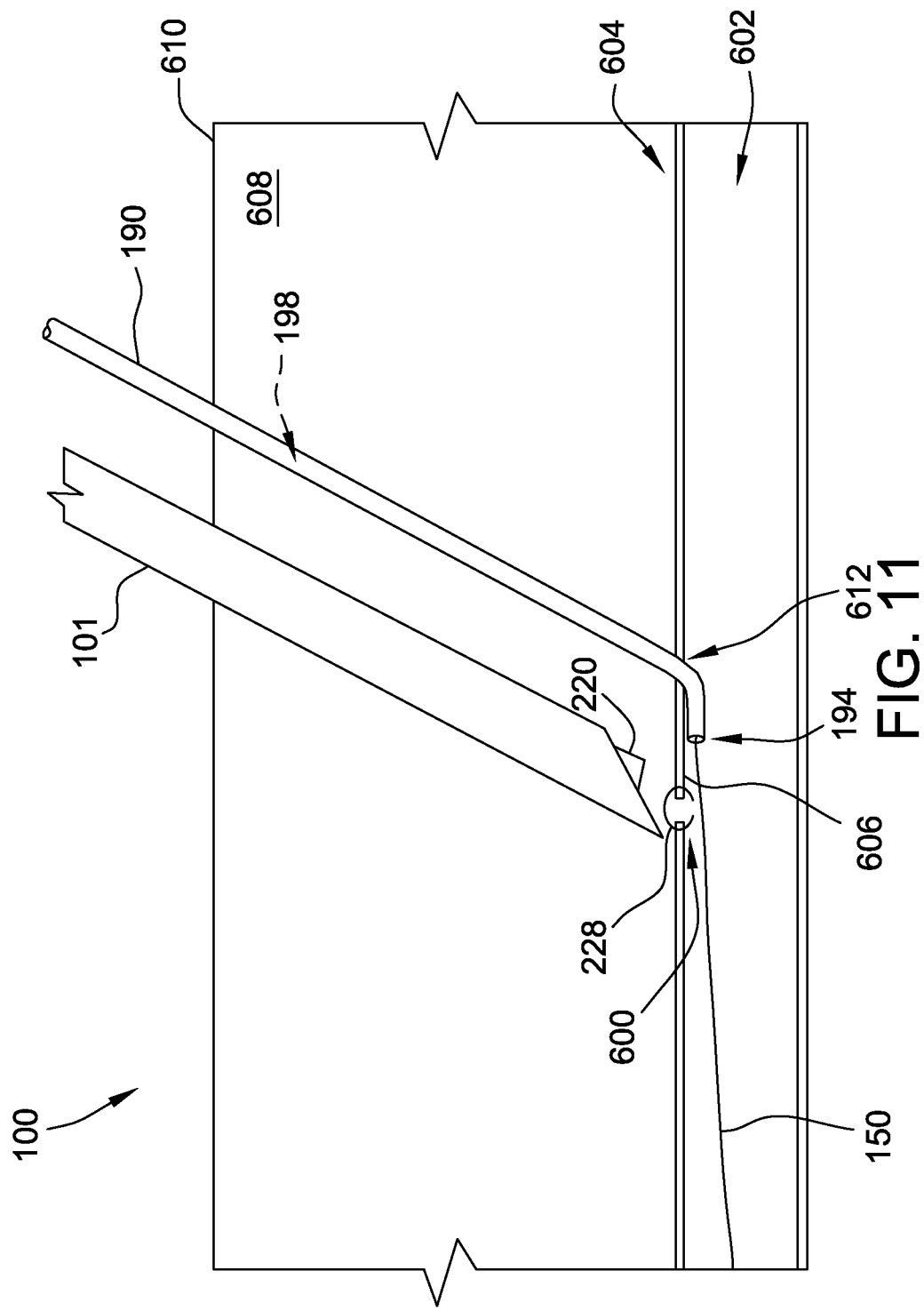
FIG. 11 illustrates another stage of the method of FIG. 5C.

FIG. 5C is a flow diagram of a second embodiment of step 520 of method 500, using second guidewire 150 to facilitate sealing of puncture 600. FIGS. 6, 10, and 11 illustrate various further stages of the second embodiment of step 520. With reference to FIGS. 5A, 5C, and 6, after delivery sheath distal end 104 is positioned 504 inside vessel lumen 602, as described above, dilator 110 is extracted 522 from delivery sheath 101 over first guidewire 120. Catheter 160, including snare wire 166 extending from a distal end 164 thereof, is inserted 524 through delivery sheath 101, such that snare wire 166 extends distally beyond delivery sheath distal end 104 into vessel lumen 602. Second guidewire 150 is advanced 528 through introducer needle lumen 148 and vessel lumen 602, such that second guidewire 150 extends through snare wire 166. Introducer needle 140 is extracted 540 proximally over second guidewire 150 and uncoupled from delivery sheath 101.

With reference to FIGS. 5C and 10, in the illustrated embodiment, closure system 100 further includes a secondary sheath 190 that extends longitudinally from a proximal end 192 to a distal end 194. In the exemplary embodiment, secondary sheath 190 is a 3 Fr sheath. In alternative embodiments, secondary sheath 190 has any suitable diameter that enables secondary sheath 190 to function as described herein. Secondary sheath 190 defines a lumen 198 extending therethrough from proximal end 192 to distal end 194. Closure system 100 also includes a secondary dilator 210 that extends longitudinally from a proximal end 212 to a distal end 214. Secondary dilator 210 is receivable at least partially through secondary sheath lumen 198, such that secondary dilator distal end 214 extends distally from secondary sheath distal end 194. In the exemplary embodiment, secondary dilator 210 defines a lumen 218 extending therethrough from proximal end 212 to distal end 214, and configured to receive second guidewire 150 therethrough.

In operation, secondary dilator 210 received within secondary sheath 190 is advanced 564 over second guidewire 150. In the exemplary embodiment, secondary dilator 210 is advanced such that secondary dilator distal end 214 extends distally beyond secondary sheath distal end 194 within vessel lumen 602, and such that secondary dilator 210 extends through, and is captured by, snare wire 166. The operator pulls 568 snare wire 166 proximally until resistance is encountered, such that at least one of secondary dilator 210 and secondary sheath 190 within vessel lumen 602 couples against the interior of the wall of vessel 604 proximate to puncture 600, thereby elevating inferior flap 606 into a position proximate to puncture 600, as shown in FIG. 10. The operator also retracts 572 delivery sheath 101 such that delivery sheath distal end 104 is positioned outside vessel 604 adjacent to puncture 600.

With reference to FIGS. 5C and 11, in the illustrated embodiment, closure system 100 also includes a coupling device 220. Coupling device 220 is any suitable device for closing a wall of vessel 604 over puncture 600, such as a suitable stapling or suturing device. Coupling device 220 is advanced 576 distally through delivery sheath lumen 108 until resistance is encountered, such that a distal end 224 of coupling device 220 couples against the outside of vessel 604 at puncture 600. While the operator continues to pull 568 snare wire 166 proximally, such that inferior flap 606 remains elevated in proximity to puncture 600, the operator inserts 580 at least one closure 228, such as a staple or suture, using coupling device 220. More specifically, the at least one closure 228 secures inferior flap 606 to other portions of the wall of vessel 604 surrounding puncture 600 to facilitate at least partial closure of, and hemostasis at, puncture 600. In the exemplary embodiment, the at least one closure 228 is formed from one of a bioabsorbable material and a metal material. In alternative embodiments, the at least one closure 228 is formed from any suitable material that enables the at least one closure 228 to function as described herein.

In some embodiments, after insertion 580 of the at least one closure 228, the operator removes secondary dilator 210 and second guidewire 150 from secondary sheath 190, and removes snare wire 166 and catheter 160 from delivery sheath 101. A completion arteriogram is then performed using a suitable material (not shown) injected through secondary sheath 190, confirming adequate closure of puncture 600. The operator then extracts secondary sheath 190 from secondary access site 612, and manual pressure is applied to skin 610 adjacent to secondary access site 612 until hemostasis is achieved.

Figures 14, 15:
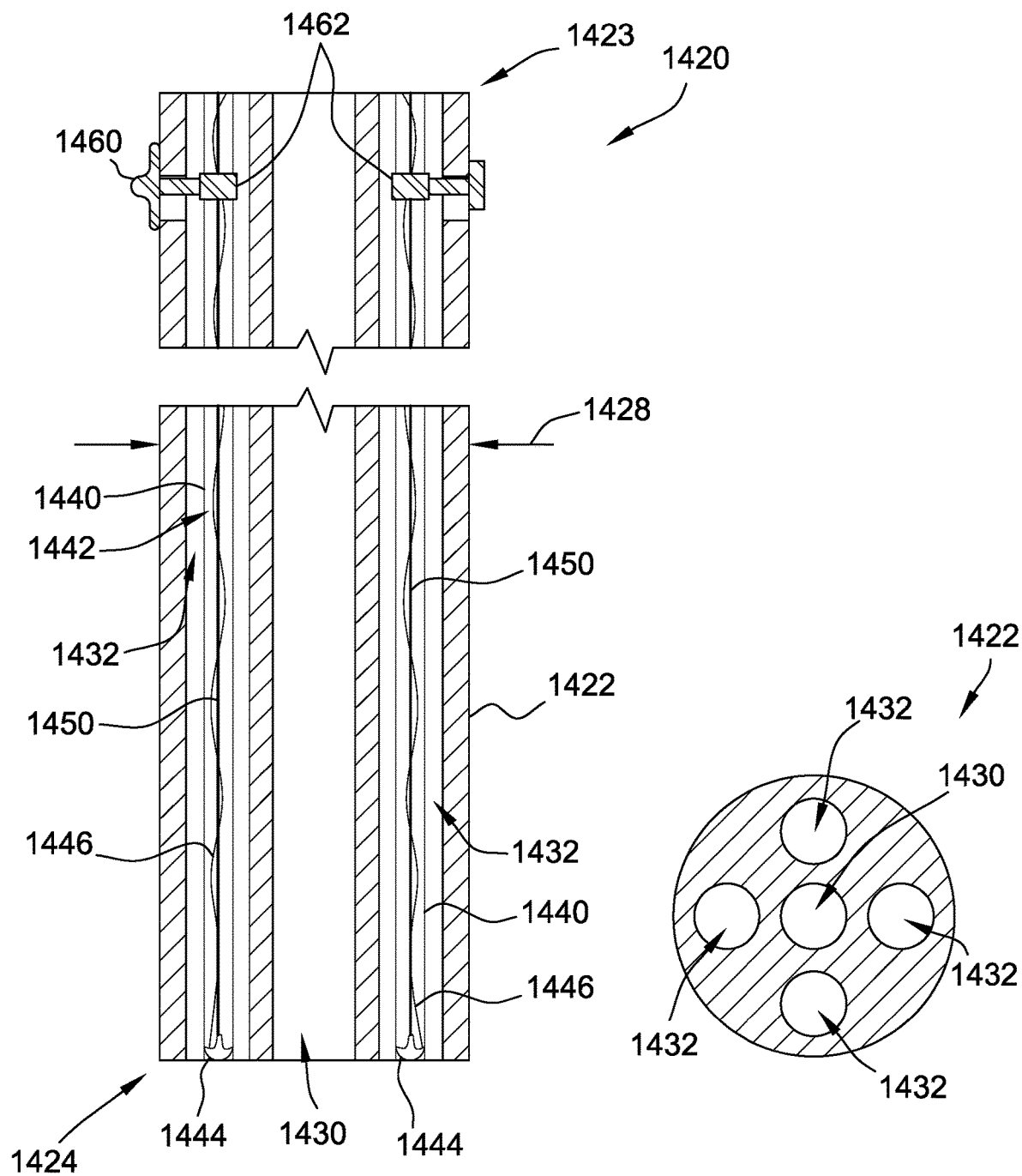
FIG. 14 is a schematic sectional view of an exemplary coupling device that may be used with the closure system shown in FIG. 1.
FIG. 15 is a schematic sectional view of an exemplary tube of the exemplary coupling device shown in FIG. 14.
Figure 16:
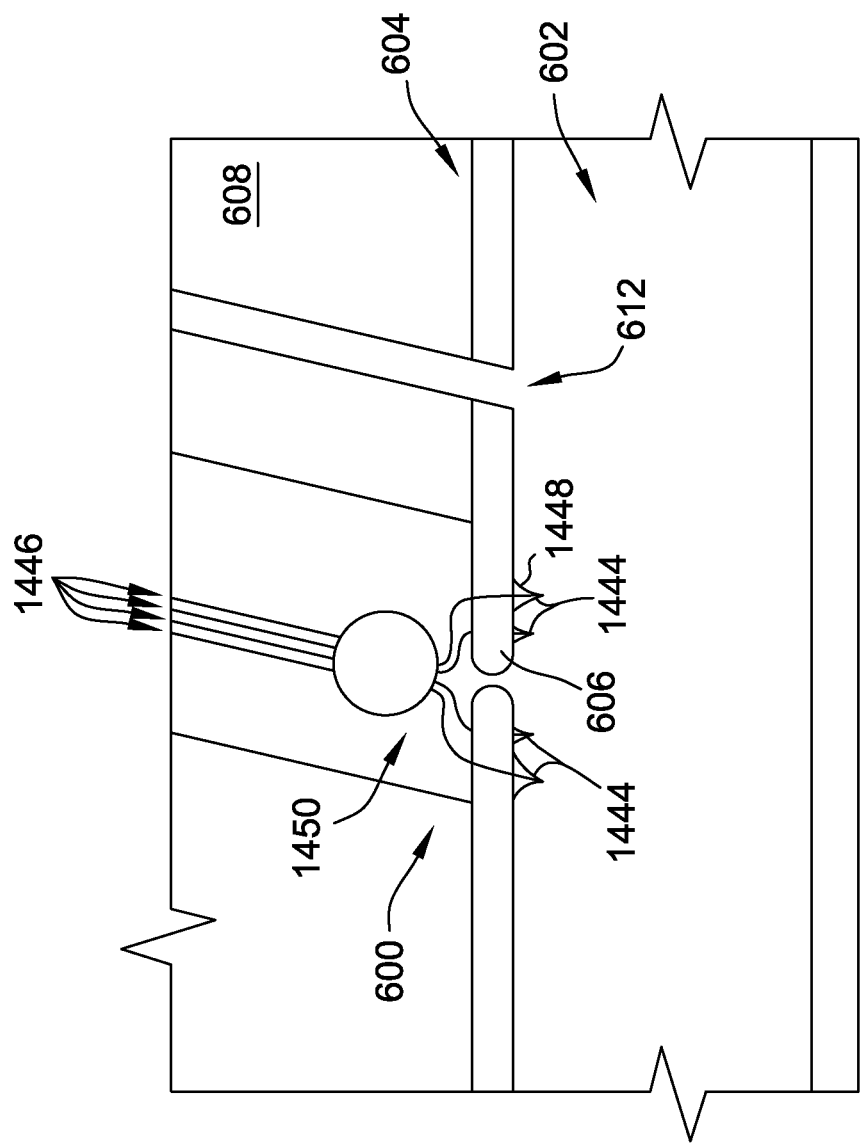
FIG. 16 illustrates an exemplary embodiment of a step of the method of FIG. 5C using the exemplary coupling device shown in FIG. 14.

FIG. 14 is a schematic sectional view of an exemplary embodiment of coupling device 220, designated coupling device 1420. FIG. 15 is a schematic sectional view of an exemplary tube 1422 of coupling device 1420. FIG. 16 illustrates an exemplary embodiment of step 580 of the method of FIG. 5C using coupling device 1420.

With reference to FIGS. 14 and 15, in the illustrated embodiment, coupling device 1420 includes a tube 1422 that extends from a proximal end 1423 to a distal end 1424. Tube 1422 has an outer diameter 1428 sized to be received through delivery sheath lumen 108 in a clearance fit. A central lumen 1430 is defined in tube 1422 and extends therethrough from proximal end 1423 to distal end 1424. Central lumen 1430 is sized to receive first guidewire 120 and snare catheter 160 including snare wire 166 (shown in FIG. 6) therethrough.

Tube 1422 also includes a plurality of access lumens 1432 defined therein and extending through distal end 1424 and proximally towards proximal end 1423. Access lumens 1432 are positioned peripherally about central lumen 1430. In the exemplary embodiment, access lumens 1432 extend proximally through proximal end 1423. In alternative embodiments, access lumens 1432 extend proximally to any suitable extent that enables coupling device 1420 to function as described herein. In the exemplary embodiment, the plurality of access lumens 1432 includes four access lumens 1432 positioned about central lumen 1430 in respective quadrants of tube 1422. In alternative embodiments, the plurality of access lumens 1432 includes any suitable number of access lumens 1432 positioned about central lumen 1430 in any suitable fashion that enables coupling device 1420 to function as described herein.

Coupling device 1420 also includes a respective access needle 1440 positionable within each of the plurality of access lumens 1432. Each access needle 1440 defines an access needle lumen 1442 extending therethrough, and a distal tip of each access needle 1440 is configured to penetrate the wall of vessel 604. A respective anchor 1444 is positioned within each access needle lumen 1442 proximate the distal end of access needle 1440, and a respective suture 1446 extends within access needle lumen 1442 and is coupled to each anchor 1444. In the exemplary embodiment, anchors 1444 and sutures 1446 are formed from suitable bioabsorbable materials.

In addition, coupling device 1420 includes a respective push rod 1450 extending within each access needle lumen 1442 proximal to the respective anchor 1444. Push rod 1450 is configured to push anchor 1444 distally out of the distal tip of access needle 1440 after access needle 1440 has penetrated the wall of vessel 604. In the exemplary embodiment, coupling device 1420 includes a lever 1460, adjacent to proximal end 1423 and accessible to a user, operatively coupled to access needles 1440 installed within access lumens 1432. Upon activation by the user, lever 1460 is configured, via any suitable coupling 1462, to first advance access needles 1440 distally out of tube 1422 over a first predefined distance, and second advance pusher rods 1450 distally out of access needles 1440 over a second predefined distance. In alternative embodiments, each access needle 1440 and corresponding pusher rod 1450 is suitably coupled to a respective dedicated lever 1460, such that each access needle 1440 is individually actuatable. In other alternative embodiments, coupling device 1420 is configured to enable selective distal advancement of access needles 1440 and/or pusher rods 1450 in any suitable fashion that enables coupling device 1420 to function as described herein.

With reference to FIGS. 5C, 10, and 14-16, in some embodiments, coupling device 1420 is used to perform the method shown in FIG. 5C. In operation, after coupling device 220 embodied as coupling device 1420 is advanced through delivery sheath lumen 108 such that distal end 1424 is positioned adjacent the outside of the wall of vessel 604, and snare wire 166 is pulled proximally to elevate inferior flap 606, lever 1460 is activated. As described above, the distal tips of access needles 1440 advance distally, penetrate the wall of vessel 604, and enter vessel lumen 602, and push rods 1450 push anchors 1444 distally out of the distal tips of access needles 1440 and into vessel lumen 602. Due to the elevation of inferior flap 606 into position proximate to puncture 600 in step 568, as discussed above, at least some anchors 1444 are inserted through and capture inferior flap 606.

Anchors 1444 are shaped to resist being pulled back through the wall of vessel 604. For example, in the exemplary embodiment, each anchor 1444 includes a plurality of extensions 1448 that extend outwardly in opposing directions to catch against an interior of the wall of vessel 604 and resist being pulled back through the wall. Coupling device 1420 is then withdrawn proximally over first guidewire 120, snare catheter 160, and snare wire 166, exposing the proximal ends of sutures 1446. A knot pusher or other suitable instrument (not shown) is then used to advance at least one knot 1452 distally along sutures 1446 towards puncture 600. The at least one knot 1452 and the anchors 1444 cooperate to secure sutures 1146 across puncture 600 as shown in FIG. 16, embodying the at least one closure 228 as described above. In some embodiments, delivery sheath 101 is also withdrawn proximally over first guidewire 120, snare catheter 160, and snare wire 166 prior to distal advancement of the at least one knot 1452.

In some embodiments, as discussed above, a completion arteriogram is also performed using a suitable material (not shown) injected through secondary sheath 190, confirming adequate closure of puncture 600, prior to extraction of secondary sheath 190 from secondary access site 612.

Figure 5D:
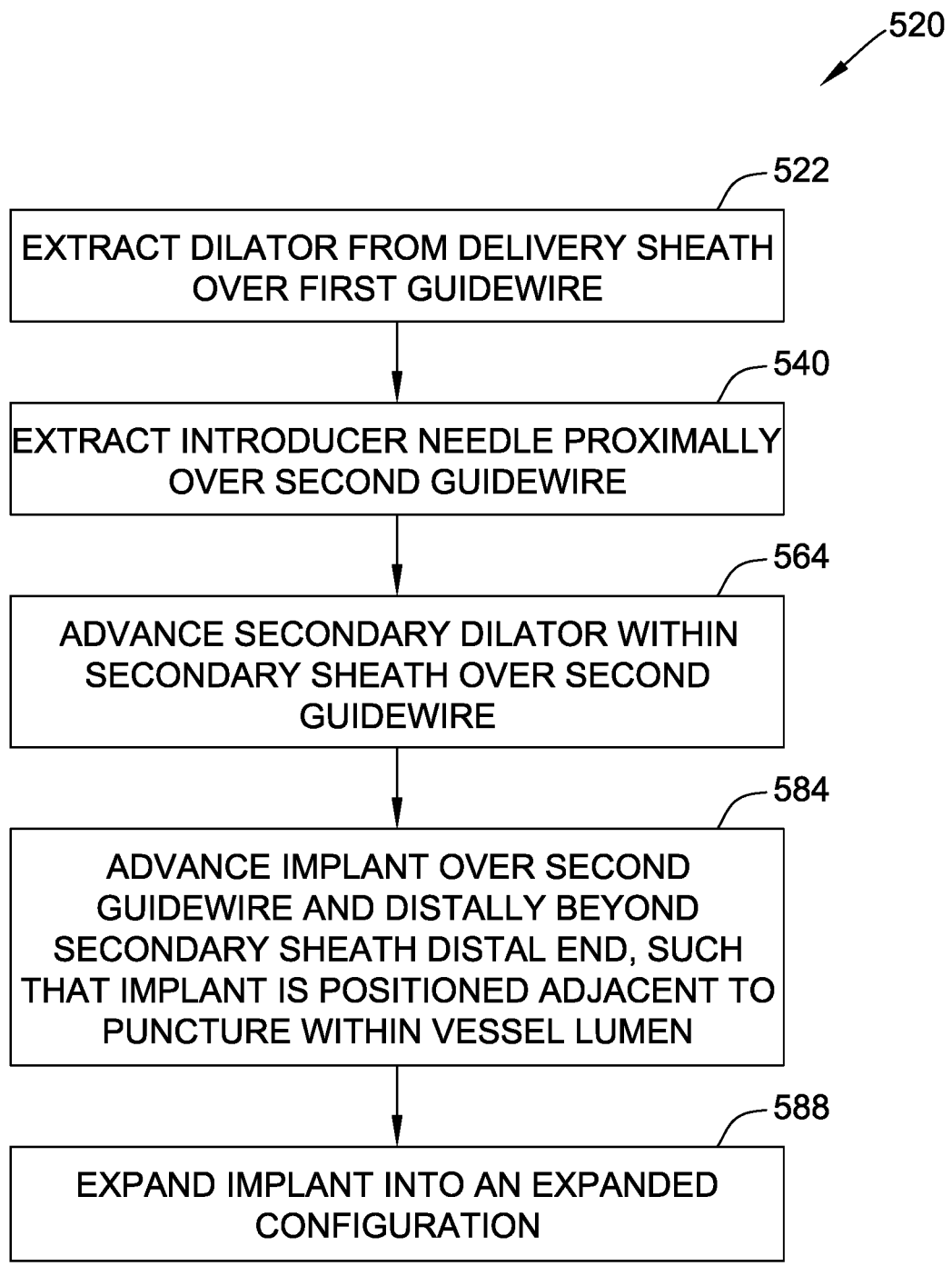
FIG. 5D is a flow diagram of a third exemplary embodiment of the step of the method shown in FIG. 5A.
Figure 12:
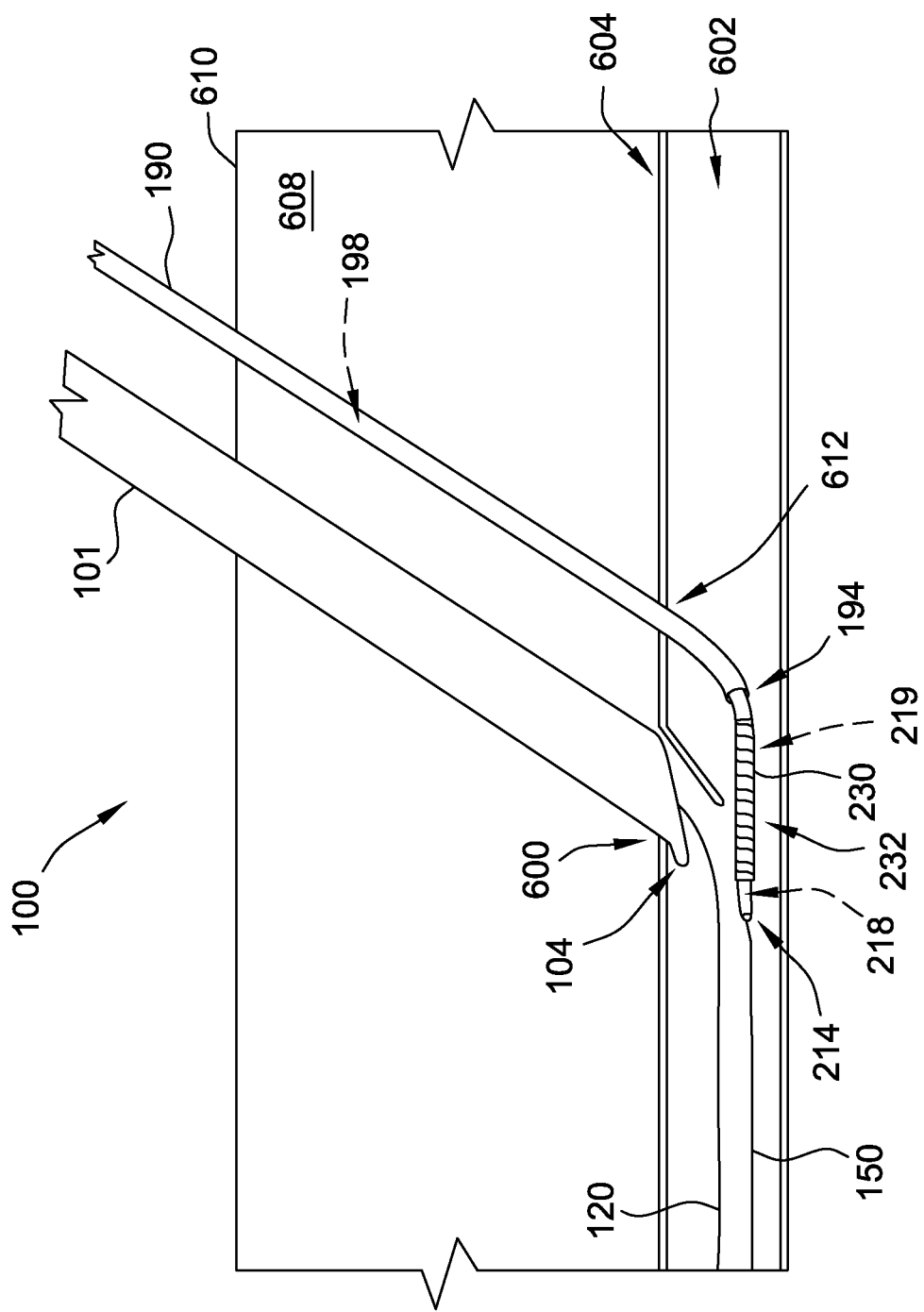
FIG. 12 illustrates a stage of the method of FIG. 5D.
Figure 13:
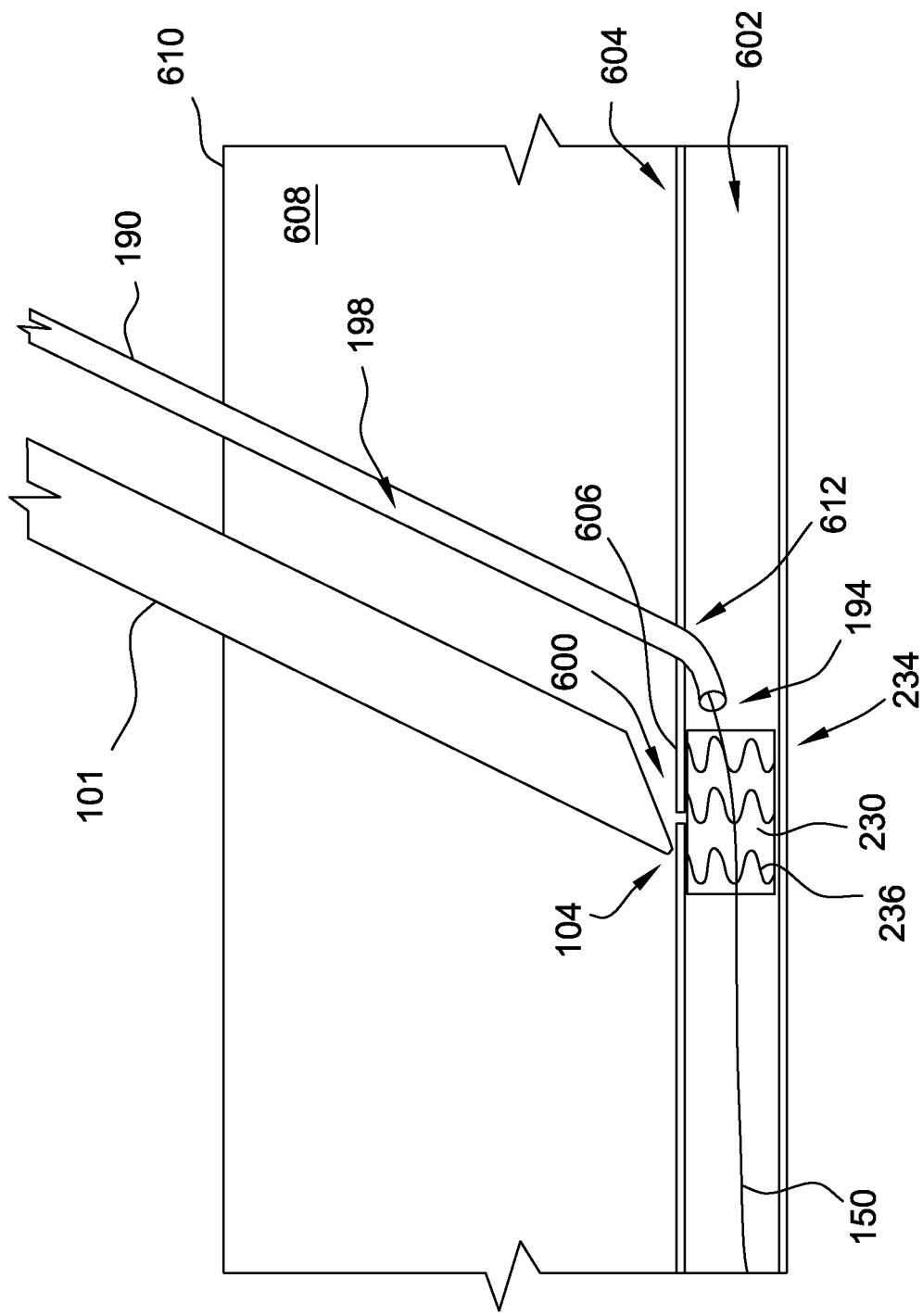
FIG. 13 illustrates another stage of the method of FIG. 5D.

FIG. 5D is a flow diagram of a third embodiment of step 520 of method 500, using second guidewire 150 to facilitate sealing of puncture 600. FIGS. 12 and 13 illustrate various further stages of the third embodiment of step 520. With reference to FIGS. 5A, 5D, 12, and 13, after delivery sheath distal end 104 is positioned 504 inside vessel lumen 602, as described above, dilator 110 is extracted 522 from delivery sheath 101 over first guidewire 120. In the illustrated embodiment, closure system 100 again includes secondary sheath 190 and secondary dilator 210 receivable at least partially through secondary sheath lumen 198, such that secondary dilator distal end 214 extends distally from secondary sheath distal end 194. Secondary dilator 210 again defines lumen 218 extending therethrough and configured to receive second guidewire 150 therethrough. Step 520 again includes extracting 540 introducer needle 140 proximally over second guidewire 150 and uncoupling introducer needle 140 from delivery sheath 101, and advancing 564 secondary dilator 210 received within secondary sheath 190 over second guidewire 150. In the exemplary embodiment, secondary dilator 210 is advanced such that secondary dilator distal end 214 extends distally beyond secondary sheath distal end 194 within vessel lumen 602.

In the illustrated embodiment, step 520 further includes advancing 584 an implant 230 over second guidewire 150, such that implant 230 is positioned adjacent to puncture 600 within vessel lumen 602. For example, implant 230 is coupled to secondary dilator 210 adjacent to secondary dilator distal end 214, and implant 230 is advanced 584 with secondary dilator 210 through secondary sheath 190 until implant 230 is positioned distally beyond secondary sheath distal end 194 and adjacent to puncture 600. In some embodiments, secondary sheath 190 has a diameter larger than 3 Fr, in contrast to the embodiment described with regard to FIGS. 10 and 11, to facilitate passage of implant 230 through secondary sheath lumen 198. For example, but not by way of limitation, secondary sheath 190 has a diameter of 5 Fr.

In some embodiments, implant 230 is advanced 584 in a contracted configuration 232 sized to pass through secondary sheath lumen 198. For example, in the exemplary embodiment, implant 230 is a bioabsorbable stent expandable from contracted configuration 232 by a balloon catheter. In alternative embodiments, implant 230 is any suitable implant that enables closure system 100 to function as described herein, for example a shape memory alloy implant.

In the illustrated embodiment, after implant 230 is positioned adjacent to puncture 600 within vessel lumen 602, implant 230 is expanded 588 into an expanded configuration 234, as shown in FIG. 13. Moreover, implant 230 is configured such that, after expansion 588 from contracted configuration 232, implant 230 independently retains expanded configuration 234. For example, in the exemplary embodiment, a balloon 219 on secondary dilator 210 is inflated to expand 588 implant 230, and implant 230 includes suitable ribs 236 that tend to lock into place in expanded configuration 234. Alternatively, implant 230 is expanded 588 in any suitable fashion that enables closure system 100 to function as described herein.

Because implant 230 is inserted from secondary access site 612 at offset 146 from puncture 600, implant 230 as initially positioned traverses substantially a full width of inferior flap 606, and thus expansion 588 of implant 230 elevates inferior flap 606 into a position proximate to puncture 600 as implant 230 approaches expanded configuration 234, as shown in FIG. 13. Thus, implant 230 in expanded configuration 234 facilitates at least partially sealing, and achieving hemostasis at, puncture 600.

In some embodiments, after implant 230 is expanded 588, a completion arteriogram is performed using secondary sheath 190 to verify adequate closure of puncture 600, as described above. The operator then extracts secondary sheath 190 from secondary access site 612, and manual pressure or another suitable method is applied to facilitate hemostasis at secondary access site 612.

Figures 17, 18:
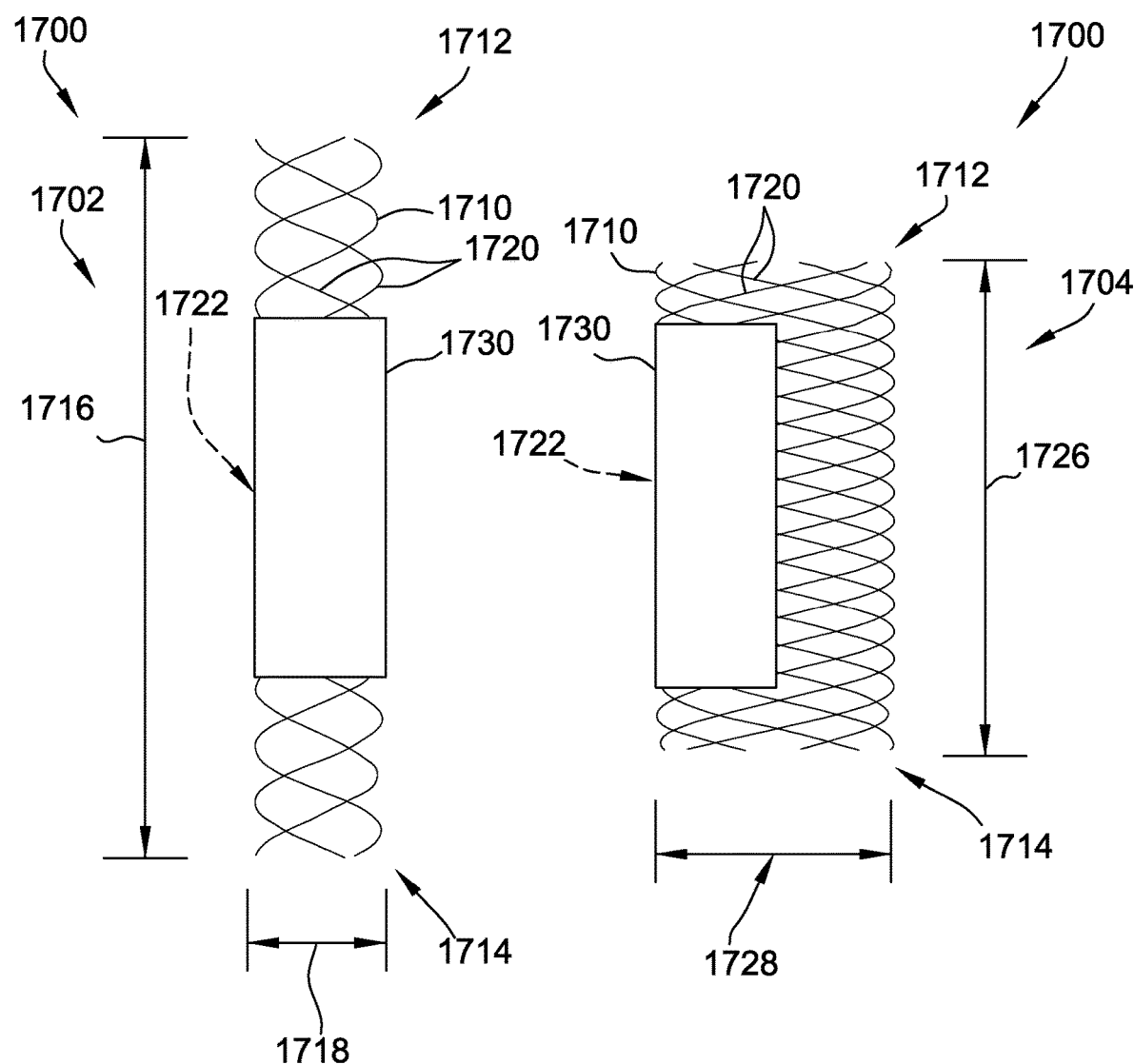
FIG. 17 is a schematic side view of an exemplary implant that may be used with the closure system shown in FIG. 1, showing the implant in a delivery configuration.
FIG. 18 is a schematic side view of the exemplary implant of FIG. 17, showing the implant in a deployed configuration.

FIG. 17 is a schematic side view of another exemplary implant 1700 that may be used with closure system 100, showing implant 1700 in a delivery configuration 1702. FIG. 18 is another schematic side view of implant 1700, showing implant 1700 in a deployed configuration 1704. Similar to implant 230 described above, implant 1700 is suitable for delivery into vessel lumen 602 in delivery configuration 1702 via secondary access site 612, and for subsequent expansion into deployed configuration 1704 adjacent puncture 600 to facilitate hemostasis at puncture 600. However, an expandability of implant 1700 and a deployment tool used to deliver and deploy implant 1700 differ in some respects from implant 230.

In the exemplary embodiment, implant 1700 includes a body 1710 and a cover 1730. In the exemplary embodiment, body 1710 and cover 1730 are each formed from suitable bioabsorbable materials such as, but not limited to, poly lactic acid (PLA), poly glycolic acid (PGA), or poly lactic-co-glycolic acid. In alternative embodiments, body 1710 and cover 1730 are each formed from any suitable materials that enable implant 1700 to function as described herein.

Body 1710 has a generally tubular shape that extends from a proximal end 1712 to a distal end 1714 and defines a longitudinal channel 1708 extending therethrough. Moreover, body 1710 is constructed such that implant 1700 in an unconstrained state assumes deployed configuration 1704, and is reversibly contractible to delivery configuration 1702 via application of a suitable constraining force. More specifically, body 1710 in delivery configuration 1702 has a delivery length 1716 from proximal end 1712 to distal end 1714, and a delivery diameter 1718, while body 1710 in deployed configuration 1704 has a deployed length 1726 from proximal end 1712 to distal end 1714, and a deployed diameter 1728. Deployed diameter 1728 is greater than delivery diameter 1718. In the exemplary embodiment, deployed diameter 1728 is selected to be equal to or slightly greater than the diameter of vessel lumen 602, such that implant 1700 in the unconstrained state expands to bear against the walls of vessel 604. In the exemplary embodiment, delivery length 1716 is greater than deployed length 1726. In alternative embodiments, delivery length 1716 is other than greater than deployed length 1726.

In the exemplary embodiment, body 1710 is formed from a plurality of braided wires 1720. In alternative embodiments, body 1710 is formed in any suitable fashion that enables implant 1700 to function as described herein. In the exemplary embodiment, body 1710 includes a radio-opaque marker band 1722 coupled to body 1710 to facilitate identifying an orientation of implant 1700 within vessel 604 using fluoroscopy. In alternative embodiments, body 1710 does not include marker band 1722.

In certain embodiments, cover 1730 facilitates protection of body 1710 during an initial compression of body 1710 from an unconstrained state in deployed configuration 1704 into delivery configuration 1702, and/or during loading of implant 1700 onto a delivery device, as will described below. In alternative embodiments, implant 1700 does not include cover 1730.

In the exemplary embodiment, cover 1730 is a flexibly curved sheet sized to extend around a circumference of body 1710 in delivery configuration 1702. In some embodiments, cover 1730 is sized to extend more than once around the circumference of body 1710, for example in a spiral-wound configuration, in delivery configuration 1702. In the exemplary embodiment, cover 1730 is coupled to body 1710 at a single location, such as via a single suture to one of wires 1720, to reduce interference of cover 1730 with an expansion of body 1710 from delivery configuration 1702 to deployed configuration 1704. In alternative embodiments, cover 1730 is coupled to body 1710 in any suitable fashion that enables implant 1700 to function as described herein. In the exemplary embodiment, cover 1730 is sized to extend less than once around the circumference of body 1710, for example to extend about half-way around the circumference of body 1710, in deployed configuration 1704. In alternative embodiments, cover 1730 is sized to extend around body 1710 to any suitable extent in deployed configuration 1704 that enables implant 1700 to function as described herein.

Figure 19:
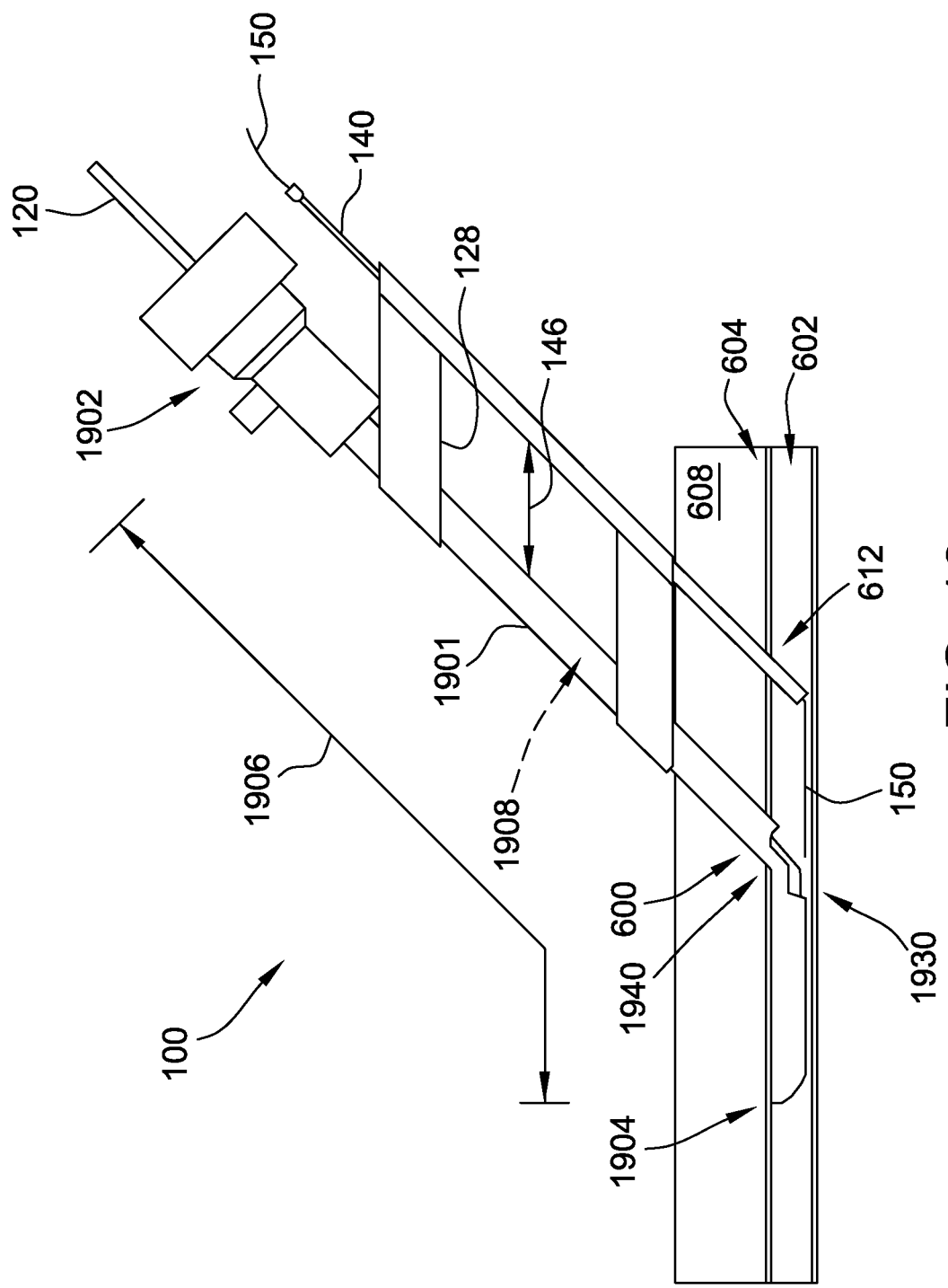
FIG. 19 is a schematic view of the exemplary closure system shown in FIG. 1, including an exemplary alternative embodiment of a delivery sheath.
Figure 20:
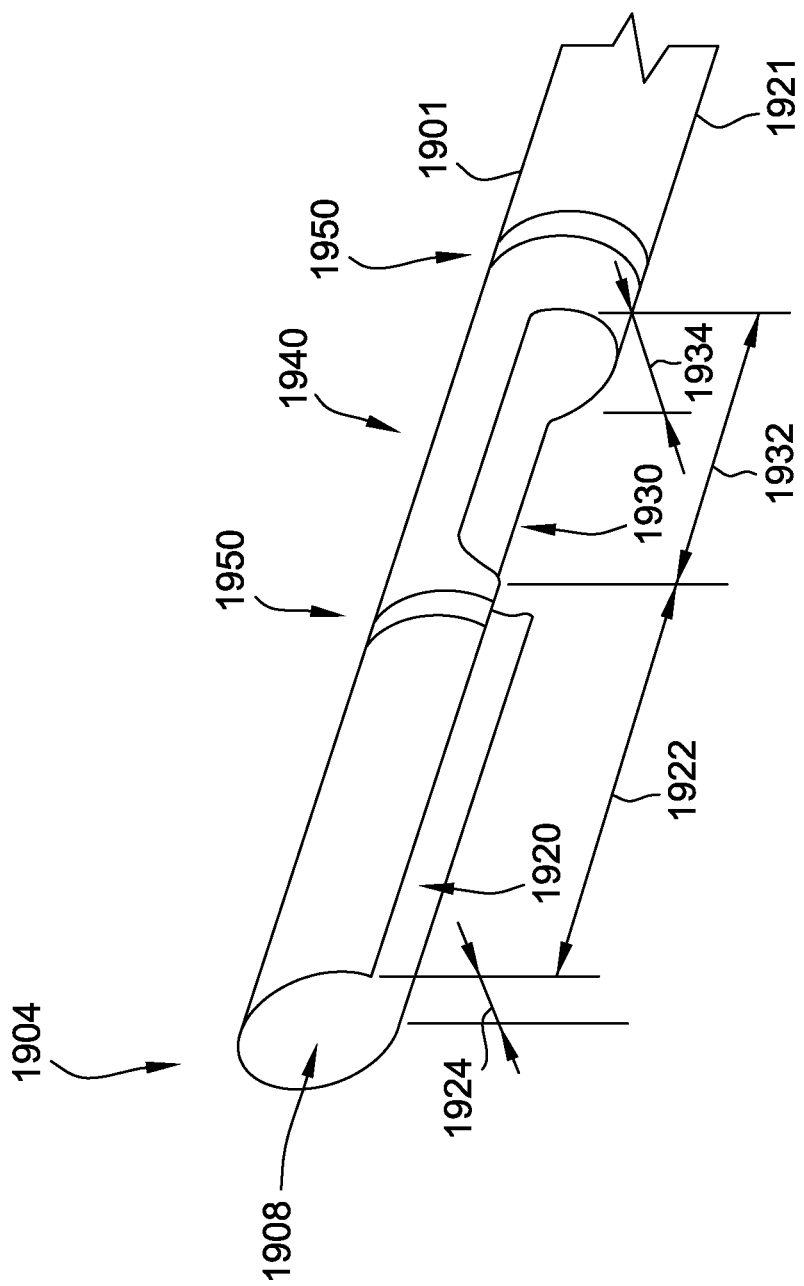
FIG. 20 is a perspective view of a distal portion of the delivery sheath shown in FIG. 19.

FIG. 19 is a schematic view of closure system 100 including an exemplary alternative embodiment of primary delivery sheath 101, designated primary delivery sheath 1901. FIG. 20 is a perspective view of a distal portion of delivery sheath 1901. Delivery sheath 1901 will be described herein as used in conjunction with deploying implant 1700 at puncture 600, as described with respect to FIG. 5E. However, in alternative embodiments, delivery sheath 101 implemented as delivery sheath 1901 is used in conjunction with deploying any of anchor 310, the at least one closure 228 including but not limited to using coupling device 1420, deploying implant 230, and any other suitable embodiment of the method described in FIG. 5A.

Delivery sheath 1901 extends longitudinally from a proximal end 1902 to a distal end 1904 and defines a length 1906 therebetween. In the exemplary embodiment, delivery sheath length 1906 is between about 10 centimeters and about 20 centimeters. In alternative embodiments, delivery sheath length 1906 is any suitable length that enables closure system 100 to function as described herein. In the exemplary embodiment, delivery sheath 1901 has a diameter in a range of 14 Fr to 24 Fr, such as for use in facilitating hemostasis at a large bore puncture. In alternative embodiments, delivery sheath 1901 has any suitable diameter that enables delivery sheath 1901 to function as described herein. Delivery sheath 1901 defines a lumen 1908 extending therethrough from proximal end 1902 to distal end 1904.

In the exemplary embodiment, delivery sheath 1901 is configured to cooperate with introducer needle 140, as discussed above. For example, introducer needle 140 is coupled to delivery sheath 1901, via an embodiment of bracket 128, at offset 146 relative to delivery sheath 1901. Introducer needle 140 is configured to receive second guidewire 150 therethrough such that second guidewire is receivable into vessel lumen 602 at secondary access site 612, also as discussed above.

In the exemplary embodiment, delivery sheath 1901 includes a distal slot 1920 defined therein and extending through a wall of delivery sheath 1901 from an exterior surface to an interior surface. More specifically, distal slot 1920 is defined in a posterior side 1921 of delivery sheath 1901 configured to face away from puncture 600 after insertion into vessel 604. Distal slot 1920 is configured to be positioned distal to puncture 600, to facilitate delivery sheath 1901 being withdrawn proximally from vessel lumen 602 without interfering with instruments inserted into vessel lumen 602 through secondary access site 612 and positioned adjacent to puncture 600.

More specifically, distal slot 1920 extends from distal end 1904 proximally over a distal slot length 1922. In the exemplary embodiment, distal slot length 1922 is in a range from about 3 centimeters to about 5 centimeters. In alternative embodiments, distal slot length 1922 is any suitable length that enables delivery sheath 1901 to function as described herein. In addition, distal slot 1920 extends circumferentially along posterior side 1921 of delivery sheath 1901 over a width 1924. In the exemplary embodiment, distal slot width 1924 is in a range from about 2 millimeters to about 3 millimeters. In alternative embodiments, distal slot width 1924 is any suitable width that enables delivery sheath 1901 to function as described herein.

In the exemplary embodiment, delivery sheath 1901 also includes a window 1930 defined therein and extending through a wall of delivery sheath 1901 from an exterior surface to an interior surface. More specifically, window 1930 is defined in posterior side 1921 of delivery sheath 1901 and opens from a proximal end of distal slot 1920. Window 1930 is configured to be positioned within vessel lumen 602 adjacent to and facing away from puncture 600, such that instruments inserted into vessel lumen 602 through secondary access site 612 are positionable adjacent to puncture 600, for example to move inferior flap 606 towards the wall of vessel 604 without obstruction by delivery sheath 1901, while delivery sheath 901 is still in place.

More specifically, window 1930 extends from distal slot 1920 proximally over a window length 1932. In the exemplary embodiment, window length 1932 is in a range from about 2 centimeters to about 3 centimeters. In alternative embodiments, window length 1932 is any suitable length that enables delivery sheath 1901 to function as described herein. In addition, window 1930 extends circumferentially along posterior side 1921 of delivery sheath 1901 over a width 1934. In the exemplary embodiment, window width 1934 is about half the circumference of delivery sheath 1901. In alternative embodiments, window width 1934 is any suitable width that enables delivery sheath 1901 to function as described herein.

Delivery sheath 1901 is configured to flex about a flex location 1940 from a straight configuration to an angled configuration to facilitate insertion of the distal portion of delivery sheath 1901 into vessel lumen 602. In the exemplary embodiment, flex location 1940 is located circumferentially opposite window 1930 to facilitate positioning window 1930 adjacent to puncture 600. In alternative embodiments, flex location 1940 is located at any suitable position along delivery sheath 1901 that enables delivery sheath 1901 to function as described herein. In the exemplary embodiment, delivery sheath 1901 is configured to flex to an angle in a range from about 45 degrees to about 60 degrees. In alternative embodiments, delivery sheath 1901 is configured to flex to any suitable angle that enables delivery sheath 1901 to function as described herein.

In the exemplary embodiment, delivery sheath 1901 further includes a pair of radio-opaque marking bands 1950 adjacent to the opposing proximal and distal sides of window 1930. Marking bands 1950 are observable under fluoroscopy to verify that window 1930 is positioned underneath puncture 600. In alternative embodiments, delivery sheath 1901 does not include marking bands 1950.

Figure 21:
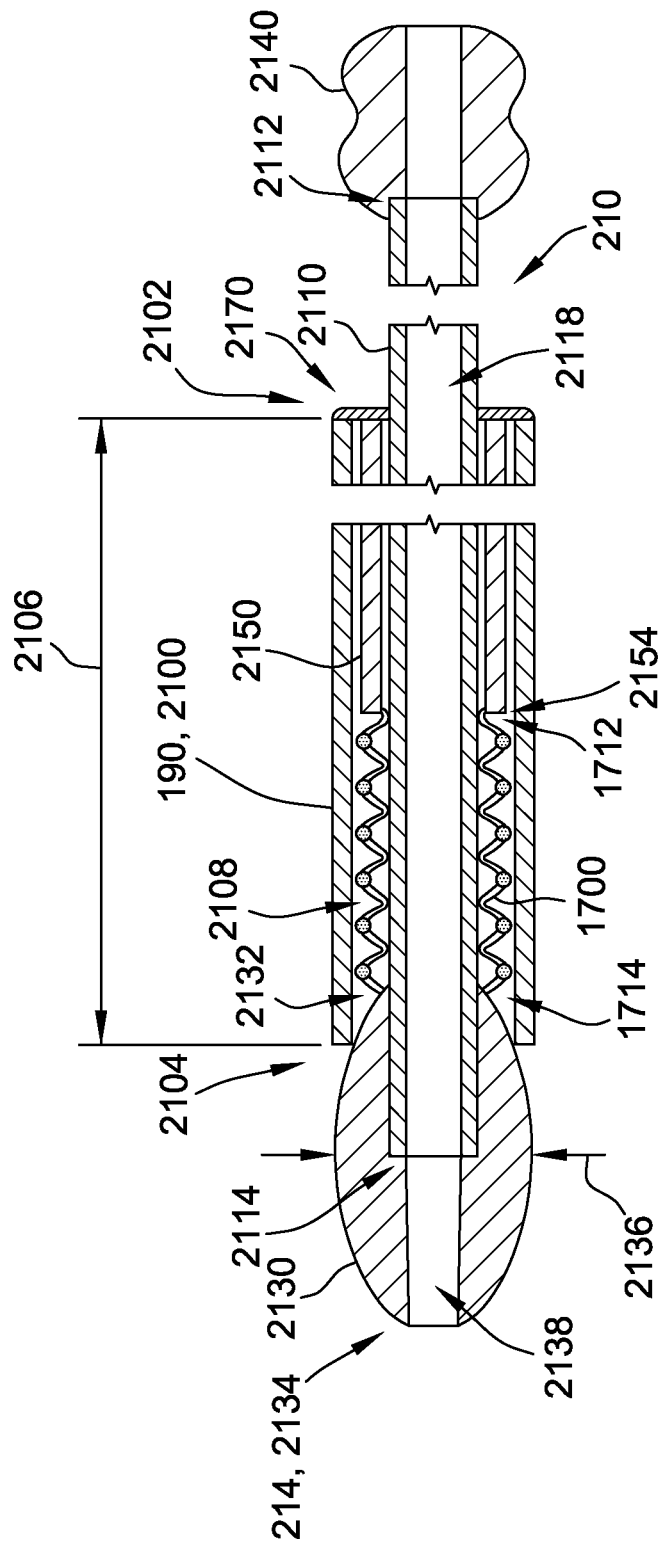
FIG. 21 is a schematic sectional view of an exemplary secondary sheath and exemplary secondary dilator that may be used with the closure system of FIG. 1 to deliver and deploy the implant shown in FIG. 17.

FIG. 21 is a schematic sectional view of an exemplary embodiment of another secondary sheath 190, designated as secondary sheath 2100, and secondary dilator 210 that may be used with closure system 100 to deliver and deploy implant 1700. Secondary sheath 2100 extends longitudinally from a proximal end 2102 to a distal end 2104 and defines a length 2106 therebetween. In the exemplary embodiment, secondary sheath length 2106 is between about 10 centimeters and about 20 centimeters. In alternative embodiments, secondary sheath length 2106 is any suitable length that enables closure system 100 to function as described herein. In the exemplary embodiment, secondary sheath 2101 has a diameter in a range of 5 Fr to 7 Fr, to facilitate positioning of implant 1700 therein. In alternative embodiments, secondary sheath 2101 has any suitable diameter that enables secondary sheath 2101 to function as described herein. Secondary sheath 2101 defines a lumen 2108 extending therethrough from proximal end 2102 to distal end 2104.

In the exemplary embodiment, closure system 100 also includes secondary dilator 210 embodied as a hypotube 2110. Hypotube 2110 extends longitudinally from a proximal end 2112 to a distal end 2114. Hypotube 2110 is receivable at least partially through secondary sheath lumen 2108, such that hypotube proximal end 2112 extends proximally from secondary sheath proximal end 2102. In the exemplary embodiment, hypotube 2110 is further sized such that hypotube distal end 2114 extends distally from secondary sheath distal end 2104 when hypotube proximal end 2112 extends proximally from secondary sheath proximal end 2102. In alternative embodiments, hypotube distal end 2114 is positioned relative to secondary sheath distal end 2104 in any suitable fashion that enables closure system 100 to function as described herein. Hypotube 2110 defines a hypotube lumen 2118 extending therethrough from proximal end 2112 to distal end 2114, and configured to receive second guidewire 150 (shown in FIG. 19) therethrough. For example, but not by way of limitation, hypotube lumen 2118 has a diameter of 0.051 centimeters to receive a second guidewire 150 having a diameter of 0.046 centimeters in a clearance fit.

In the exemplary embodiment, secondary dilator 210 also includes a tip element 2130 fixedly coupled to hypotube distal end 2114, such that a distal end 2134 of tip element 2130 defines secondary dilator distal end 214. Moreover, in the exemplary embodiment, tip element 2130 is shaped to facilitate smooth traversal of secondary sheath 2100 through subcutaneous tissue 608. For example, tip element 2130 has an olive shape that transitions smoothly from tip element distal end 2134 adjacent second guidewire 150, to a maximum diameter 2136 approximately equal to the diameter of secondary sheath 2100. In alternative embodiments, tip element 2130 has any suitable shape that enables closure system 100 to function as described herein. In other alternative embodiments, secondary dilator 210 does not include tip element 2130 and/or hypotube distal end 2114 defines secondary dilator distal end 214.

Tip element 2130 includes a tip element lumen 2138 defined therein and extending therethrough from a tip element proximal end 2132 to a tip element distal end 2134. More specifically, tip element lumen 2138 is in flow communication with hypotube lumen 2118 such that second guidewire 150 is receivable therethrough. In the exemplary embodiment, tip element lumen 2138 includes a distal portion having a diameter that matches the hypotube lumen diameter, and a proximal portion having a diameter sized to receive an outer diameter of hypotube 2110 in an interference fit, such that hypotube distal end 2114 is fixedly coupled to tip element 2130 and a distal end of hypotube lumen 2118 transitions smoothly into the distal portion of tip element lumen 2138. In alternative embodiments, tip element lumen 2138 is sized in any suitable fashion, and/or hypotube distal end 2114 is coupled to tip element 2130 in any suitable fashion, that enables closure system 100 to function as described herein.

With reference to FIGS. 17, 18, and 21, implant 1700 in delivery configuration 1702 is sized to be retained in secondary sheath lumen 2108. More specifically, hypotube 2110 is received through implant longitudinal channel 1708, such that implant 1700 is coupled to secondary dilator 210 and retained in an annular space in secondary sheath lumen 2108 defined radially outward from hypotube 2110. In the exemplary embodiment, an interior surface of secondary sheath 2100 couples against implant 1700 to facilitate retaining implant 1700 in delivery configuration 1702. In alternative embodiments, implant 1700 is retained in delivery configuration 1702 in any suitable fashion that enables closure system 100 to function as described herein.

In the exemplary embodiment, secondary sheath 2100 is positionable relative to secondary dilator 210 such that secondary sheath distal end 2104 abuts tip element proximal end 2132, as shown in FIG. 21. In addition, secondary sheath 2100 is movable proximally relative to hypotube 2110, such that implant 1700 is uncovered by, and located distal to, secondary sheath distal end 2104. In the exemplary embodiment, secondary dilator 210 includes a handle 2140 fixedly coupled to hypotube proximal end 2112, such that secondary sheath 2100 is movable proximally relative to secondary dilator 210 by holding handle 2140 steady and sliding secondary sheath 2100 proximally. In alternative embodiments, secondary dilator 210 does not include handle 2140 and/or secondary sheath 2100 is movable proximally relative to secondary dilator 210 in any suitable fashion that enables closure system 100 to function as described herein.

In the exemplary embodiment, a suitable valve 2170 is coupled to secondary sheath proximal end 2102 to facilitate sealing secondary sheath lumen 2108 while permitting relative longitudinal movement with respect to secondary dilator 210 extending therethrough.

In the exemplary embodiment, implant 1700 is positioned longitudinally within secondary sheath lumen 2108 such that implant distal end 1714 is positioned adjacent to secondary dilator distal end 214. For example, implant 1700 is positioned adjacent to tip element proximal end 2132. Thus, implant 1700 is covered within secondary sheath lumen 2108 when secondary sheath distal end 2104 abuts tip element proximal end 2132, such as during insertion of secondary sheath 2100 through subcutaneous tissue 608 into vessel lumen 602. In addition, implant 1700 is in an uncovered position distal to secondary sheath distal end 2104 after secondary sheath 2100 is moved proximally relative to hypotube 2110. In alternative embodiments, implant 1700 is positioned longitudinally within secondary sheath lumen 2108, and/or is coverable/uncoverable, in any suitable fashion that enables closure system 100 to function as described herein.

In the exemplary embodiment, secondary dilator 210 further includes a spacer tube 2150 positionable within secondary sheath lumen 2108 proximally from implant 1700. Spacer tube 2150 facilitates maintaining a longitudinal position of implant 1700 in delivery configuration 1702. More specifically, spacer tube 2150 is positioned in the annular space in secondary sheath lumen 2108 defined radially outward from hypotube 2110, such that a distal end 2154 of spacer tube 2150 abuts proximal end 1712 of implant 1700 and inhibits movement of implant 1700 in the proximal direction. In the exemplary embodiment, spacer tube 2150 is coupled to hypotube 2110 for movement with hypotube 2110 and handle 2140, such that spacer tube 2150 facilitates maintaining implant 1700 adjacent to tip element 2130 as secondary sheath 2100 is withdrawn proximally over implant 1700 and hypotube 2110. In alternative embodiments, secondary dilator 210 does not include spacer tube 2150 and/or implant 1700 is maintained adjacent to tip element 2130 in any suitable fashion as secondary sheath 2100 is withdrawn proximally over implant 1700 and hypotube 2110.

Figure 5E:
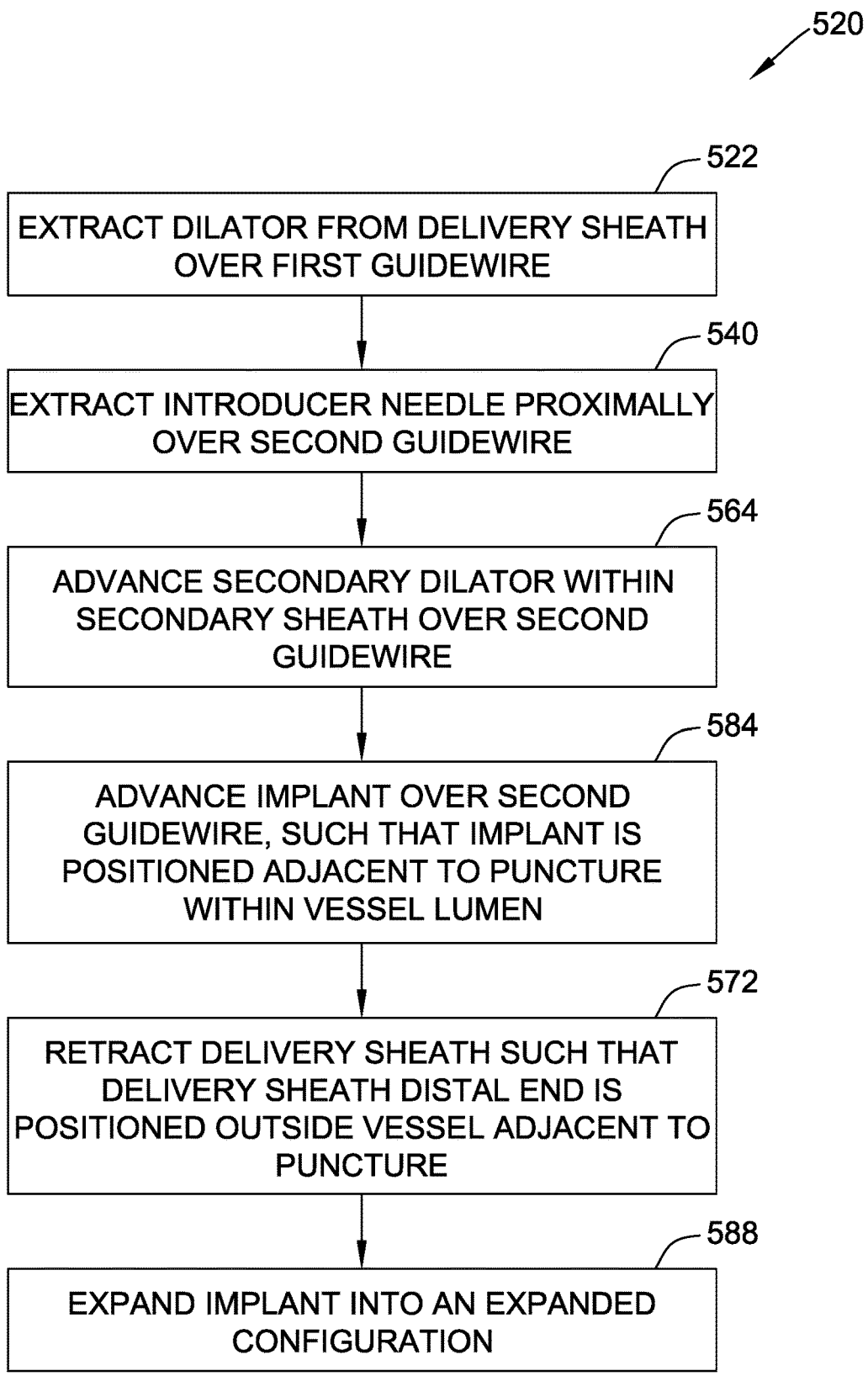
FIG. 5E is a flow diagram of a fourth exemplary embodiment of the step of the method shown in FIG. 5A.
Figure 22:
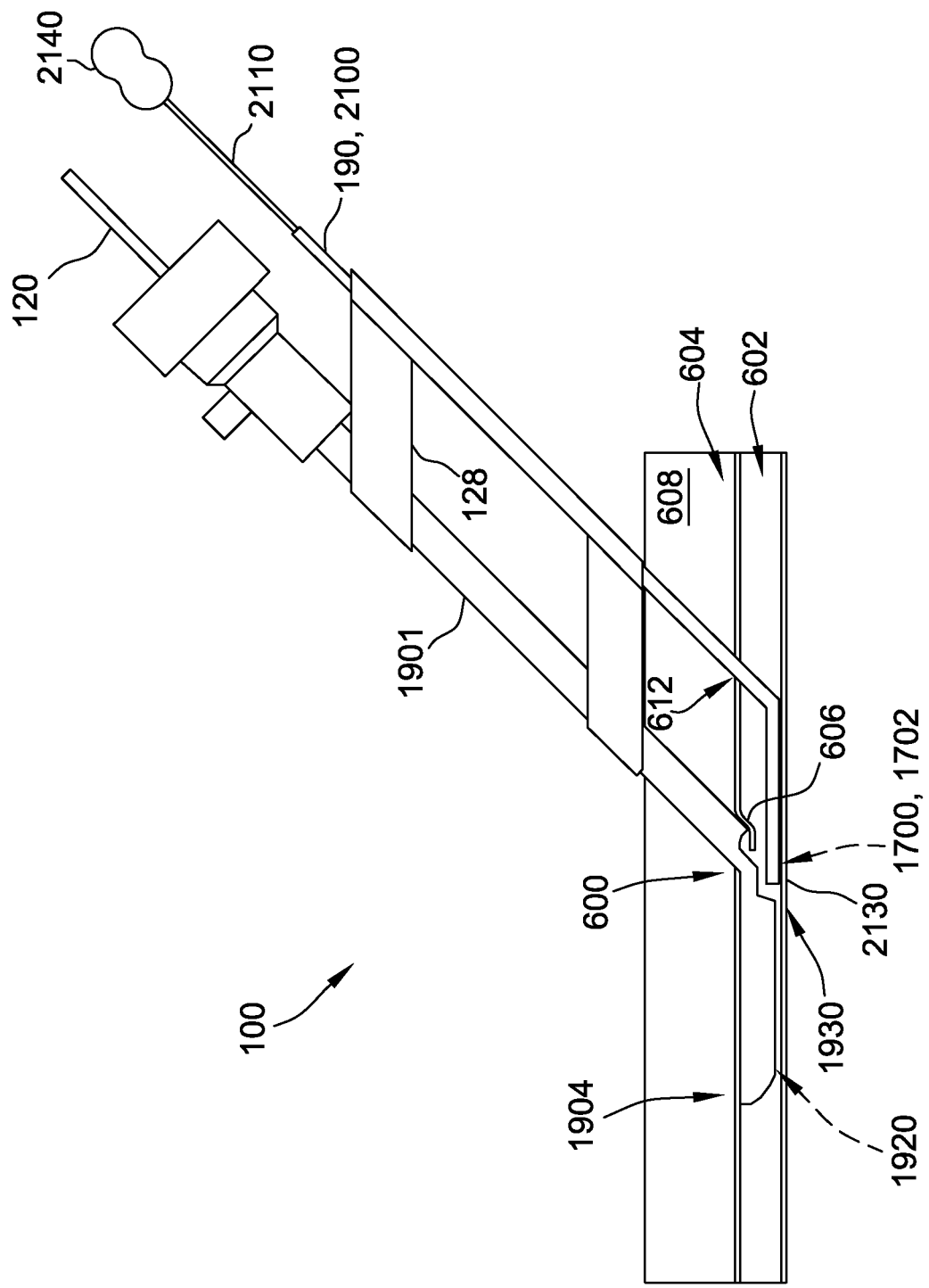
FIG. 22 illustrates a stage of the method of FIG. 5E.
Figure 23:
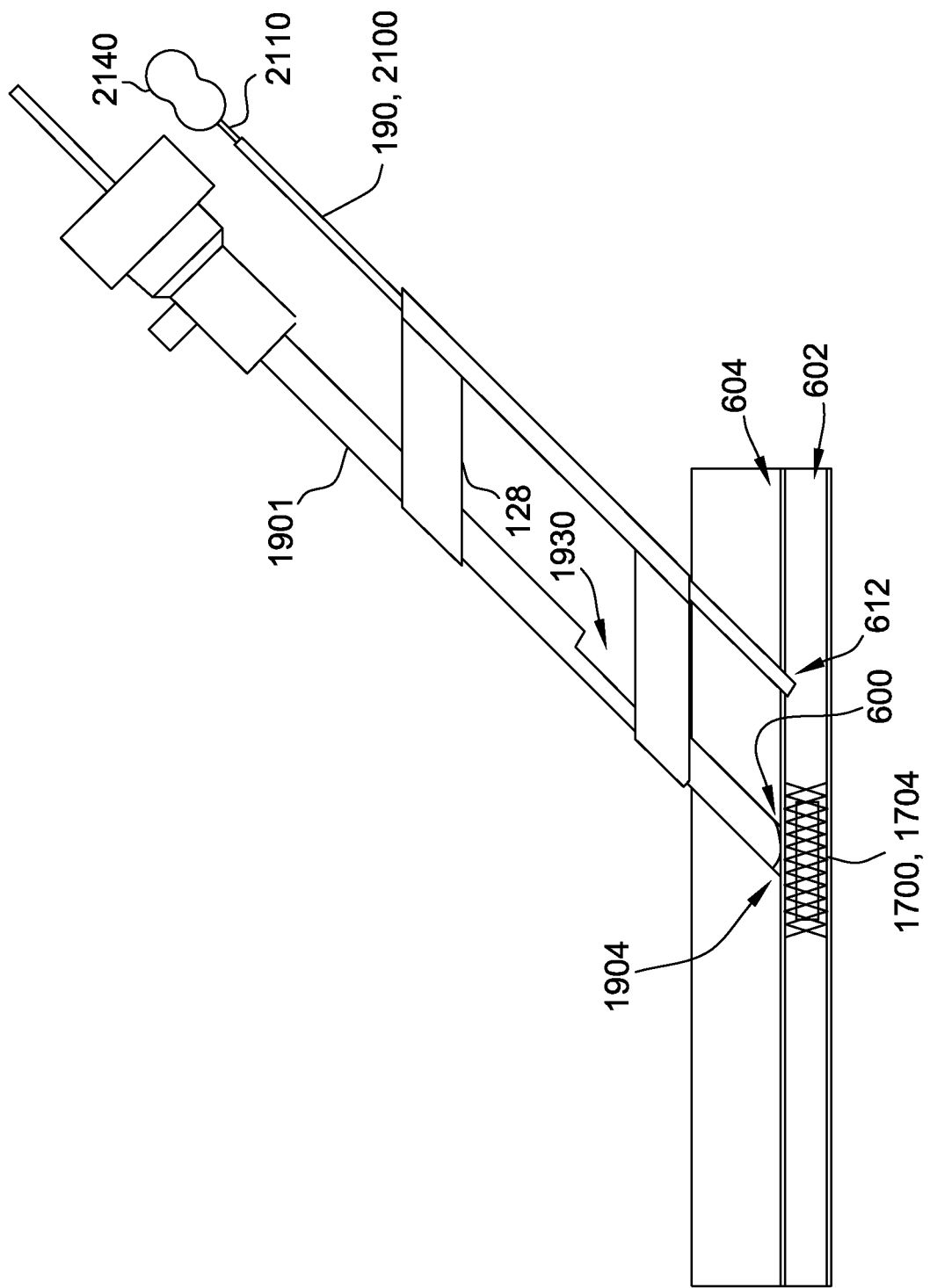
FIG. 23 illustrates another stage of the method of FIG. 5E.

FIG. 5E is a flow diagram of a fourth embodiment of step 520 of method 500, using second guidewire 150 to facilitate sealing of puncture 600. FIGS. 22 and 23 illustrate various further stages of the fourth embodiment of step 520. With reference to FIGS. 5A, 5E, and 17-23, after delivery sheath distal end 1904 is positioned 504 inside vessel lumen 602, as described above, and before step 520 is performed, delivery sheath distal end 1904 is advanced 506 further inside vessel lumen 602, such that window 1930 is positioned within vessel lumen 602 underneath puncture 600. In some embodiments, positioning of window 1930 is observed and/or verified by observing marking bands 1950 under fluoroscopy.

Step 520 again includes extracting 522 dilator 110 from delivery sheath 101 over first guidewire 120, and extracting 540 introducer needle 140 proximally over second guidewire 150 and uncoupling introducer needle 140 from delivery sheath 101. In the exemplary embodiment, step 520 also again includes advancing 564 secondary dilator 210 received within secondary sheath 190, 2100 over second guidewire 150. Moreover, implant 1700, coupled to distal end 2114 of secondary dilator 210, is again advanced 584 over second guidewire 150 such that implant 1700 is positioned within vessel lumen 602 adjacent to puncture 600, as shown in FIG. 22. In the exemplary embodiment, implant 1700 is in delivery configuration 1702 and covered by distal end 2104 of secondary sheath 2100 during step 584. In certain embodiments, window 1930 of delivery sheath 1901 reduces interference with delivery sheath 1901 during positioning of implant 1700. In some embodiments, positioning of implant 1700 is observed and/or verified by observing marker band 1722 of body 1710 under fluoroscopy.

The operator next retracts 572 delivery sheath 1901 over first guidewire 120 such that delivery sheath distal end 1904 is positioned outside vessel 604 adjacent to puncture 600. In the exemplary embodiment, distal slot 1920 and window 1930 of delivery sheath 1901 facilitate delivery sheath 1901 being withdrawn proximally from vessel lumen 602 without interfering with distal end 214 of secondary dilator 210 traversing beneath puncture 600.

Next, implant 1700 is expanded 588 to deployed configuration 1704, which is sized to bear against the walls of vessel 604, as discussed above and shown in FIG. 23. In the exemplary embodiment, to expand 588 implant 1700, the operator moves secondary sheath 2100 proximally relative to secondary dilator 210, such that implant 1700 is uncovered. For example, the operator holds handle 2140 steady while sliding secondary sheath 2100 proximally to uncover implant 1700. As implant 1700 is uncovered, implant 1700 in the unconstrained state expands to deployed configuration 1704. In the exemplary embodiment, spacer tube 2150 fixedly coupled to hypotube 2110 facilitates maintaining the longitudinal position of implant 1700 underneath puncture 600 while secondary sheath 2100 is retracted, e.g., facilitates preventing implant 1700 from being dragged proximally by secondary sheath 2100 during retraction of secondary sheath 2100.

Moreover, due to the positioning of implant 1700 to traverse underneath puncture 600, implant 1700 elevates inferior flap 606 as implant 1700 expands to deployed configuration 1704, facilitating hemostasis at puncture 600. In some embodiments, secondary sheath 2100 includes a side port (not shown) adjacent to proximal end 2102 to facilitate injection of a suitable material for performing a completion arteriogram to verify adequate closure of puncture 600. First guidewire 120 is then removed proximally. Secondary dilator 210, including in the exemplary embodiment hypotube 2110, tip element 2130, and spacer tube 2150, along with second guidewire 150, are then removed proximally from secondary access site 612. In some embodiments, hemostasis at secondary access site 612 is controlled with manual pressure on skin 610.

Figure 24:
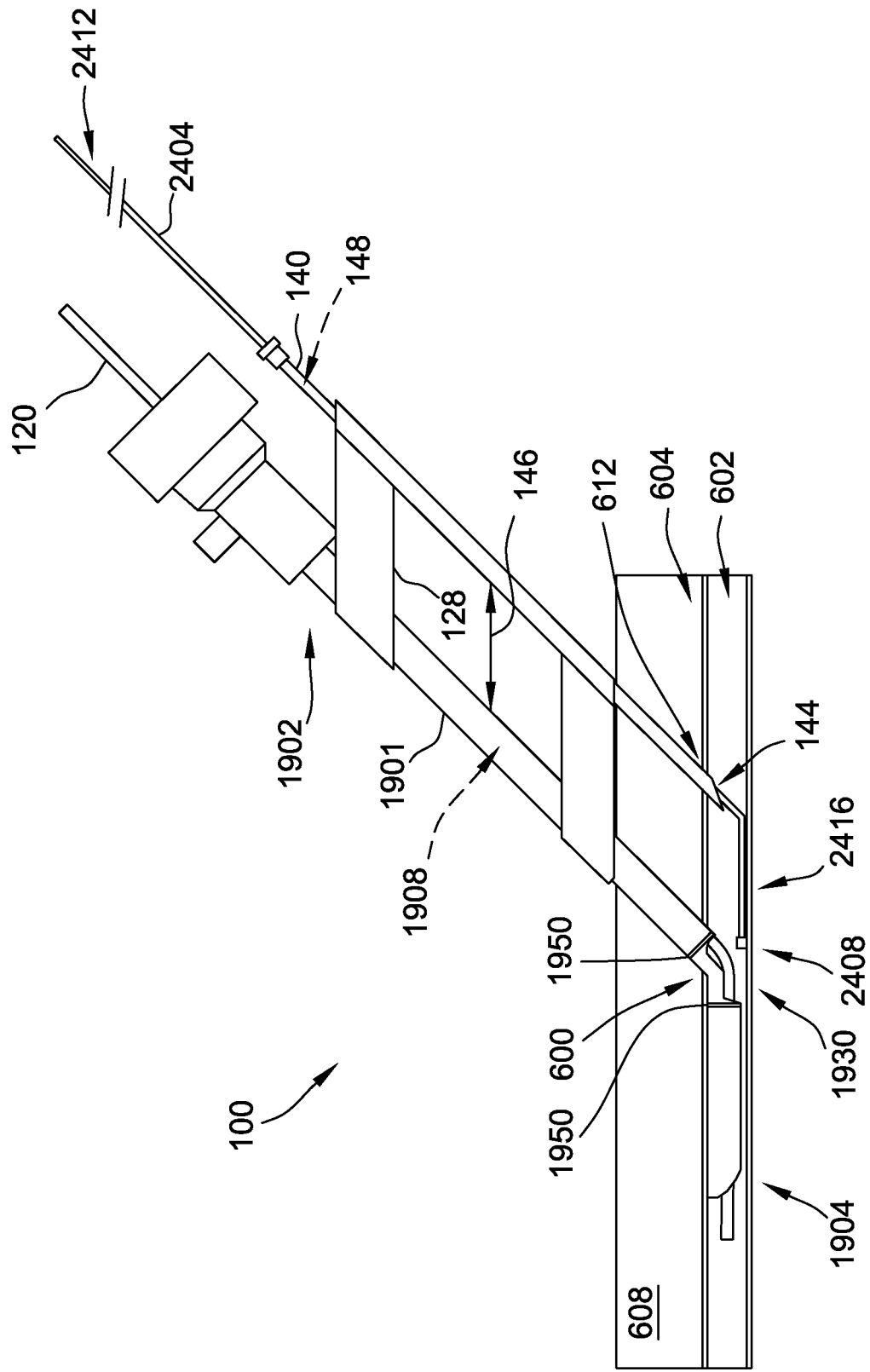
FIG. 24 is a schematic view of the closure system shown in FIG. 1, including the delivery sheath shown in FIG. 19 and an exemplary alternative embodiment of a second guidewire.

FIG. 24 is a schematic view of closure system 100, including delivery sheath 1901 and an exemplary alternative embodiment of second guidewire 150, designated second guidewire 2404. Second guidewire 2404 extends between a proximal end 2412 and a distal end 2416. In the exemplary embodiment, second guidewire 2404 includes a guidewire magnet 2408 adjacent to distal end 2146 that is configured to magnetically couple to a complementary magnetic element, as will be described below, while positioned inside vessel lumen 602. In the illustrated embodiment, second guidewire 2404 is inserted through introducer needle lumen 148, and advanced through secondary access site 612 into vessel lumen 602 such that second guidewire 2404 traverses puncture 600 within vessel lumen 602, and such that guidewire magnet 2408 is positioned proximate to window 1930 of delivery sheath 1901. More specifically, second guidewire 2404 traverses puncture 600 such that guidewire magnet 2408 is in position to magnetically cooperate with a complementary magnetic element advanced through delivery sheath lumen 1908 proximate to window 1930.

Figure 25:
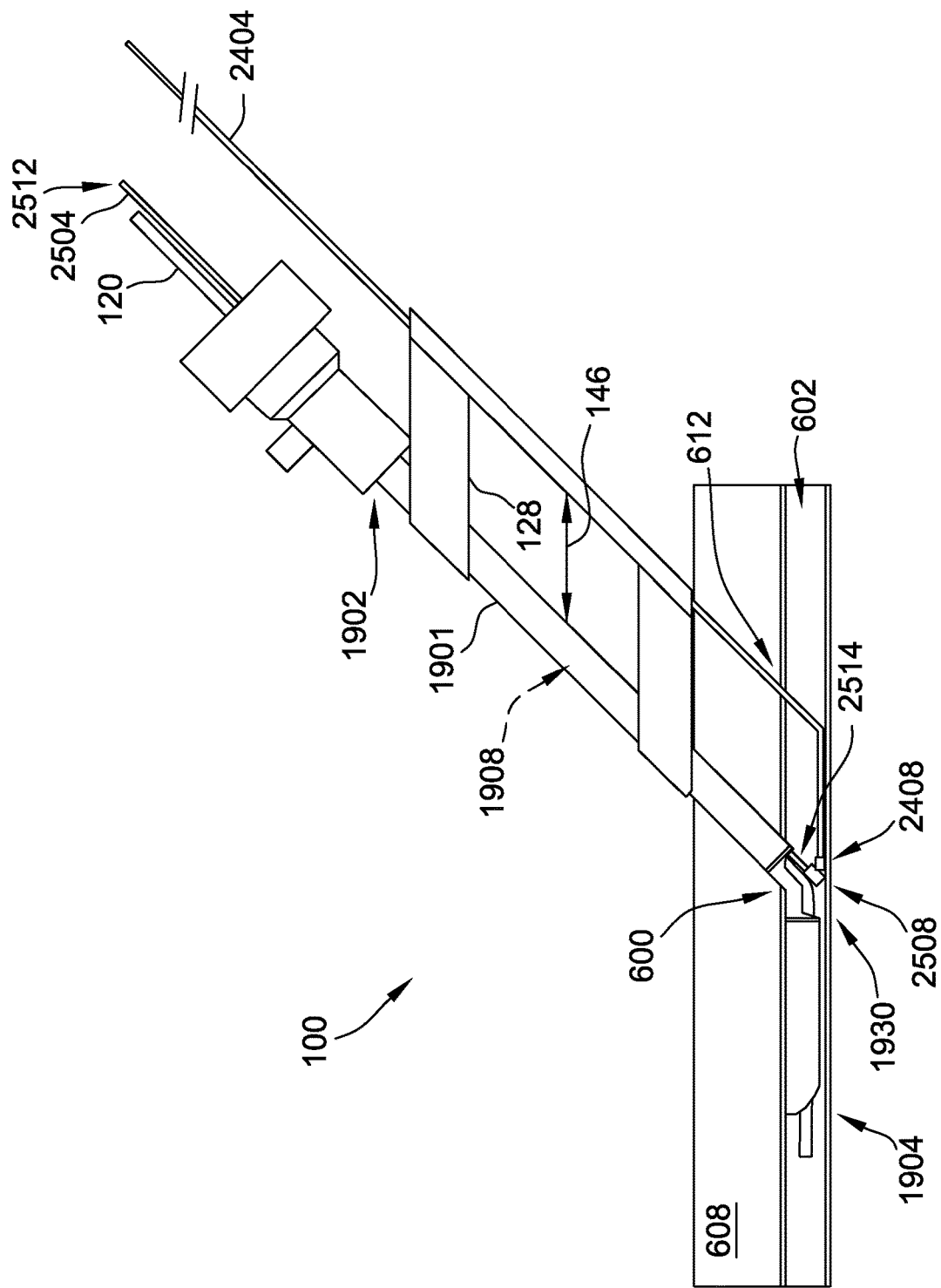
FIG. 25 is a schematic view of the closure system shown in FIG. 24 including an exemplary embodiment of a stylet.

FIG. 25 is a schematic view of closure system 100, including second guidewire 2404 and an exemplary embodiment of a stylet 2504. Stylet 2504 extends longitudinally from a proximal end 2512 to a distal end 2514. Stylet 2504 includes a stylet magnet 2508 configured to magnetically couple with guidewire magnet 2408. More specifically, stylet 2504 is receivable at least partially through delivery sheath lumen 1908, adjacent to first guidewire 120, such that stylet magnet 2508 is positioned proximate to window 1930 and in position to magnetically cooperate with complementary guidewire magnet 2408 positioned in vessel lumen 602 proximate to window 1930.

In the exemplary embodiment, stylet 2504 is sized such that stylet proximal end 2512 extends proximally from delivery sheath proximal end 1902 when stylet magnet 2508 is positioned proximate to window 1930. In alternative embodiments, stylet proximal end 2512 is positioned relative to delivery sheath proximal end 1902 in any suitable fashion that enables closure system 100 to function as described herein. In the exemplary embodiment, stylet magnet 2508 is coupled adjacent to distal end 2414 of stylet 2504. In alternative embodiments, stylet magnet 2508 is coupled to stylet 2504 at any suitable location that enables closure system 100 to function as described herein.

Figure 26:
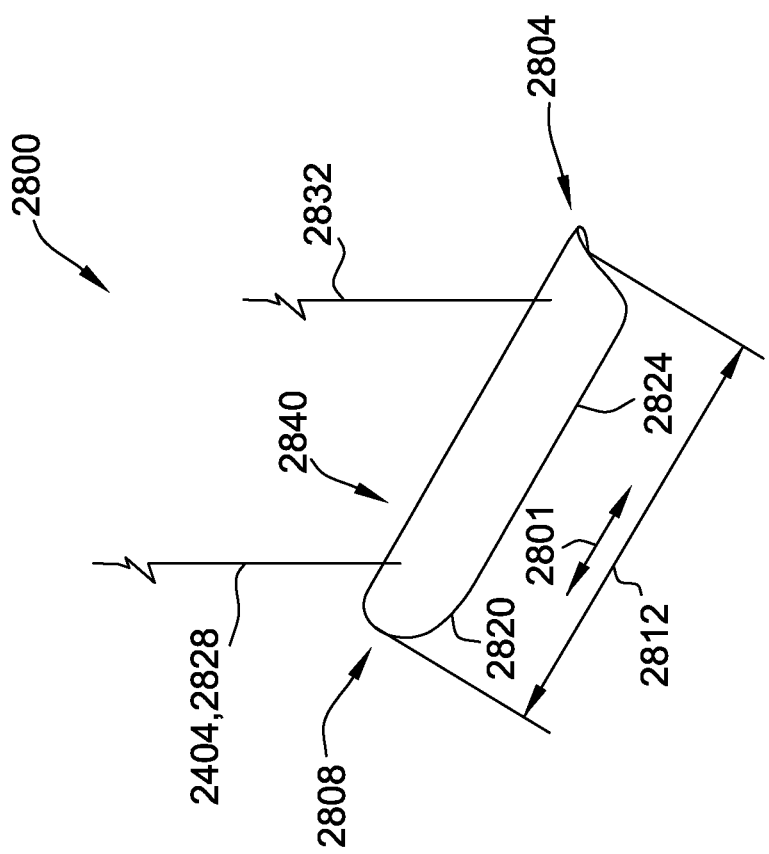
FIG. 26 is a schematic view of another exemplary implant that may be used with the closure system shown in FIGS. 24 and 25.
Figure 27:
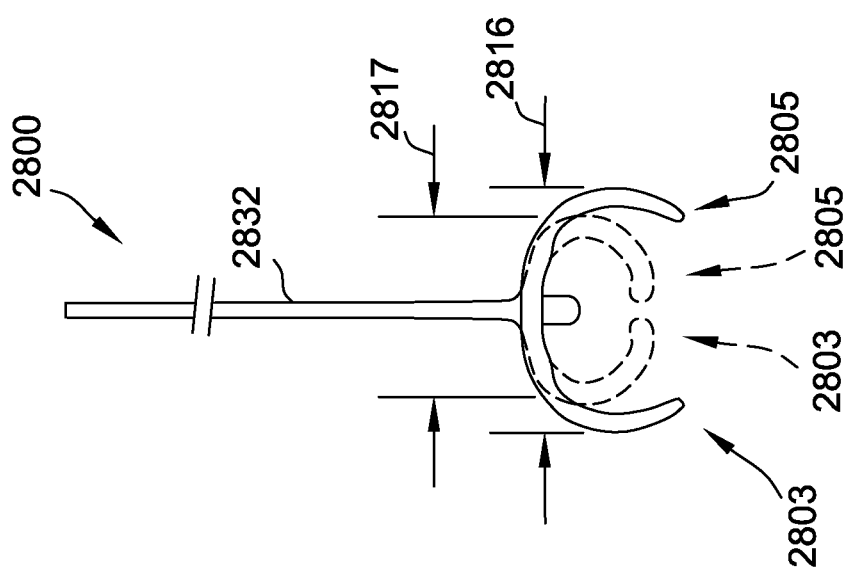
FIG. 27 is a schematic end view of the implant shown in FIG. 26, illustrating two flexibly curved configurations of the implant.

FIG. 26 is a schematic view of another exemplary implant 2800 that may be used with the closure system shown in FIGS. 24 and 25. FIG. 27 is a schematic end view of implant 2800, illustrating two flexibly curved configurations of implant 2800. With reference to FIGS. 26 and 27, implant 2800 includes a body 2840 that extends from a proximal end 2804 to a distal end 2808 and defines a length 2812 therebetween. Body 2840 is elongated in a direction 2801 parallel to length 2812. In the exemplary embodiment, length 2812 is sized such that after delivery of implant 2800, body 2840 extends from secondary access site 612 to a location in vessel lumen 602 distal of puncture 600, such that implant 2800 traverses puncture 600 within vessel lumen 602. For example, but not by way of limitation, length 2812 is about 3 centimeters. In alternative embodiments, length 2812 is any suitable length that enables implant 2800 to function as described herein.

In the exemplary embodiment, body 2840 is a plate having a flexible curvature about an axis parallel to elongation direction 2801. More specifically, a curvature of body 2840 is flexibly transitionable between a deployed configuration, having a deployed width 2816, and a delivery configuration (shown in dashed lines in FIG. 27), having a delivery width 2817 that is less than deployed width 2816. A cross-sectional perimeter of body 2840 extends along body 2840, in a plane normal to elongation direction 2801, from a first edge 2803 to a second edge 2805. Deployed width 2816 is sized to enable the cross-sectional perimeter of body 2840 to conform to an interior circumference of the wall of vessel 604, and delivery width 2817 is sized to enable the cross-sectional perimeter of body 2840 to be retained within a secondary sheath 2904 (shown in FIG. 30). In the exemplary embodiment, first edge 2803 and second edge 2805 in the delivery configuration are positioned in close proximity to each other, while first edge 2803 and second edge 2805 in the deployed configuration are relatively separated from each other. In alternative embodiments, first edge 2803 overlaps second edge 2805 in the delivery configuration, such that body 2840 is rolled upon itself. In other alternative embodiments, first edge 2803 and second edge 2805 in the delivery configuration are positioned relative to each other in any suitable fashion that enables implant 2800 to function as described herein.

In the exemplary embodiment, the cross-sectional perimeter of body 2840 in the deployed configuration is sized to couple against approximately 180 degrees of an inner circumference of vessel lumen 602. In alternative embodiments, the cross-sectional perimeter of body 2840 in the deployed configuration is sized to couple against any suitable portion of the circumference of vessel lumen 602 that enables implant 2800 to function as described herein.

In some embodiments, the cross-sectional perimeter of body 2840 in the deployed configuration varies along elongation direction 2801. For example, body 2840 includes a first portion 2820 and a second portion 2824 each having a different cross-sectional perimeter in the deployed configuration, such that body 2840 is generally pear-shaped. In some such embodiments, the cross-sectional perimeter of first portion 2820 in the deployed configuration is sized to couple against approximately 180 degrees of the inner circumference of vessel lumen 602, while the cross-sectional perimeter of second portion 2824 is sized to couple against approximately 120 degrees of the inner circumference of the vessel lumen 602. Implant 2800 is deployed such that wider first portion 2820 is positioned underneath puncture 600 and elevates inferior flap 606 (shown in FIG. 31), and narrower second portion 2824 is positioned adjacent secondary access site 612 to seal the relatively smaller secondary access site 612. In alternative embodiments, the cross-sectional perimeter of body 2840 in the deployed configuration varies along elongation direction 2801 in any suitable fashion that enables implant 2800 to function as described herein. In other alternative embodiments, the cross-sectional perimeter of body 2840 in the deployed configuration is substantially invariant along elongation direction 2801.

In the exemplary embodiment, body 2840 is formed to have an unforced, or free, width greater than deployed width 2816. In other words, a compressive force is required to transition body 2840 from the unforced configuration to the deployed configuration, and a further compressive force is required to transition body 2840 from the deployed configuration to the delivery configuration. Moreover, body 2840 is biased to spring back from the delivery configuration, and from the deployed configuration, towards the unforced configuration. Therefore, as will be described herein, when implant 2800 in the delivery configuration is released from secondary sheath 2904 (shown in FIG. 30) within vessel lumen 602, body 2840 expands until body 2840 couples against the interior of the wall of vessel 604. The wall of vessel 604 retains body 2840 in the deployed configuration. Because body 2840 in the deployed configuration remains biased outward towards the unforced configuration, the biasing, or springback, force tends to secure the deployed implant 2800 in position against the wall of vessel 604. In alternative embodiments, body 2840 is formed to have an unforced width approximately equal to deployed width 2816, such that body 2840 is biased to spring back from the delivery configuration to the deployed configuration. In other alternative embodiments, body 2840 has any suitable unforced width that enables implant 2800 to function as described herein.

In the exemplary embodiment, implant 2800 also includes a first anchor suture 2828 attached adjacent to distal end 2808 of body 2840, and a second anchor suture 2832 attached to proximal end 2804 of body 2840. As will be described herein, first and second anchor sutures 2828, 2832 further facilitate securing the deployed implant 2800 in position against the wall of vessel 604. First anchor suture 2828 is constrained to move proximally with second guidewire 2404. In the exemplary embodiment, a mid-portion of second guidewire 2404 is coupleable directly to body 2840 and defines first anchor suture 2828. In alternative embodiments, first anchor suture 2828 is a separate element configured for fixed coupling to second guidewire 2404.

In alternative embodiments, implant 2800 does not include first and second anchor sutures 2828, 2832.

In the exemplary embodiment, body 2840 is formed from suitable bioabsorbable materials such as, but not limited to, poly lactic acid (PLA), poly glycolic acid (PGA), or poly lactic-co-glycolic acid, and first and second anchor sutures 2828, 2832 are bioadsorbable sutures. In alternative embodiments, body 2840 and/or first and second anchor sutures 2828, 2832 are formed from any suitable materials that enable implant 2800 to function as described herein.

Figure 5F:
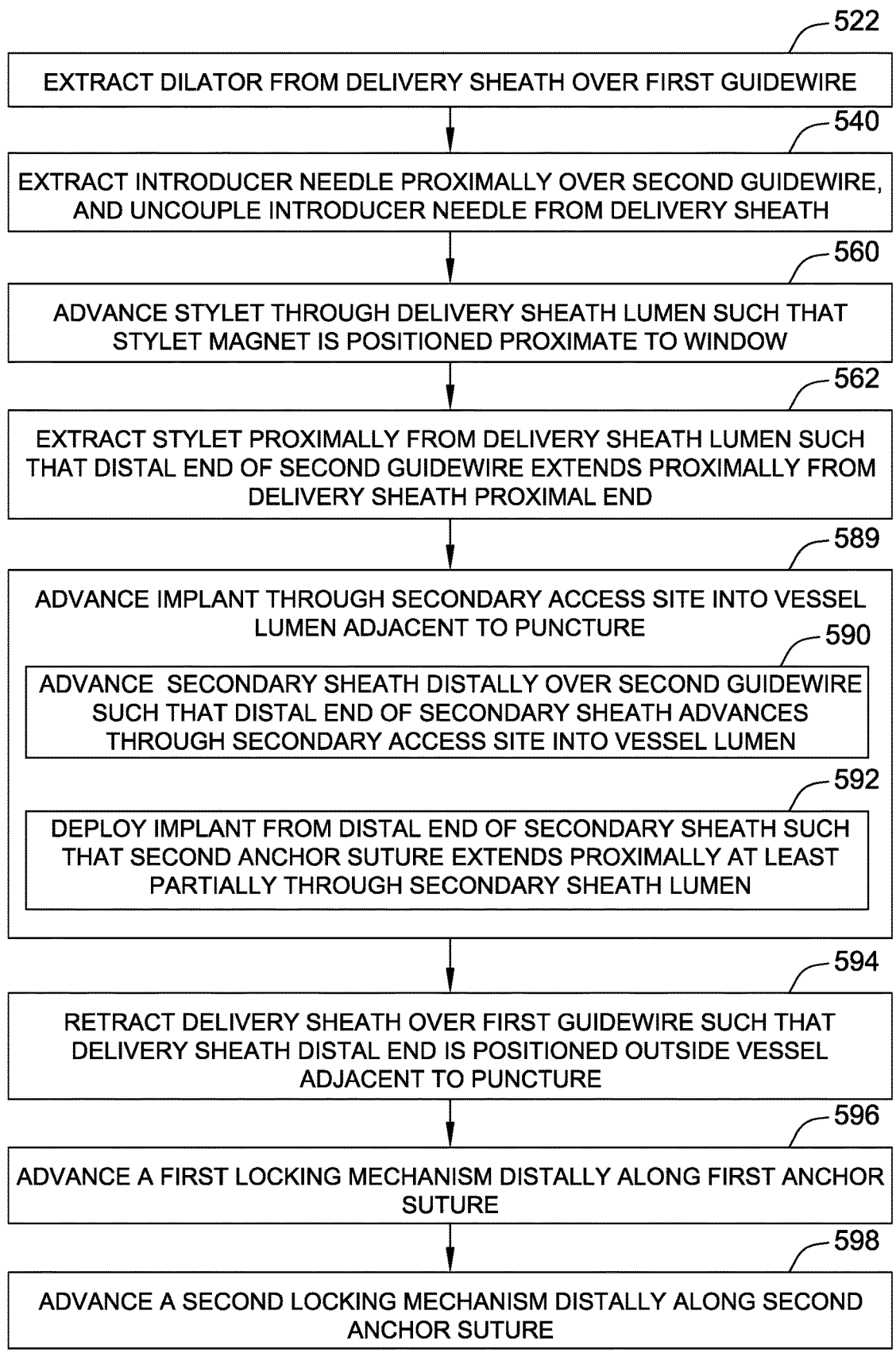
FIG. 5F is a flow diagram of a fifth exemplary embodiment of the step of the method shown in FIG. 5A.

FIG. 5F is a flow diagram of a fifth embodiment of step 520 of method 500 (shown in FIG. 5A), using second guidewire 150 to facilitate sealing of puncture 600. FIGS. 28-32 illustrate various further stages of the fifth embodiment of step 520. With reference to FIGS. 5A, 5F, and 24-32, after delivery sheath distal end 1904 is positioned 504 inside vessel lumen 602, as described above, and before step 520 is performed, delivery sheath distal end 1904 is advanced further inside vessel lumen 602, such that window 1930 is positioned within vessel lumen 602 underneath puncture 600. In some embodiments, positioning of window 1930 is observed and/or verified by observing marking bands 1950 under fluoroscopy. Moreover, step 516 is implemented by advancing second guidewire 150, embodied as second guidewire 2404, through secondary access site 612 such that guidewire magnet 2408 is positioned proximate to window 1930, as described above. In some embodiments, second guidewire is advanced 516 through introducer needle lumen 148, as described above. In other embodiments, a third guidewire (not shown) similar to first guidewire 120 is initially advanced through introducer needle 140 into vessel lumen 602, secondary dilator 210 (shown in FIG. 10) and secondary sheath 2904 are advanced over the third guidewire distally through secondary access site 612 into vessel lumen 602, dilator 210 and the third guidewire are then removed, and second guidewire 2404 is advanced 516 through secondary sheath 2904 and through secondary access site 612.

Figure 28:
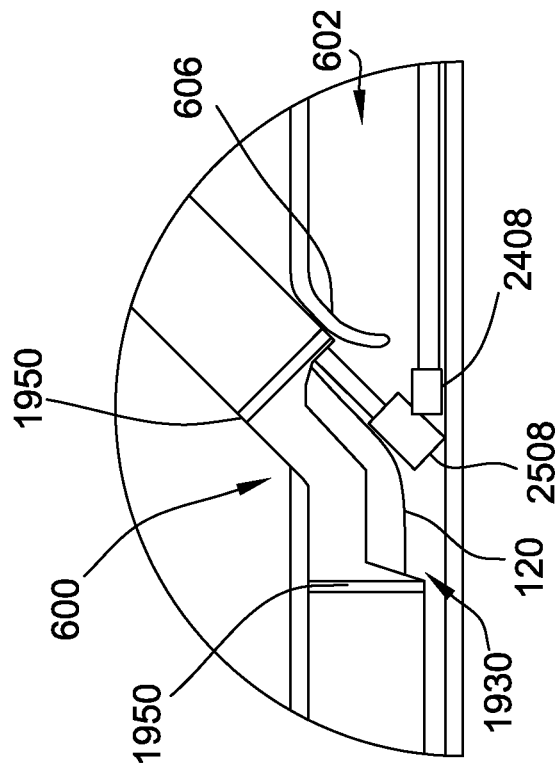
FIG. 28 illustrates a stage of the method of FIG. 5F.

Step 520 again includes extracting 522 dilator 110 from delivery sheath 101 over first guidewire 120, and, in some embodiments, extracting 540 introducer needle 140 proximally over second guidewire 150 and uncoupling introducer needle 140 from delivery sheath 101. In the exemplary embodiment, step 520 also includes advancing 560 stylet 2504 through delivery sheath lumen 1908, adjacent to first guidewire 120, such that stylet magnet 2508 is positioned proximate to window 1930 and in position to magnetically cooperate with complementary guidewire magnet 2408. More specifically, stylet 2504 is advanced 560 such that guidewire magnet 2408 and stylet magnet 2508 couple together within vessel lumen 602, as shown in FIG. 28.

Figure 29:
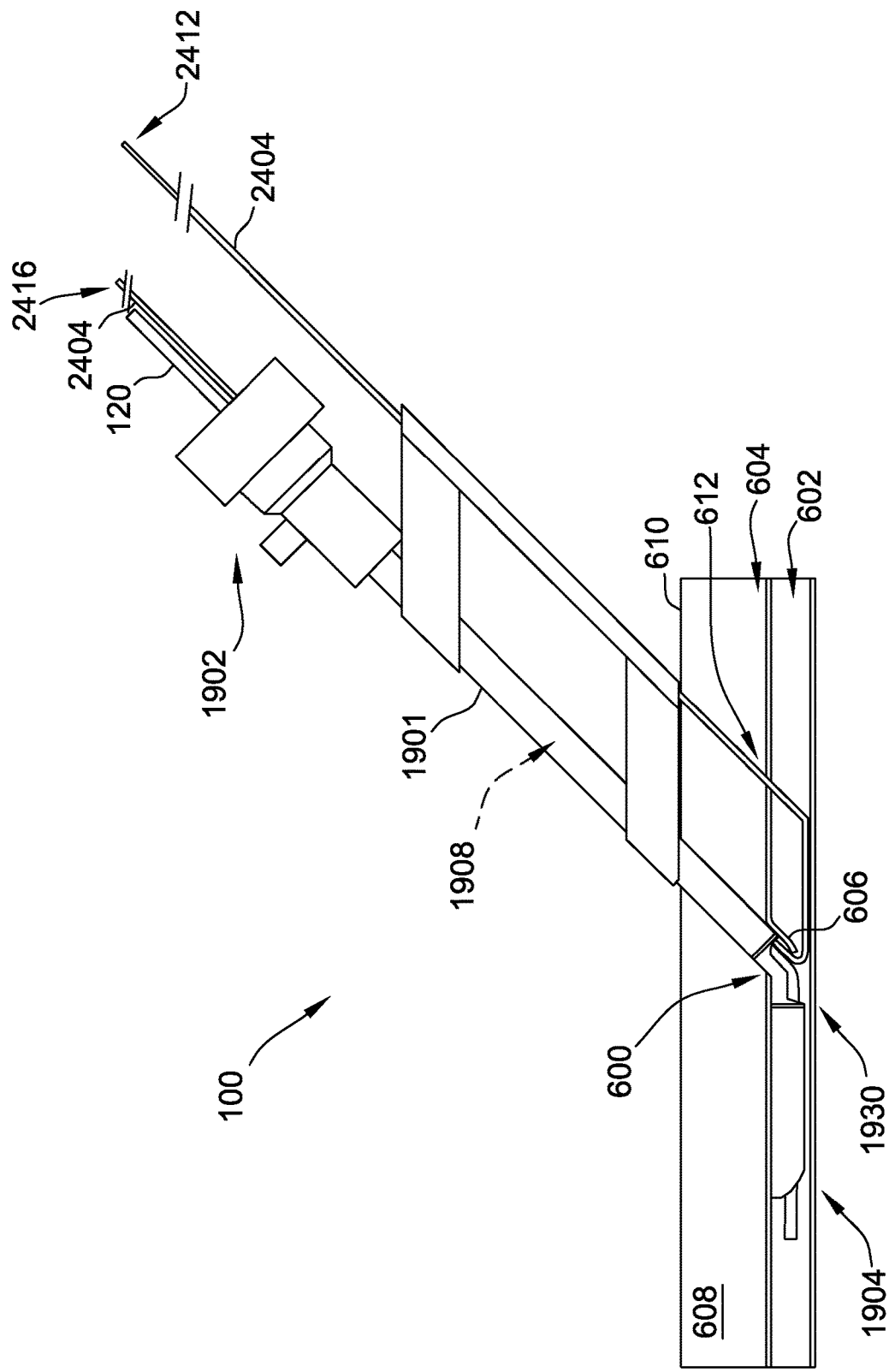
FIG. 29 illustrates another stage of the method of FIG. 5F.

Step 520 also includes extracting 562 stylet 2504 proximally from delivery sheath lumen 1908, such that distal end 2416 of second guidewire 2404 extends proximally from delivery sheath proximal end 1902, as shown in FIG. 29. More specifically, extracting 562 stylet 2504 draws guidewire magnet 2408 coupled to stylet magnet 2508 proximally through delivery sheath lumen 1908, such that distal end 2416 of second guidewire 2404 extends proximally from delivery sheath proximal end 1902. After stylet 2504 is extracted 562, second guidewire 2404 extends from proximal end 2412, distally through skin 610, subcutaneous tissue 608, and secondary access site 612 into vessel lumen 602, traverses puncture 600 beneath inferior flap 606, and extends proximally through window 1930, delivery sheath lumen 1908 adjacent to first guidewire 120, and out of delivery sheath proximal end 1902, as shown in FIG. 29. In some embodiments, a portion of second guidewire 2404 defines first anchor suture 2828 of implant 2800, as described above, such that first anchor suture 2828 is pulled proximally in step 562 and extends at least partially through delivery sheath lumen 1908. In other embodiments, first anchor suture 2828 is a separate element fixedly coupled to second guidewire 2404 at any suitable point in the method, for example one of (i) before guidewire magnet 2408 magnetically couples to stylet magnet 2508, (ii) after guidewire magnet 2408 magnetically couples to stylet magnet 2508 and before stylet 2504 is extracted 562, and (iii) after stylet 2504 is extracted 562. In such embodiments, after attachment of first anchor suture 2828, second guidewire 2404 is pulled proximally such that first anchor suture 2828 advances through window 1930 and extends at least partially through delivery sheath lumen 1908.

Figure 30:
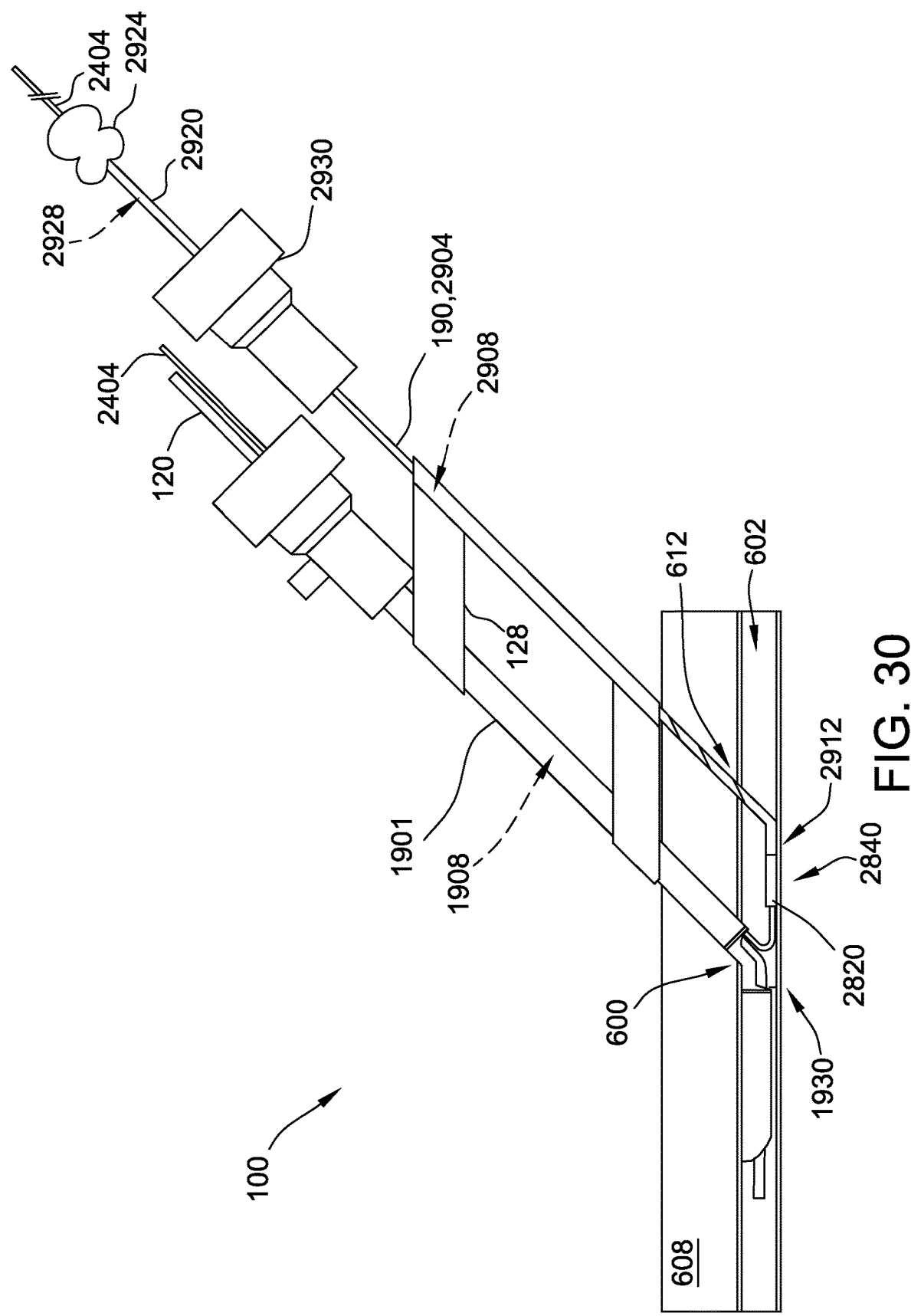
FIG. 30 illustrates another stage of the method of FIG. 5F.

Step 520 further includes advancing 589 implant 2800 through secondary access site 612 into vessel lumen 602 adjacent to puncture 600. As described above, first anchor suture 2828 of implant 2800 is coupled to body 2840 and is constrained to move proximally with second guidewire 2404. In the exemplary embodiment, step 589 includes advancing 590 another embodiment of secondary sheath 190, designated as secondary sheath 2904, distally over second guidewire 2404 such that a distal end 2912 of secondary sheath 2904 advances through secondary access site 612 into vessel lumen 602, as shown in FIG. 30. In the exemplary embodiment, secondary sheath 2904 is selectively coupleable to delivery sheath 1900, such as via bracket 128, for movement with respect to delivery sheath 1900. For example, but not by way of limitation, secondary dilator 210 (shown in FIG. 10) received within secondary sheath 2904 is advanced over second guidewire 2404 through secondary access site 612, and secondary dilator 210 is then extracted proximally from secondary sheath 2904, leaving distal end 2912 positioned within vessel lumen 602. In some embodiments, secondary sheath distal end 2912 includes a radio-opaque marker (not shown), similar to one of radio-opaque marking bands 1950 (shown in FIG. 20), that enables an operator to verify the positioning of secondary sheath distal end 2912 by observing the radio-opaque marker under fluoroscopy.

Secondary sheath 2904 is configured to retain implant 2800 in the delivery configuration within secondary sheath lumen 2908, as described above, such that implant 2800 is arranged circumferentially about second guidewire 2404. In some embodiments, implant 2800 is loaded into secondary sheath lumen 2908 at proximal end 2916 of secondary sheath 2904, either before or after secondary sheath 2904 is advanced into secondary access site 612, and implant 2800 is advanced through secondary sheath lumen 2908 towards distal end 2912 and through secondary access site 612. In other embodiments, implant 2800 is loaded into secondary sheath lumen 2908 at distal end 2912 of secondary sheath 2904 before secondary sheath 2904 is advanced into secondary access site 612. In alternative embodiments, implant 2800 is loaded into secondary sheath lumen 2908 and/or advanced through secondary access site 612 in any suitable fashion that enables implant 2800 to function as described herein.

In the exemplary embodiment, step 589 additionally includes deploying 592 implant 2800 from distal end 2912 of secondary sheath 2904, as shown in FIG. 30, such that second anchor suture 2832 extends proximally at least partially through secondary sheath lumen 2908. For example, closure system 100 includes a pusher tube 2920 insertable through a proximal end 2916 of secondary sheath 2904 into secondary sheath lumen 2908. In the exemplary embodiment, pusher tube 2920 defines a pusher tube lumen 2928 therein configured to receive second guidewire 2404 therethrough. Pusher tube 2920 is configured to advance along second guidewire 2404 within secondary sheath lumen 2908 and to move implant 2800 in the delivery configuration distally through secondary sheath lumen 2908 and out of distal end 2912.

In some embodiments, step 592 includes advancing first portion 2820 of body 2840 of implant 2800 out of distal end 2912 by holding secondary sheath 2904 steady and advancing pusher tube 2920 distally, and then advancing second portion 2824 of body 2840 out of distal end 2912 by holding pusher tube 2920 and retracting secondary sheath 2904 proximally such that distal end 2912 is positioned outside the wall of vessel 604. In the illustrated embodiment, pusher tube 2920 includes a handle 2924 (similar to handle 2140 shown in FIG. 21) fixedly coupled to a proximal end of pusher tube 2920, such that secondary sheath 2904 is proximally movable relative to pusher tube 2920 by holding handle 2924 steady, and sliding secondary sheath 2904 proximally. In alternative embodiments, pusher tube 2920 does not include handle 2924 and/or secondary sheath 2904 is proximally movable relative to pusher tube 2920 in any suitable fashion that enables closure system 100 to function as described herein. In other alternative embodiments, implant 2800 is deployed 592 from distal end 2912 of secondary sheath 2904 in any suitable fashion that enables implant 2800 to function as described herein. As shown in FIG. 31, after the cross-sectional perimeter of implant 2800 is no longer constrained by secondary sheath lumen 2908, implant 2800 expands into the deployed configuration within vessel lumen 602.

In the exemplary embodiment, a valve 2930 is coupled to secondary sheath proximal end 2916, as shown in FIG. 30. Valve 2930 is any suitable valve, such as a hemostasis valve, that facilitates sealing of secondary sheath lumen 2908 while permitting relative longitudinal movement with respect to second guidewire 2404 and pusher tube 2920 extending therethrough.

Step 520 further includes retracting 594 delivery sheath 1901 over first guidewire 120 such that delivery sheath distal end 1904 is positioned outside vessel 604 adjacent to puncture 600, as shown in FIG. 31. In the exemplary embodiment, distal slot 1920 and window 1930 of delivery sheath 1901 facilitate delivery sheath 1901 being withdrawn proximally from vessel lumen 602 without interfering with implant 2800 traversing beneath puncture 600. In the exemplary embodiment, step 594 also includes extracting first guidewire 120 proximally from vessel lumen 602 and delivery sheath lumen 1908. In alternative embodiments, first guidewire 120 is maintained in position within vessel lumen 602 and delivery sheath lumen 1908.

Step 520 additionally includes advancing 596 a first locking mechanism 3104 distally along first anchor suture 2828 such that the first locking mechanism 3104 couples against an exterior of the wall of vessel 604 adjacent puncture 600, as shown in FIG. 32. For example, an operator applies tension to first anchor suture 2828 (e.g., by pulling distal end 2416 of second guidewire 2404 proximally) such that inferior flap 606 is elevated into a position proximate to puncture 600, and tension is maintained as locking mechanism 3104, such as, but not limited to, a suture knot, is advanced 596 distally along first anchor suture 2828. Thus, first anchor suture 2828, which was pulled at least partially through delivery sheath lumen 1908 in step 562 via the magnetic coupling of guidewire magnet 2408 and stylet magnet 2508, facilitates locking implant 2800 firmly against the interior of the wall of vessel 604 adjacent puncture 600.

In the exemplary embodiment, step 520 additionally includes advancing 598 a second locking mechanism 3104 distally along second anchor suture 2832 such that the second locking mechanism 3104 couples against an exterior of the wall of vessel 604 adjacent secondary access site 612, as shown in FIG. 32. For example, an operator applies tension to second anchor suture 2832 (e.g., by pulling proximal end 2412 of second guidewire 2404 proximally), and tension is maintained as locking mechanism 3104, such as, but not limited to, a suture knot, is advanced 596 distally along second anchor suture 2832. Thus, second anchor suture 2832, which was retained at least partially within secondary sheath lumen 2908 during step 592 of deploying implant 2800, facilitates locking implant 2800 firmly against the interior of the wall of vessel 604 adjacent puncture 600.

In alternative embodiments, implant 2800 is secured in position adjacent puncture 600 and secondary access site 612 in any suitable fashion that enables implant 2800 to function as described herein.

Due to the positioning of implant 2800 to traverse underneath puncture 600, implant 2800 elevates inferior flap 606 as implant 2800 in the deployed configuration is drawn against the interior of the wall of vessel 604 by locking mechanisms 3104, facilitating hemostasis at puncture 600. In some embodiments, secondary sheath 2904 includes a side port (not shown) adjacent to proximal end 2916 to facilitate injection of a suitable material for performing a completion arteriogram to verify adequate closure of puncture 600. In the exemplary embodiment, second guidewire 2404 is then severed from implant 2800, first anchor suture 2828, and/or second anchor suture 2832. Second guidewire 2404 is extracted by pulling proximal end 2412 proximally to remove at least a portion of second guidewire 2404 from a tract of tissue 608 adjacent to secondary access site 612 and, in some embodiments, by pulling distal end 2416 proximally to remove another portion of second guidewire 2404 proximally from a tract of tissue 608 adjacent to puncture 600. In alternative embodiments, second guidewire 2404 is removed in any suitable fashion that enables closure system 100 to function as described herein.

The methods and systems described herein provide advantages as compared to at least some prior methods and systems for facilitating hemostasis at a puncture of a vessel, and in particular, but not by way of limitation, at a large-bore opening in a vessel, such as one caused by a catheter introducer of 14 Fr to 24 Fr diameter. Specifically, the system includes a delivery sheath configured for insertion over a first guidewire into the vessel puncture, such as through the tract formed by the primary medical procedure. A second guidewire is advanced into the vessel at a secondary access site offset from the puncture. The second guidewire may be used in any of several ways to facilitate hemostasis at the puncture. In some embodiments, the second guidewire includes a magnet that is configured to magnetically couple to a stylet magnet advanced through the delivery sheath, such that a distal end of the second guidewire is captured and drawn proximally through the delivery sheath. A flexibly curved implant is deployable through the secondary access site using a secondary sheath. The implant includes a first anchor suture configured to move proximally into the delivery sheath lumen with the captured second guidewire, and a second anchor suture configured to extend within the secondary sheath lumen after the implant is deployed in the vessel. Locking mechanisms are advanced along the anchor sutures to fix the implant in place across the puncture and the secondary access site. In some embodiments, use of the second guidewire inserted at the secondary access site offset from the puncture facilitates capture by the closure system of an inferior flap of the vessel at the puncture, reducing or eliminating a potential for the inferior flap to interfere with a seal of the puncture site or to obstruct the femoral artery.

Exemplary embodiments of medical devices are described above in detail. The methods and systems are not limited to the specific embodiments described herein, but rather, operations of the methods and components of the systems may be utilized independently and separately from other operations and/or components described herein. For example, the methods and apparatus described herein may have other industrial and/or consumer applications and are not limited to practice with medical devices as described herein. Rather, one or more embodiments may be implemented and utilized in connection with other industries.

This written description uses examples to illustrate the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A closure system configured to facilitate hemostasis at a puncture of a vessel, said closure system comprising:
    a delivery sheath that extends longitudinally from a delivery sheath proximal end to a delivery sheath distal end, said delivery sheath defines a delivery sheath lumen extending therethrough, said delivery sheath lumen configured to receive a first guidewire therethrough;
    an introducer needle configured to selectively couple to said delivery sheath for movement relative to said delivery sheath, said introducer needle configured to form a secondary access site in the vessel at an offset from the puncture after said delivery sheath distal end is advanced through the puncture; and
    a stylet configured to be received through said delivery sheath lumen adjacent to the first guidewire, said stylet comprising a stylet magnet configured to magnetically couple to a guidewire magnet of a second guidewire advanced through the secondary access site.

2. The closure system according to claim 1, wherein the offset is in a range from about 1.0 centimeters to about 3.0 centimeters.

3. The closure system according to claim 1, further comprising:
    a secondary sheath configured to selectively couple to said delivery sheath for movement relative to said delivery sheath, said secondary sheath extends longitudinally from a secondary sheath proximal end to a secondary sheath distal end, said secondary sheath defines a secondary sheath lumen extending therethrough and configured to receive the second guidewire, said secondary sheath configured to be advanced over the second guidewire such that said secondary sheath distal end advances through the secondary access site into a lumen of the vessel; and
    an implant comprising an elongated body having a flexible curvature about an axis parallel to a direction of elongation of said body, wherein said body is flexibly transitionable between a deployed configuration and a delivery configuration, wherein said body in the delivery configuration is configured to be retained in said secondary sheath lumen and said body in the deployed configuration is configured to conform to an interior circumference of a wall of the vessel.

4. The closure system according to claim 3, wherein said implant further comprises a first anchor suture coupled to said body, said first anchor suture configured to extend at least partially through said delivery sheath lumen when said body is positioned in the lumen of the vessel adjacent to the puncture.

5. The closure system according to claim 4, wherein said implant further comprises a second anchor suture coupled to said body, said second anchor suture configured to extend at least partially through said secondary sheath lumen when said body is positioned in the lumen of the vessel adjacent to the puncture.

6. The closure system according to claim 3, wherein said body is sized to extend from the secondary access site to a location in the lumen of the vessel distal of the puncture.

7. The closure system according to claim 3, wherein said body has an unforced width that is one of greater than and approximately equal to a width of said body in the deployed configuration, wherein said body is biased to spring back from the delivery configuration towards the unforced width.

8. The closure system according to claim 1, wherein said delivery sheath further comprises a window defined in and extending through a wall of said delivery sheath, said window having a width about half a circumference of said delivery sheath, said window configured to be positioned beneath and face away from the puncture when said delivery sheath distal end is inserted into a lumen of the vessel.

9. A method of facilitating hemostasis at a puncture of a vessel, said method comprising:
    advancing a distal end of a delivery sheath through the puncture into a lumen of the vessel, wherein the delivery sheath extends longitudinally from a delivery sheath proximal end to the delivery sheath distal end, the delivery sheath defines a delivery sheath lumen extending therethrough, wherein the delivery sheath lumen receives a first guidewire therethrough;
    advancing a distal end of a second guidewire through a secondary access site in the vessel at an offset from the puncture, wherein the second guidewire includes a guidewire magnet;
    extracting a stylet proximally from the delivery sheath lumen, wherein a stylet magnet of the stylet magnetically couples to the guidewire magnet within the lumen of the vessel, such that the distal end of the second guidewire extends proximally from the delivery sheath proximal end after the stylet is extracted;
    advancing an implant through the secondary access site into the lumen of the vessel adjacent to the puncture, wherein the implant includes a first anchor suture constrained to move proximally with the second guidewire at least partially through the delivery sheath lumen; and advancing a first locking mechanism distally along the first anchor suture, such that the first locking mechanism couples against an exterior of the wall of the vessel adjacent the puncture.

10. The method according to claim 9, further comprising:
coupling an introducer needle to the delivery sheath for movement relative to the delivery sheath; and
advancing the introducer needle into the vessel, after the delivery sheath distal end is advanced through the puncture, to form the secondary access site in the vessel.

11. The method according to claim 10, wherein said advancing the distal end of the second guidewire through the secondary access site comprises advancing the distal end of the second guidewire through the introducer needle.

12. The method according to claim 10, further comprising:
advancing a third guidewire through the introducer needle into the lumen of the vessel;
advancing a secondary dilator and a secondary sheath over the third guidewire distally through the secondary access site into the lumen of the vessel; and
removing the secondary dilator and the third guidewire, wherein said advancing the distal end of the second guidewire through the secondary access site comprises advancing the distal end of the second guidewire through the secondary sheath.

13. The method according to claim 10, wherein said advancing the introducer needle into the vessel comprises advancing the introducer needle into the vessel at the offset in a range from about 1.0 centimeters to about 3.0 centimeters.

14. The method according to claim 9, wherein the delivery sheath further includes a window defined in and extending through a wall of the delivery sheath, said advancing the distal end of the delivery sheath through the puncture into the lumen of the vessel further comprises positioning the window beneath and facing away from the puncture, said method further comprising advancing the stylet through the delivery sheath lumen such that the stylet magnet is positioned proximate to the window and in position to magnetically cooperate with the guidewire magnet positioned in the lumen of the vessel.

15. The method according to claim 9, further comprising fixedly coupling the first anchor suture to the second guidewire one of (i) before the guidewire magnet magnetically couples to the stylet magnet, (ii) after the guidewire magnet magnetically couples to the stylet magnet and before said extracting the stylet, and (iii) after said extracting the stylet.

16. The method according to claim 9, further comprising applying tension to the distal end of the second guidewire when the second guidewire is positioned proximally from the delivery sheath proximal end, such that a portion of the second guidewire is pulled at least partially through the delivery sheath lumen, wherein the portion of the second guidewire defines the first anchor suture.

17. The method according to claim 9, wherein said advancing the implant through the secondary access site comprises:
coupling a secondary sheath to the delivery sheath, wherein the secondary sheath extends longitudinally from a secondary sheath proximal end to a secondary sheath distal end, the secondary sheath defines a secondary sheath lumen extending therethrough;
advancing the secondary sheath distally over the second guidewire such that the secondary sheath distal end advances through the secondary access site into the vessel lumen; and
deploying the implant from the distal end of the secondary sheath.

18. The method according to claim 17, wherein said deploying the implant from the distal end of the secondary sheath comprises:
positioning a pusher tube within the secondary sheath lumen; and
advancing the pusher tube distally with respect to the secondary sheath.

19. The method according to claim 17, wherein the implant includes an elongated body having a flexible curvature about an axis parallel to a direction of elongation of the body, and wherein said deploying the implant from the distal end of the secondary sheath comprises flexibly transitioning the body from a delivery configuration, configured to be retained with the secondary sheath lumen, to a deployed configuration, configured to conform to an interior circumference of a wall of the vessel.

20. The method according to claim 17, wherein the implant includes a second anchor suture that extends at least partially through the secondary sheath lumen after said advancing the implant through the secondary access site, said method further comprising advancing a second locking mechanism distally along the second anchor suture, such that the second locking mechanism couples against the exterior of the wall of the vessel adjacent the secondary access site.

* * * * *